US008445009B2

(12) United States Patent
MacPhee et al.

(10) Patent No.: US 8,445,009 B2
(45) Date of Patent: May 21, 2013

(54) PROCESSES FOR THE PRODUCTION OF SOLID DRESSINGS FOR TREATING WOUNDED TISSUE

(75) Inventors: Martin MacPhee, Darnestown, MD (US); Dawson Beall, Germantown, MD (US)

(73) Assignee: STB, Ltd, Bellevue, WA (US)

( * ) Notice: Subject to any disclaimer, the term of this patent is extended or adjusted under 35 U.S.C. 154(b) by 0 days.

(21) Appl. No.: 11/882,872

(22) Filed: Aug. 6, 2007

(65) Prior Publication Data

US 2008/0031934 A1 Feb. 7, 2008

Related U.S. Application Data

(60) Provisional application No. 60/835,423, filed on Aug. 4, 2006.

(51) Int. Cl.
A61F 13/00 (2006.01)
A61K 9/70 (2006.01)
A61L 15/16 (2006.01)
A61L 15/00 (2006.01)

(52) U.S. Cl.
USPC ........... 424/443; 424/444; 424/445; 424/446; 424/447

(58) Field of Classification Search
None
See application file for complete search history.

(56) References Cited

U.S. PATENT DOCUMENTS

| | | | |
|---|---|---|---|
| 1,975,504 A | 10/1934 | Formhals | |
| 2,533,004 A | 12/1950 | Ferry et al. | |
| 3,012,893 A | 12/1961 | Kremzner et al. | |
| 3,089,815 A | 5/1963 | Lieb et al. | |
| 3,523,807 A | 8/1970 | Gerendas | |
| 3,723,244 A | 3/1973 | Breillat, Jr. | |
| 4,265,233 A | 5/1981 | Sugitachi et al. | |
| 4,298,598 A | 11/1981 | Schwarz et al. | |
| 4,321,711 A | 3/1982 | Mano | |
| 4,359,049 A | 11/1982 | Redl et al. | |
| 4,362,567 A | 12/1982 | Schwarz et al. | |
| 4,373,519 A | 2/1983 | Errede et al. | |
| 4,377,159 A | 3/1983 | Hansen | |
| 4,377,572 A | 3/1983 | Schwarz et al. | |
| 4,393,041 A | 7/1983 | Brown et al. | |
| 4,394,370 A | 7/1983 | Jefferies | |
| 4,407,787 A | 10/1983 | Stemberger | |

(Continued)

FOREIGN PATENT DOCUMENTS

AU B-83581/82 11/1982
AU B-43122/8 12/1985

(Continued)

OTHER PUBLICATIONS

SAS/STAT Users Guide, 4th ed., Cary, N.C., SAS Institute Inc., 1990.

(Continued)

Primary Examiner — Isis Ghali
(74) Attorney, Agent, or Firm — Cozen O'Connor

(57) ABSTRACT

Disclosed are processes for preparing solid dressings for treated wounded tissue in mammalian patients, such as a human, comprising a haemostatic layer consisting essentially of a fibrinogen component and a fibrinogen activator. Also disclosed are methods for treating wounded tissue using these dressings and frozen and liquid compositions useful for preparing the haemostatic layer(s) of these dressings or for treating wounded tissue in a mammal.

21 Claims, 10 Drawing Sheets

HUMAN CLOTTING CASCADE

U.S. PATENT DOCUMENTS

| | | | |
|---|---|---|---|
| 4,414,976 A | 11/1983 | Schwarz et al. | |
| 4,427,650 A | 1/1984 | Stroetmann | |
| 4,427,651 A | 1/1984 | Stroetmann | |
| 4,442,655 A | 4/1984 | Stroetmann | |
| 4,453,939 A | 6/1984 | Zimmerman et al. | |
| 4,472,840 A | 9/1984 | Jefferies | |
| 4,516,276 A | 5/1985 | Mittelmeier et al. | |
| 4,548,763 A | 10/1985 | Nalewajek et al. | |
| 4,597,960 A | 7/1986 | Cohen | |
| 4,600,574 A | 7/1986 | Lindner et al. | |
| 4,606,337 A | 8/1986 | Zimmerman et al. | |
| 4,617,293 A | 10/1986 | Wahlig et al. | |
| 4,619,913 A | 10/1986 | Luck et al. | |
| 4,619,989 A | 10/1986 | Urist | |
| 4,627,879 A | 12/1986 | Rose et al. | |
| 4,631,055 A | 12/1986 | Redl et al. | |
| 4,642,120 A | 2/1987 | Nevo et al. | |
| 4,683,142 A | 7/1987 | Zimmerman et al. | |
| 4,714,457 A | 12/1987 | Alterbaum | |
| 4,717,717 A | 1/1988 | Finkenaur | |
| 4,761,471 A | 8/1988 | Urist | |
| 4,789,732 A | 12/1988 | Urist | |
| 4,816,339 A | 3/1989 | Tu et al. | |
| 4,820,626 A | 4/1989 | Williams et al. | |
| 4,837,379 A | 6/1989 | Weinberg | |
| 4,861,757 A | 8/1989 | Antoniades et al. | |
| 4,874,746 A | 10/1989 | Antoniades et al. | |
| 4,909,251 A | 3/1990 | Seelich | |
| 4,928,603 A | 5/1990 | Rose et al. | |
| 4,952,403 A | 8/1990 | Vallee et al. | |
| RE33,375 E | 10/1990 | Luck et al. | |
| 4,969,880 A | 11/1990 | Zamierowski | |
| 4,983,581 A | 1/1991 | Antoniades et al. | |
| 4,997,425 A | 3/1991 | Shioya et al. | |
| 5,019,559 A | 5/1991 | Antoniades et al. | |
| 5,023,082 A | 6/1991 | Friedman et al. | |
| 5,024,742 A | 6/1991 | Nesburn et al. | |
| 5,030,215 A | 7/1991 | Morse et al. | |
| 5,034,375 A | 7/1991 | Antoniades et al. | |
| 5,035,887 A | 7/1991 | Antoniades et al. | |
| 5,059,123 A | 10/1991 | Jernberg | |
| 5,100,396 A | 3/1992 | Zamierowski | |
| 5,124,155 A | 6/1992 | Reich | |
| 5,139,527 A | 8/1992 | Redl et al. | |
| 5,171,318 A | 12/1992 | Gibson et al. | |
| 5,171,579 A | 12/1992 | Ron et al. | |
| 5,206,023 A | 4/1993 | Hunziker | |
| 5,219,328 A * | 6/1993 | Morse et al. | 604/500 |
| 5,226,877 A | 7/1993 | Epstein | |
| 5,290,552 A | 3/1994 | Sierra et al. | |
| 5,294,314 A | 3/1994 | Nesburn et al. | |
| 5,368,858 A | 11/1994 | Hunziker | |
| 5,431,790 A | 7/1995 | Nesburn et al. | |
| 5,702,715 A | 12/1997 | Nikolaychik et al. | |
| 5,716,645 A | 2/1998 | Tse et al. | |
| 5,723,010 A | 3/1998 | Yui et al. | |
| 5,763,411 A | 6/1998 | Edwardson et al. | |
| 6,054,122 A | 4/2000 | MacPhee et al. | |
| 6,056,970 A | 5/2000 | Greenawalt et al. | |
| 6,117,425 A | 9/2000 | MacPhee et al. | |
| 6,124,273 A | 9/2000 | Drohan et al. | |
| 6,197,325 B1 | 3/2001 | MacPhee et al. | |
| 6,447,774 B1 | 9/2002 | Metzner et al. | |
| 6,762,336 B1 | 7/2004 | MacPhee et al. | |
| 7,189,410 B1 | 3/2007 | Drohan et al. | |
| 2006/0155234 A1 | 7/2006 | MacPhee et al. | |

FOREIGN PATENT DOCUMENTS

| | | |
|---|---|---|
| AU | B-75097/87 | 1/1988 |
| CA | 1119516 | 3/1982 |
| CA | 1168982 | 6/1984 |
| DE | 3037270 | 5/1982 |
| EP | 0081990 | 6/1983 |
| EP | 0312208 | 4/1989 |
| EP | 0443724 | 8/1991 |
| EP | 0485210 | 5/1992 |
| EP | 0562864 | 9/1993 |
| GB | 2041942 | 9/1980 |
| GB | 2042556 | 9/1980 |
| GB | 1584080 | 2/1981 |
| GB | 2102811 | 2/1983 |
| GB | 2137209 | 3/1984 |
| GB | 2185747 | 7/1987 |
| JP | 54104687 | 8/1979 |
| JP | 60204725 | 10/1985 |
| JP | 62246370 | 10/1985 |
| JP | 63115564 | 4/1986 |
| RU | 2193897 C2 | 12/2002 |
| RU | 2235539 C1 | 9/2004 |
| WO | WO 81/00516 | 3/1981 |
| WO | WO 86/00526 | 1/1986 |
| WO | WO 86/01814 | 3/1986 |
| WO | WO 86/03122 | 6/1986 |
| WO | WO 91/09573 | 7/1991 |
| WO | WO 91/17744 | 11/1991 |
| WO | WO 92/09301 | 6/1992 |
| WO | WO 92/09697 | 6/1992 |
| WO | WO 92/13565 | 8/1992 |
| WO | WO 92/22312 | 12/1992 |
| WO | WO 93/05067 | 3/1993 |
| WO | WO 94/20133 | 9/1994 |
| WO | 97/15188 A1 | 5/1997 |
| WO | 97/28832 A1 | 8/1997 |
| WO | WO 97/28832 | 8/1997 |
| WO | 99/56798 A1 | 11/1999 |
| WO | 2004/010913 A1 | 2/2004 |
| WO | 2008/019126 A2 | 2/2008 |
| WO | 2008/019129 A2 | 2/2008 |

OTHER PUBLICATIONS

McManus, et al., Modern Hemostatic Agents for Hemorrhage Control—A Review and Discussion of Use in Current Combat Operations, Business Briefing: Emergency Medical Review 2005, p. 75-79 (presently available on-line at www.touchbriefings.com/pdf/1334/Wedmore.pdf).

Acheson, et al., Comparison of Hemorrhage Control Agents Applied to Lethal Extremity arterial Hemorrhages in Swine, J. Trauma, 59:865-874, 2005.

Sondeen, et al., Comparison of 10 Different Hemostatic Dressings in an Aortic Injury, J. Trauma, 54:280-285, 2003.

Kheirabadi, et al., Hemostatic Efficiency of Two Advanced Dressings in an Aortic Model in Swine, J. Trauma 59:25-35, 2005.

Meyer, et al., Determination of Water by titration with Coulometrically Generated Karl Fischer Reagant, Analytical Chem., 31:215-219, 1959.

May, et al., Determination of Residual Mositure in Freeze-dried Viral Vaccines: Karl Fischer, Gravimetric and Thermogravimetric Methodologies, J. Biol. Standardization, 10:249-259, 1982.

Centers for Biologics Evaluation and Research, Guideline for Determination of Residual Mositure in Dried Biological Products, FDA, 83-93, 1990.

Holcomb, et al,: Advanced Hemostatic Dressing Development Program: Animal Model Selection Criteria and Results of a Study of Nine Hemostatic Dressings in a Model of Severe Large Venous Hemorrhage and Hepatic Injury in Swine, J. Trauma, 55: 518-526, Sep. 2003.

Dascombe, et al., Application of Thrombin Based Fibrin Glue and Non-Thrombin Based Batroxobin Glue on Intact Human Blood Vessels: Evidence for Transmural Thrombin Activity, Thromb. Haemost., 78:947-51, 1997.

Hahn, et al., Purification and Molecular Cloning of Calobin, a Thrombin-like Enzyme from Agkistrodon Caliginosus (Korean Viper), J. Biochem. (Tokyo) 119:835-43, 1996.

Fortova, et al., Simultaneous Isolation of Protein C Activator, Fibrin Clot Promoting Enzyme (Fiprozyme) and Phospholipase A2 from the Venom of the Southern Copperhead Snake, J. Chromatogr. S. Biomed. Appl. 694:49-53, 1997.

Andriano-Escarso, et al., Toxicon. 35: 1043-52, 1997.

"Coagulation Cascade," available at <http://www.enzymeresearch.co.uk/CASCADE_erl_2004.pdf> (last Accessed Jun. 24, 2008).

International Search Report for International Application No. PCT/US99/10952, mailed Sep. 17, 1999.

Achauer, et al., The Hemostatic Effect of Fibrin Glue on Graft Donor Sites, Journal of Burn Care & Rehabilitation, vol. 15, No. 1, p. 24-28, Jan./Feb. 1994.

Adelmann-Grill, et al., Chemotatic Migration of Normal Dermal Fibroblasts Towards Epidermal Growth Factor and its Modulation by Platelet-Derived Growth Factor and Transforming Growth Factor-Beta, European Journal of Cell Biology, vol. 51, 322-326, 1990.

Akrami, et al., Abdichtung von Kunststoffprothesen beim Ersatz der Aorta im thorakalen Bereich—Replacement of the Thoracic Aorta by Sealed Dacron Prostheses, U.S. Appl. No. 09/890,795, Thoraxchirurgie vol. 26, p. 144-147, 1978.

Albrektsson, et al., Fibrin Adhesive System (FAS) Influence on Bone Healing Rate, Acts orthop. Scand. vol. 53, p. 757-763, Munksgaard, 1982.

Alving, et al., Fibrin Sealant: Summary of a Conference on Characteristics and Clinical Uses, The Journal of the American Association of Blood Banks, vol. 35, No. 9, p. 783-790, Sep. 1995.

Allen, et al., Influence of Endothelial Cell Seeding on Platelet Deposition and Patency in Small-Diameter Dacron Arterial Grafts, Journal of Vascular Surgery, vol. 1, No. 1, p. 224-233, Jan. 1984.

Growth Factor—Supplemented Fibrin Glue, The American Red Cross, 1989 Biomedical Research and Development Report, p. 21.

Growth Factor—Supplemented Fibrin Glue, The American Red Cross Biomedical Research and Development Report 1990, p. 20.

Jorgensen, Biomechanical Properties and Collagen Formation in Subcutaneously Implanted Cellulose Sponges Treated with Fibrin Sealant, European Surgery Research, vol. 17, p. 264-268, 1985.

Arbes, et al., First Clinical Experience with Heterologous Cancellous Bone Grafting Combined with the Fibrin Adhesive System (F.A.S.), Archives of Orthopaedic and Traumatic Surgery, vol. 98, p. 183-188, 1981.

Bagdy, et al., Application of Bovine Fibrin Foam and of a Mixture of Thrombin and Fibrin Powders as Haemostatic Agents, Acta Physiologica Academiae Scientiarum Hungaricae, Magyar Tudomanyos Akademia, p. 493-504, May 1951.

Bailey, et al., Chemical, Clinical, and Immunological Studies on the Products of Human Plasma Fractionation, XXI. The Use of Fibrin Foam as a Hemostatic Agent in Neurosurgery: Clinical and Pathological Studies, Journal of Clinical Investigation, vol. 23, No. 4, p. 591-596, Feb. 17, 1944.

Bailey, et al., Chemical, Clinical, and Immunological Studies on the Products of Human Plasma Fractionation, XXII. Fibrin Films in Neurosurgery, With Special Reference to Their Use in the Repair of Dural Defects and in the Prevention of Meningocerebral Adhesions, Journal for Clinical Investigation, vol. 23, No. 4, p. 597-600, Feb. 17, 1944.

Bailey, et al., Fibrin Film in Neurosurgery, Further Studies, vol. 4, p. 465-471, J. Neurosurgery, May 6, 1947.

Baird, et al., Fibroblast Growth Factors, British Medical Bulletin, vol. 45, No. 2, p. 438-452, 1989.

Berger, et al., Healing of Arterial Prostheses in Man: Its Incompleteness, Annals of Surgery, vol. 175, No. 1 p. 118-127, Jan. 1972.

Bishara, et al., Effects of a Fibrin-Sealant Wound Dressing on the Healing of Full-Thickness Wounds of the Hard Palate: Preliminary Report, Cleft Plate Journal, vol. 23, No. 2, p. 144-152, Apr. 1986.

Bösch, et al., Die Technik der Fibrinspongiosaplastik, Archiv für Orthopädische und Unfall-Chirurgie, vol. 90, p. 63-75, 1977.

Bösch, et. al., Die autologe Spongiosatransplantation unter Anwendung des Fibrinklebesystems im Tierexperiment, Wiener klinische Wochenschrift, p. 628-634, Sep. 28, 1979.

Bösch, et. al., Experimental Investigations of the Effect of the Fibrin Adhesive on the Kiel Heterologous Bone Graft, Archives of Orthopaedic and Traumatic Surgery, vol. 96, 1.

Bösch, Die Fibrinspongiosaplastik Experimentelle Untersuchungen und klinische Erfahrung, Wiener klinische Wochenschrift, 93, Heft 11, p. 3-26, 1981.

Borst, et al., Fibrin Adhesive: An Important Hemostatic Adjunct in Cardiovascular Operations, The Journal of Thoracic and Cardiovascular Surgery, vol. 84, No. 4, p. 548-553, Oct. 1982.

Brown, et al., Decreased Wound Contraction With Fibrin Glue-Treated Skin Grafts, Archives of Surgery, vol. 127, No. 4, p. 404-406, Apr. 1992.

Burgess, et al., The Heparin-Binding (Fibroblast) Growth Factor Family of Proteins, Annual Review of Biochemistry, vol. 58, p. 575-606, 1989.

Byrne, et al., Effect of Fibrin Glues on the Mechanical Properties of Healing Wounds, British Journal of Surgery, vol. 78, No. 7, p. 841-843, Jul. 1991.

Carter, et al., Clinical Experience with Crude Preparations of Growth Factors in Healing of Chronic Wounds in Human Subjects, Growth Factors and Other Aspects of Wound Healing: Biological and Clinical Implications, p. 303-317, 1988.

Clark, et al., Fixation of Skin-Grafts With Human Plasma and Thrombin, The Lancet, No. 6343, p. 498-500, Apr. 21, 1945.

Clowes, et al., Graft Endothelialization: The Role of Angiogenic Mechanisms, Journal of Vascular Surgery, vol. 13, No. 5, p. 734-736, May 1991.

Clowes, et al., Mechanisms of Arterial Graft Healing, American Journal of Physiology, vol. 123, No. 2, p. 200-230.

Conant, et al., Treatment of Condylomata Acuminata with Intralesional 5-Fluorouracil Therapeutic Implant (MPI 5003), Clinical Research, vol. 39, No. 4, Dec. 1991.

Cronkite, et al., Use of Thrombin and Fibrinogen in Skin Grafting, The Journal of the American Medical Association, vol. 124, No. 14, p. 976-978, Apr. 1, 1944.

Cziperle, et al., Enhanced Endothelialization of Expanded Polytetrafluoroethylene Grafts by Haparin Binding Growth Factor-Type 1 (HBGF-1) Pretreatment.

Davidson, et al., Mechanisms of Accelerated Wound Repair Using Epidermal Growth Factor and Basic Fibroblast Growth Factor, Biological and Clinical Implications, p. 63-75, 1988.

Dees, The Use of an Intrapelvic Coagulum in Pyelolithotomy, Southern Medical Journal, vol. 36, No. 3, p. 167-175, Mar. 1943.

Dees, et al., The Properties of Human Fibrinogen Coagulum—Preliminary Report, The Journal of Urology, vol. 49, p. 503-511, 1943.

Dees, Chemical, Clinical, and Immunological Studies on the Products of Human Plasma Fractionation, XVIII. Fibrinogen Coagulum as an Aid in the Operative Removal of Renal Calculi, Journal for Clinical Investigation, vol. 23, No. 4, p. 576-579, Feb. 17, 1944.

Dees, The Use of Fibrinogen Coagulum in Pyelolithotomy, The Journal of Urology, vol. 56, p. 271-283, 1946.

Deyerling, et al., A suspension of Fibrin Glue and Antibiotic for Local Treatment of Myocotic Aneurysms in Endocarditis—An Experimental Study, Thoracic Cardiovascular Surgeon, vol. 32, p. 369-372, 1984.

Dresdale, et al., Hemostatic Effectiveness of Fibrin Glue Derived from Single-Donor Fresh Frozen Plasma, The Annals of Thoracic Surgery, vol. 40, No. 4, p. 385-387, Oct. 31, 1985.

Berguer, et al., Warning: Fatal Reaction to the Use of Fibrin Glue in Deep Hepatic Wounds. Case Reports, The Journal of Trauma, vol. 31, No. 3, p. 408-411, Mar. 1991.

Garza, et al., Fibrin Glue and Hemostatis in Liver Trauma: A Case Report, The Journal of Trauma, vol. 30, No. 4, p. 512-513, Apr. 1990.

Jakob, Use of Fibrin Sealant for Reinforcing Arterial Anastomoses, Journal of Vascular Surgery, vol. 1, No. 1, p. 171-180, Jan. 1984.

Heaton, Fibrin Foam and Fibrin Film, Medical Department, United States Army, Blood Program in World War II, p. 363-369, 1964.

Kram, et al., Techniques of Splenic Preservation Using Fibrin Glue, The Journal of Trauma, vol. 30, No. 1, p. 97-101, 1990.

Ochsner, et al., Fibrin Glue as a Hemostatic Agent in Hepatic and Splenic Trauma, The Journal of Trauma, vol. 30, No. 7, p. 884-887, Jul. 1990.

Matthew, et al., Four Years' Experience with Fibrin Sealant in Thoracic and Cardiovascular Surgery, The Annals of Thoracic Surgery, vol. 50, No. 1, p. 40-44, 1990.

Ness, et al., Cryoprecipitate as a Reliable Source of Fibrinogen Replacement, The Journal of the American Medical Association, vol. 241, No. 16, p. 1690-1691, Apr. 20, 1979.

Rapaport, et al., Clinical Significance of Antibodies to Bovine and Human Thrombin and Factor V After Surgical Use of Bovine Thrombin, American Journal of Clinical Pathology, vol. 97, No. 1, p. 84-91, Jan. 1992.

Reiss, et al., Autologous Fibrin Glue: Production and Clinical Use, Transfusion Medicine Reviews, vol. X, No. 2, p. 85-92, Apr. 1996.
Rocko, et al., Exsanguination in Public—A Preventable Death (Abstract), The Journal of Trauma, vol. 22, No. 7, p. 635.
Schiele, et al., Haemostyptic Preparations on the Basis of Collagen Alone and as Fixed Combination with Fibrin Glue, Clinical Materials, vol. 9, Nos. 3&4, p. 169-177, Apr. 3, 1992.
Sloand, et al., Safety of the Blood Supply, The Journal of the American Medical Association, vol. 274, No. 17, p. 1368-1373, Nov. 1, 1995.
Spotnitz, Fibrin Sealant in the United States: Clinical Use at the University of Virginia, Thrombosis and Haemostatis, p. 482-485, 1995.
Zimmerman, et al., Great Ideas in the History of Surgery, Norman Publishing, San Francisco, p. 31, 1993.
Dresdale, et al., Preparation of Fibrin Glue From Single-Donor Fresh-Frozen Plasma, Surgery vol. 97, No. 6, p. 750-755, Jun. 1985.
Durham, et al., A Method for Preparation of Fibrin Glue, The Journal of Laryngology and Otology, vol. 101, p. 1182-1186, Nov. 1987.
Dvorak, et al., Fibrin Containing Gels Induce Angiogenesis, The United States and Canadian Academy of Pathology, Inc., vol. 57, No. 6, p. 673-686, 1987.
Epstein, et al., A New Autologous Fibrinogen-Based Adhesive for Otologic Surgery, Annals Publishing Company, vol. 95, p. 40-45, 1986.
Ferry, et al., Chemical, Clinical, and Immunological Studies on the Products of Human Plasma Fractionation, p. 566-572, Feb. 17, 1944.
Foxall, et al., Adult Human Endothelial Cell Coverage of Small-Caliber Dacron and Polytetrafluoroethylene Vascular Prostheses in Vitro, Journal of Surgical Research vol. 41, p. 158-172, Aug. 1986.
Froesch, et al., Actions of Insulin-Like Growth Factors, Ann Rev. Physiol., vol. 47, p. 443-67, 1985.
Frucht-Perry, et al., Fibrin-Enmeshed Tobramycin Liposomes: Single Application Topical Therapy of Pseudomonas Keratitis, Cornea vol. 11, No. 5, p. 393-397, 1992.
Gerendas, Fibrin Products as Aids in Hemostasis and Wound Healing, p. 277-316, 1968.
Gersdorff, et al., A New Procedure for Bone Reconstruction in Oto-Microsurgery: A Mixture of Bone Dust and Fibrinogen Adhesive, Journal of the American Laryngological, Rhinological and Otological Society, Inc., vol. 95, No. 10, p. 1278-1280, Oct. 1985.
Gibble, et al., Fibrin glue: The Perfect Operative Sealant?, Transfusion, vol. 30, No. 1, p. 741-747, 1990.
Glynn, et al., The Antigenic Properties of Fibrin Films and Foams Prepared From Human and From Bovine Blood Plasma, The Journal of Immunology, vol. 53, No. 2, p. 143-150, Jun. 1946.
Gospodarowicz, et al., Structural Characterization and Biological Functions of Fibroblast Growth Factor, Endocrine Reviews, vol. 8, No. 2, p. 95-114, May 1987.
Goudarzi, Klinische Erfahrungen mit einer Fibrin-Nebacetin-Spongiosaplombe zur Behandlung der chronischen Knocheninfektionen und als lokale Infektionsprophylaxe bei nicht infiziertem Knochenherd, Akt. Traumatol. vol. 13, p. 205-209, 1983.
Graham, et al., Expanded Polytetrafluoroethylene Vascular Prostheses Seeded With Enzymatically Derived and Cultured Canine Endothelial Cells, Surgery, vol. 91, No. 5, p. 550-559, May 1982.
Greco, et al., Fibrin-antibiotic mixtures: An in vitro Study Assessing the Possibility of Using a Biologic Carrier for Local Drug Delivery, Journal of Biomedical Materials Research, vol. 25, p. 39-51, 1991.
Greenhalgh, et al., PDGF and FGF Stimulate Wound Healing in the Genetically Diabetic Mouse, American Journal of Pathology, vol. 136, No. 6, p. 1235-1246, Jun. 1990.
Greisler, et al., Endothelial Cell Growth Factor Attachment to Biomaterials, Trans Am Soc Artif Intern Organs, vol. XXXII, p. 346-349, 1986.
Greisler, et al., Biomaterial Pretreatment With ECGF to Augment Endothelial Cell Proliferation, Journal of Vascular Surgery, vol. 5, No. 2, p. 393-402, Feb. 1987.
Greisler, et al., Enhanced Endotheliazilation of Expanded Polytetrafluoroethylene Grafts by Fibroblast Growth Factor Type 1 Pretreatment, Surgery, vol. 112, No. 2, p. 244-255, Aug. 1992.
Greisler, et al., Enhancement of Polytretrafluoroethylene Endothelialization by Pretreatment with Fibrin Glue Containing Heparin Binding Growth Factor-Type 1(HBGF-1), p. 50.
Gundry, et al., A Quantitative and Qualitative Comparison of Fibrin Glue, Albumin, and Blood as Agents to Pretreat Porous Vascular Grafts, Journal of Surgical Research, vol. 43, No. 1, p. 75-77, Jul. 1987.
Harker, et al., Platelet Consumption by Arterial Prostheses: The Effects of Endothelialization of Pharmacologic Inhibition of Platelet Function, Am. Surg., p. 594-601, Nov. 1977.
Harris, et al., Heterogenous Skin Grafts by the Coagulum Contact Method, American Journal of Surgery, New Series vol. LXV, No. 3, p. 315-320, Sep. 1944.
Harrison, et al., Experiences With Fibrin Coagulum in Pyelolithotomy, The Journal of Urology, vol. 62, No. 1, p. 1-12, Jul. 1949.
Harrison, Jr., et al, Osteogenin Promotes Reexpression of Cartilage Phenotype by Dedifferentiated Articular Chondrocytes in Serum-Free Medium, Experimental Cell Research, vol. 192, p. 340-345, 1991.
Harting, et al., Glued Fixation of Split-Skin Graft to the Bony Orbit Following Exenteration, Plastic and Reconstructive Surgery, vol. 76, No. 4, p. 633-635, Oct. 1985.
Hattori, Bone Morphogenetic Protein—BMP, J. Jpn. Orthop. Assoc., vol. 64, p. 824-834, May 9, 1990.
Haverich, et al., The Use of Fibrin Glue for Sealing Vascular Prostheses of High Porosity, Thorac. Carivasc. Surgeon, vol. 29, p. 252-254.
Haverich, et al., Evaluation of Fibrin Seal in Animal Experiments, Thorac. Cardiovasc. Surgeon, vol. 30, No. 4, p. 195-242, Aug. 1982.
Haverich, et al., Histopathological Evaluation of Woven and Knitted Dacron Grafts for Right Ventricular Conduits: A Comparative Experimental Study, The Annals of Thoracic Surgery, vol. 37, No. 5, p. 404-411, May 1984.
Haverich, et al., Pericardial Flap-Plasty for Protection of the Tracheal Anastomosis in Heart-Lung Transplantation, Journal of Cardiac Surgery, vol. 4, No. 2, p. 136-139,1989.
Haverich, et al., Prevention of graft infection by bonding of gentamvcin to Dacron prostheses, Journal of Vascular Surgery, vol. 15, No. 1, p. 187-193, Jan. 1992.
Hawn, et al., Chemical, Clinical, and Immunological Studies on the Products of Human Plasma Fractionation, p. 580-585, 1944.
Hayek, et al., An In Vivo Model for Study of the Angiogenic Effects of Basic Fibroblast Growth Factor, Biochemical and Biophysical Research Communications, vol. 147, No. 2, p. 876-880, Sep. 15, 1987.
Herring, et al., Endothelial seeding of polytetrafluoroethylene popliteal bypasses, Journal of Vascular Surgery, vol. 6, No. 2, Aug. 1987.
Ho, et al., Drug Release From Glutaraldehyde-Treated Fibrin Gels, Drug Design and Delivery, vol. 7, p. 65-73, 1990.
Hoffman, Coagulum Pyelolithotomy, American Journal of Surgery, p. 598-602, Apr. 1950.
Holcomb, et al., Implications of New Dry Fibrin Sealant Technology for Trauma Surgery, The Surgical Clinics of North America, vol. 77, No. 4, p. 943-952, Aug. 1997.
Ikossi-O'Connor, et al., The Role of Fibrin Adhesive in Vascular Surgery, Journal of Surgical Oncology, vol. 23, p. 151-152, 1983.
Ingraham, et al., Clinical Use of Products of Human Plasma Fractionation, III The Use of Products of Fibrinogen and Thrombin in Surgery, The Journal of the American Medical Association, vol. 126, No. 11, p. 680-685, Nov. 11, 1944.
Ingraham, et al., The Use of Products Prepared From Human Fibrinogen and Human Thrombin in Neurosurgery, Journal of Neurosurgery, vol. 1, p. 23-39, 1944.
Ingraham, et al., The Use of Fibrin Film as a Dural Substitute, The Journal of the American Medical Association, vol. 128, No. 15, p. 1088-1091, Aug. 11, 1945.
István, et al., Gastrointestinalis Vérzések Csillapitása Thrombin-Fibrin Készitménnyel, Orvosi Hetilap, vol. 105, Issue 5, p. 119-223, Feb. 2, 1964.
Jarrell, et al., Human Adult Endothelial Cell Growth in Culture, Journal of Vascular Surgery, vol. 1, No. 6, p. 757-764, Nov. 1984.

Jonas, et al., Biological Sealants and Knitted Dacron: Porosity and Histological Comparisons of Vascular Graft Materials with and without Collagen and Fibrin Glue Pretreatments, Ann Thorac Surgery, vol. 41, p. 657-663, Jun. 1986.

Jonas, et al., Biological Sealants and Knitted Dacron Conduits: Comparison of Collagen and Fibrin Glue Pretreatments in Circulatory Models, Ann Thorac Surgery, vol. 44, p. 283-290, Sep. 1987.

Kabuto, et al., Experimental Study of Intraoperative Local Chemotherapy with Fibrin Glue Containing Nitrosourea for Malignant Gliomas, Surgical Neurology, vol. 44, No. 2, p. 151-157, Aug. 1995.

Kaehler, et al., Precoating Substrate and Surface Configuration Determine Adherence and Spreading of Seeded Endothelial Cells on Polytetrafluoroethylene Grafts, Journal of Vascular Surgery, vol. 9, No. 4, p. 535-541, Apr. 1989.

Karck, et al., Pretreatment of Prosthetic Valve Sewing-Ring with the Antibiotic/Fibrin Sealant Compound as a Prophylactic Tool Against Prosthetic Valve endocarditis, Eur J Cardio-thorac Surg 4:142-146, 1990.

Kawamura, et al., Human Fibrin is a Physiologic Delivery System for Bone Morphogenetic Protein, Critical Orthopaedica and Related Research, No. 235, p. 302-310, Oct. 1988.

Kempeczinski, et al., Endothelial Cell Seeding of a New PTFE Vascular Prosthesis, Journal of Vascular Surgery, vol. 2, No. 3, p. 424-429.

Kesler, et al., Enhanced Strength of Endothelial Attachment on Polyester Elastomer and Polytetrafluoroethylene Graft Surfaces with Fibronectin Substrate, Journal of Vascular Surgery, vol. 3, No. 1, p. 58-64, Jan. 1986.

Knighton, et al, Classification and Treatment of Chronic Nonhealing Wounds, Ann. Surg., vol. 204, No. 3, p. 322-330, Sep. 1986.

Knighton, et al., The Use of Platelet Derived Wound Healing Formula in Human Clinical Trials, p. 319-329, 1988.

Knighton, et al., Regulation of Cutaneous Wound Healing by Growth Factors, Clinical Materials, vol. 8, Nos. 3 & 4, p. 229-241, 1991.

Knöbl, et al., The Protein C System in Patients Undergoing Cardiopulmonary Bypass, Journal of Thoracic and Cardiovascular Surgery, vol. 94, No. 4, p. 600-605, Oct. 1987.

Kovacs, et al., Bioplast Fibrin Coagulum in Large Cystic Defects of the Jaw, Int. J. Oral Surg., vol. 5, p. 111-116, 1976.

Köveker, Clinical Application of Fibrin Glue in Cardiovascular Surgery, Thorac. Cardiovasc. Surgeon 30, p. 228-229, 1982.

Köveker, et al., Clinical Experience with Fibrin Glue in Cardiac Surgery, Thorac. Cardiovasc. Surgeon 29, p. 287-289, 1981.

Köveker, et al., Reduction of Thrombogenicity in Small-diameter Vascular Prostheses Seeded with Autologous Endothelial Cells, Thorac. Cardiovasc. Surgeon 34, p. 49-51, 1986.

Kram, et al., Use of Concentrated Fibrinogen in Experimental Tracheal Repair, Journal of Biomedical Research, vol. 20, No. 5, p. 579-587, May/Jun. 1986.

Kram, et al., Fibrin Glue Sealing of Polytetrafluoroethylene Vascular Graft Anastomoses: Comparison with Oxidized Cellulose, Journal of Vascular Surgery, vol. 8, No. 5, p. 563-568, Nov. 1988.

Kram, et al., Antibacterial Effects of Fibrin Glue—Antibiotic Mixtures, Journal of Surgical Research, vol. 50, No. 2, p. 175-178, Feb. 1991.

Kratzat, et al., Klinische Efrahrungen mit dem Fibrin-Antibiotikum-Verbund bei Knochen-und Weichteilinfektionen, Akt. Chir., vol. 17, p. 58-62, 1982.

Kratzat, et al., Erste KlinischeErfahrungen mit dem Fibrin-Antibiotikum-Verbund bei der Osteomyelitis, Orthop. Praxis, p. 852-855, Oct. 1981.

Kreider, et al., Concordance of Condylomata Acuminata Responses to Treatment with Intralesional MPI 5003 and Papilloma Responses in the Shope Rabbit Papilloma Model System, 9th SPS Meeting Abstracts, p. 201-202.

Ksander, et al., The Effect of Platelet Relesate on Wound Healing in Animal Models, Journal of the American Academy of Dermatology, vol. 22, No. 5, Part 1, p. 781-791, May 1990.

Larson, et al., Efficacy of a Fibrin Hemostatic Bandage in Controlling Hemorrhage from Experimental Arterial Injuries, Archives of Surgery, vol. 130, p. 420-422, Apr. 1995.

Lasa, et al., Osteorgeneration Using a Fibrin Sealant Delivery Vehicle for Demineralized Bone Matrix.

Lasa, et al., Effect of Fibrin Glue and Opsite on Open Wounds in DB/DB Mice, Journal of Surgical Research, vol. 54, p. 202-206, Mar. 1993.

Lerner, et al., Current Research Review; Current Status of Surgical Adhesives, Journal of Surgical Research, vol. 48, p. 165-181, 1990.

Lindner, et al., Basic Fibroblast Growth Factor Stimulates Endothelial Regrowth and Proliferation in Denuded Arteries, J. Clin. Invest., vol. 85, p. 2004-2008, Jun. 1990.

Lobb, Clinical Applications of Heparin-Binding Growth Factors, European Journal of Clinical Investigation, vol. 18, p. 321-336, 1988.

Lucht, et al., Fibrin Sealant in Bone Transplantation, Acta. Orthop. Scand., vol. 57, p. 19-24, 1986.

Luyten, et al., Purification and Partial Amino Acid Sequence of Osteogenin, a Protein Initiating Bone Differentiation, Journal of Biological Chemistry, vol. 264, No. 23, p. 13377-13380, Aug. 15, 1989.

Lynch, et al., Growth Factors in Wound Healing, J. Clin. Invest., vol. 84, p. 649-646, Aug. 1989.

MacPhee, et al., Fibrin Sealant Based Bandages and Foam: Hemostatic Devices for Treatment of Combat Casualties on the Battlefield, Presented at the Advanced Technology Applications to Combat Casualty Care (ATACCC) Conference, p. 1, May 17-18, 1995.

MacPhee, et al., Field-Ready Fibrin Sealant Based Hemostatic Devices, Presented at the 29th Penner Blood Conference, p. 1, May 12, 1995.

MacPhee, et al., Fibrin Sealant Based Hemostatic Devices for Treatment of Trauma in the Field, Presented to the FDA-Army Conference on Fibrin Sealant, p. 1, Dec. 1994.

Mark, et al., Repair of Calvarial Nonunions by Osteogenin, a Bone-Inductive Protein, Plastic and Reconstructive Surgery, p. 623-630, Oct. 1990.

Massagué, The TGF-$\beta$ amily of Growth and Differentiation Factors, Cell, vol. 49, p. 437-438, May 22, 1987.

Matras, Fibrin Seal: The State of the Art, J. Oral. Maxillofac. Surg., 43:605-611, 1985.

McEvitt, Experiences with Fibrin Fixation Methods of Skin Grafting, Jour. MSMS, p. 1347-1351, Dec. 1945.

McGee, et al., Recombinant Basic Fibroblast Growth Factor Accelerates Wound Healing, Journal of Surgical Research, vol. 45, p. 145-153, 1988.

Michael, et al., The Use of Human Fibrogen in Reconstructive Surgery, Journal of the American Medical Association, vol. 123, No. 5, p. 279, Oct. 2, 1943.

Miller, et al., Basal Cell Carcinomas Histologically Resolved After Treatment with Intralesional 5-Fluorouracil Therapeutic Implant, Proceedings of the American Association for Cancer Research, vol. 32, p. 420, Mar. 1991.

Montesano, et al., Basic Fibroblast Growth Factor Induces Angiogenesis In Vitro, Proc. Nat. Acad. Sci. USA, vol. 83, p. 7297-7301, Oct. 1986.

Moore, et al., Coagulum Pelviolithotomy; An Improved Technique, The Journal of Urology, vol. 67, No. 5, p. 579-584, May 1952.

Moore, et al., Development of an Infection-Resistant Vascular Prosthesis, Arch. Surgery, vol. 116, p. 1403-1407, Nov. 1981.

Morrison, et al., Chemical, Clinical, and Immunological Studies on the Products of Human Plasma Fractionation, p. 573-575, Received for Publication Feb. 17, 1944.

Mustoe, et al., Accelerated Healing of Incisional Wounds in Rats Induced by Transforming Growth Factor—$\beta$ Science, vol. 237, p. 1333-1336, Sep. 11, 1987.

Nowotny, et al, Mechanical Properties of Fibrinogen-Adhesive Material, Biomaterials 1980, John Wiley & Sons, p. 677-682, 1982.

Orenberg, et al., The Effect of Intralesional 5-Flurorouracil Therapeutic Implant (MPI 5003) for Treatment of Basal Cell Carcinoma, Journal of the American Academy of Dermatology, vol. 27, No. 5, p. 723-728, Nov. 1992.

Petrelli, et al., The Application of Tissue Adhesives in Small Bowel Anastomoses, Journal of Surgical Oncology, vol. 19, p. 59-61, Jan. 1982.

Pierce, et al., In Vivo Incisional Wound Healing Augmented by Platelet-Derived Growth Factor and Recombinant c-sis Gene Homodimeric Proteins, Journal of Experimental Medicine, vol. 167, p. 974-987, Mar. 1988.

Pop, et al., Experimental Covering of the Dental Pulp in the Dog with Biological Substances, Stomatologia, vol. 16, No. 5, p. 397-406 (Rom), 1969.

Presta, et al., Basic Fibroblast Growth Factor Requires a Long-Lasting Activation of Protein Kinase C to Induce Cell Proliferation in Transformed Fetal Bovine Aortic Endothelial Cells, Cell Regulation, vol. 2, p. 719-726, 1991.

Puumala, et al., IntraventricularInfusion of HBGF-2 Promotes Cerebral Anggiogenesis in Wistar Rat, Brain Research, vol. 534, p. 283-286, 1990.

Radomski, et al., Initial Adherence of Human Capillary Endothelial Cells to Dacron, Journal of Surgical Research, vol. 42, No. 2, p. 133-140, Feb. 1987.

Ramalanjaona, et al., The Effect of Fibronectin Coating on Endothelial Cell Kinetics in Polytetrafluoroethylene Grafts, Journal of Vascular Surgery, vol. 3, No. 2, p. 264-, Feb. 1986.

Schlag, et al., In Vivtro Properties of Mixtures of Fibrin Seal and Antibiotics, Biomaterials, vol. 4, p. 29-32, Jan. 1983.

Roberts, et al., Transforming Growth Factor,☐ Advances in Cancer Research, vol. 51, p. 107-145.

Rothe, et al., Growth Factors, Arch. Dermatol., vol. 125, p. 1390-1398, Oct. 1989.

Rovee, Evolution of Wound Dressings and Their Effects on the Healing Process, Clinical Materials, p. 183-188, 1991.

Sakurai, et al., Controlled Release of Sisonicin from Fibrin Glue, Journal of Controlled Release, vol. 18, p. 39-44, 1992.

Sauvage, et al., Interspecies Healing of Porous Arterial Prostheses, Arch. Surg., vol. 109, p. 698-705, Nov. 1974.

Schlag, et al., Fibrin Sealant in Orthopedic Surgery, Clinical Orthopedics and Related Research, No. 227, p. 269-285, Feb. 1988.

Schrenk, et al., Fibrin Glue coating of e-PTFE Prostheses Enhances Seeding of Human Endothelial Cells, Thorac. Cardiovasc. Surgeon, vol. 35, p. 6-10, Oct. 3, 1986.

Schultz, et al., Epithelial Wound Healing Enhanced by Transforming Growth Factor-☐ nd Vaccinia Growth Factor, Science, vol. 235, p. 350-352.

Schwarz, et al., The Influence of Fibrin Sealant on Demineralized Bone Matrix-Dependent Osteoinduction, Clinical Orthopaedics and Related Research, vol. 238, p. 282-287, Jan. 1989.

Senderoff, et al., Fibrin Based Drug Delivery Systems, Journal of Parenteral Science and Technology, vol. 45, No. 1, Jan.-Feb. 1991.

Sheehan, Plasma Fixation of Skin Grafts, American Journal of Surgery, New Series vol. LXV, No. 1, p. 74-78, Jul. 1944.

Shindo, et al., Improved Patency of Collagen-Impregnated Grafts After In Vitro Autogenous Endothelial Cell Seeding, Journal of Vascular Surgery, vol. 6, No. 4, p. 325-332, Oct. 1987.

Shoemaker, et al., Effects of Fibrin Sealant on Incorporation of Autograft and Xenograft Tendons Within Bone Tunnels, American Journal of Sports Medicine, vol. 17, No. 3, p. 318-324, 1989.

Silbermann, In Vitro Systems for Inducers of Cartilage and Bone Development, Biomaterials, vol. 11, Biomat 89, p. 47-49, 1990.

Silberstein, et al., An Autologous Fibrinogen-Based Adhesive for Use in Otologic Surgery, Transfusion, vol. 28, No. 4, p. 319-321, 1988.

Spotnitz, et al., Fibrin Glue from Stored Human Plasma, The American Surgeon, vol. 53, No. 8, p. 460-462, Aug. 1987.

Sprugel, et al., The Effects of Different Growth Factors in Subcutaneous Wound Chambers, Alan R. Liss, Inc., p. 77-91, 1989.

Stark, et al., Experience with Fibrin Seal (Tisseel) in Operations for Congenital Heart Defects, The Annals of Thoracic Surgery, vol. 38, No. 4, p. 411-413, Oct. 1984.

Stemberger, et al., Fibrinogen-Fibrin Conversion and Inhibition of Fibrinolysis, Thorac. Cardiovasc. Surgeon, vol. 30, p. 209-214, 1982.

Sugie, et al., The Chemical Modification of Fibrin Film as Artificial Skin, Chemical Abstracts, vol. 85, p. 318, 1976.

Sugitachi, et al., A Newly Designed Anticancer Tumor Immunity Drug Delivery System, Trans. Am. Soc. Artif. Intern. Organs, vol. XXXVII, p. M177-M178, 1991.

Thompson, et al., Fibrin Glue: A Review of Its Preparation, Efficacy, and Adverse Effects as a Topical Hemostat, Drug Intelligence and Clinical Pharmacy, vol. 22, p. 946-952, Dec. 1988.

Thompson, et al., Site-Directed Neovessel Formation In Vivo, Science, vol. 241, p. 1349-1352, Sep. 9, 1988.

Thompson, et al., Heparin-Binding Growth Factor 1 Induces the Formation of organoid Neovascular Structures In Vivo, Proc. Natl. Acad. Sci. USA, vol. 86, p. 7928-7932, Oct. 1989.

Thorson, et al., The Role of the Tissue Adhesive Fibrin Seal (FS) in Esophageal Anastomoses, Journal of Surgical Oncology, vol. 24, No. 3, p. 221-223, Nov. 1983.

Tidrick, et al., Fibrin Fixation of Skin Transplants, Surgery, vol. 15, p. 90-95, Jan.-Jun. 1944.

Tsuboi, et al., Recombinant Basic Fibroblast Growth Factor Stimulates Wound Healing in Healing-impaired db/db Mice, J. Exp. Med., vol. 172, p. 245-251, Jul. 1990.

Ulatowski, et al., Neue Aspekte der Anwendung Eines Erweiterten Fibrinklebesystems (FKS), Orthop. Praxis, p. 795-799, Oct. 1979.

Urist, et al., Bone Formation in Implants of Partially and Wholly Demineralized Bone Matrix, Clinical Orthopaedics and Related Research, vol. 71, p. 271-278, Jul.-Aug. 1970.

Urist, et al., Bone Morphogenesis in Implants of Insoluble Bone Gelatin, Proc. Nat. Acad. Sci. USA, vol. 70, p. 3511-3315, 1975.

Walterbusch, et al., Clinical Experience with Fibrin Glue for Local Bleeding Control and Sealing of Vascular Prostheses, Thorac. Cardiovasc. Surgeon, vol. 30, p. 234-235, 1982.

Wang, et al., Bone Morphogenetic Proteins and Bone Repair, Wound Repair.

Watkins, et al., Adult Human Saphenous Vein Endothelial Cells: Assessment of Their Reproductive Capacity for Use in Endothellial Seeding of Vascular Prostheses, Journal of Surgical Research, vol. 36, p. 588-596, 1984.

Weiner, et al., Fibrin Foam and Thrombin as Used in the Surgical Removal of a Large Fibromyxoma of the Mandible, The Journal of the American Dental Association, vol. 33, No. 11, p. 731-735. Jun. 1, 1946.

Weisman, et al., Biochemical Characterization of Autologous Fibrinogen Adhesive, Laryngoscope, vol. 97, p. 1186-1190, Oct. 1987.

Williams, et al., Adult Human Endothelial Cell Compatibility, Journal of Surgical Research, vol. 38, p. 618-629, 1985.

Woodhall, Fibrin Foam as a Hemostatic Agent in Rehabilitation Neurosurgery, Journal of the American Medical Association, vol. 126, No. 8, p. 469-471, Oct. 21, 1944.

Yu, et al., Pharmacokinetics and Clinical Application of the Intralesional Methotrexate Therapeutic Implant, Proceedings of Asco., vol. 11, p. 100, Mar. 1992.

Yu, et al., Comparison of Antitumor Effects of Treatment Sequence of Fluorouracil (FU) and Cisplatin (Pt) Therapeutic Implants in a Mouse Tumor Model, Proceedings of Asco., vol. 11, p. 100, Mar. 1992.

Zilla, et al., Use of Fibrin Glue as a Substrate for In Vitro Endothelialization of PTFE Vascular Grafts, Surgery, vol. 105, No. 4, p. 515-522, Apr. 1989.

Zilch, et al., The Sustained Release of Cefotaxim From a Fibrin-Cefotaxim Compound in Treatment of Osteitis, Arch. Orthop. Trauma Surg., vol. 106, p. 36-41, 1986.

World Patents Index English Translation of title and abstract of Japanese Patent Application JP54-104687, Unitika, Protective Materials for Wounds—Comprises a Fibre Block, Film or Sponge Contg., Aug. 17, 1979.

World Patents Index English Translation of title and abstract of German patent application No. DE 3,037,270, Ulatowski, Fibrin-Antibiotic Composite Chain—For Use as an Antiseptic Implant, May 19, 1982.

World Patents Index English Translation of title and abstract of Japanese patent application No. JP-60204725, Immuno, Tissue Adhesive—Comprises Fibrinogen, Plasmin Inhibitor and Antibiotics.

English Translation of JP 62-246370, translated by Translation Services PTY Ltd, translation dated Mar. 6, 2001, Shiotani, et al., Wound Dressing, Patent Gazette (JP), p. 1-8, Oct. 27, 1987.

English Translation of JP 63-115564, translated by Translation Services PTY Ltd, translation dated Mar. 13, 2001, Shiotani, et al., Wound Dressing Material, Patent Gazette (JP), p. 1-6, May 20, 1988.

Afra, et al., English translation of the first full paragraph at p. 28 of: Experimentelle Untersuchung der Resorption von Fibrinfilmen und ihrer anwendung in der neurochirurgischen Praxis, Acta. Med. Acad. Sci. Hung., vol. 11, p. 1-29, 1958.

Áfra, et al., Experimentelle Untersuchung Der Resorption Von Fibrinfilmen Und Ihre Anwendung in der Neurochirurgischen Praxis, Acta Medica Hung., p. 1-29.

Bagdy, et al., English translation of the second, third, fourth, and fifth paragraphs at p. 852 of: Experimentelle und Klinische Anwendung der aus Rinderplasma hergestellten Fibrinprodukte, Zentralblatt fur Chirurgie, vol. 77, p. 848-852, 1952.

Bagdy, et al., Experimentelle und Klinische Anwendung der aus Rinderplasma Hergestellten Fibrinprodukte, Zentralblatt fur Chirurgie, vol. 77, p. 848-852, 1952.

Bagdy, et al., English translation of the fourth, fifth, and sixth paragraphs at p. 152 of: Trombin-Fibrinprodukte und Ihre Therapeutische Anwendung, Veb Gustav Fischer Verlag Jena, p. 152-159, 1963; and Badgy, et al., English translation of the sixth paragraphs at p. 184 of: Trombin-Fibrinprodukte und Ihre Therapeutische Anwendung, Veb Gustav Fischer Verlag Jena, p. 184-187, 1963.

Bagdy, et al., Trombin-Fibrinprodukte und Ihre Therapeutische Anwendung, Veb Gustav Fischer Verlag Jena, p. 152-159, 163; and Bagdy, et al., Trombin-Fibrinprodukte und Ihre Therapeutische Anwendung, Veb Gustav Fischer Verlag Jena, p. 184-187, 1963.

István, et al., English translation of first full column at p. 219 of: Gastrointestinalis Vérzések Csillapitása thrombin-Fibrin Készitmémyel, Orv. Hetil., vol. 105, p. 219-223, 1964.

Stoll, et al., English translation of the third, fourth and fifth paragraphs at p. 615, Koagulum-Pyelolithotomie, Zeitschrift für Urologie, vol. 52, p. 610-615, 1959.

Stoll, et al., Koagulum-Pyelolithotomie, Zeitschrift für Urologie, vol. 52, p. 610-615, 1959.

Winter, et al., English translation of the fourth, fifth, sixth, seventh and eighth paragraphs at p. 479 of: Experimentelle und Klinische Anwendung der und Rinderplasma hergestellten Fibrinprodukte. III. Klinische Verwendung von Hämostischen Fibrinprodukten, Zentralblatt für Chirurgie, vol. 78, p. 469-479, 1953.

Winter, et al., Experimentelle und Klinische Anwendung der aus Rinderplasma hergestellten Fibrinprodukte. III. Klinische Verwendung von hämostischen Fibrinprodukten, Zentralblatt für Chirurgie, vol. 78, p. 469-479, 1953.

Ulatowski, et al., Zur Wirkung eines Fibrin-Antibiotikum-Verbundes bei Knochen- und Wiechteil-Infektionen, Retchler, Moderne Arzneimittel fur den Forschriff der Medizin, p. 1-4.

Ulatowski, et al., Pharmakokinetik eines Fibrinantibiotikumverbundes, Literatur, p. 196-199.

Redl, et al., Fibrinkleber-Antibiotika-Gemische—Festigkeit und Elutionsverhalten, Literatur, p. 178-181.

Kratzat, et al., Klinische Erfahrungen mit dem Fibrin-Antibiotikum-Verbund bei Knochen- und Weichteilinfektionen, Kasuistik, p. 200-204.

Zilch, et al., Diffusionsverhalten von Cefotaxim aus der Fibrin-Antibiotika-Plombe im Tierversuch, Literatur, p. 191-195.

Ingraham, et al., Studies on Fibrin Foam as a Hemostatic Agent in Neurosurgery, with Special Reference to its Comparison with Muscle, Journal of Neurosurgery, vol. 1, p. 171-181, 1944.

Jackson, et al., Hemostatic efficacy of a fibrin sealant-based topical agent in a femoral artery injury model: a randomized, blinded, placebo-controlled study, Journal of vascular surgery, p. 274-280, Aug. 26, 1997.

Seegers et al, Preparation and Properties of Thrombin, Arch Biochem Biophys 128:194-201, 1968.

Mihalyi, et al, Changes in pH Associated with Clotting of Fibrinogen. Kinetic Studies of Shift and Correlation of the pH Change with the Release of Fibrinopeptides and the Ensuing Polymerization Biochemistry 30:4753-4762, 1991.

Doolittle, Characterization of Lamprey Fibrinopeptides, Biochem J 94: 742, 1965.

Protein Purification by Reversed Phase-HPLC, Available at: (http://www.molecularinfor.com/MTM/G/G3/G3-1/G3-1-7.html) (Last Accessed Jun. 24, 2008).

MacPhee, M & Wilmer, K, Tissue Sealants Available Today, in Tissue Glues in Cosmetic Surgery. Renato Saltz & Dean M. Toriumi, Eds. Quality Medical Publishing, Inc. 2004.

"The effects of neutral salts on the structure and conformational stability of macromolecules in solution", in Structure and Stability of Biological Macromolecules, Timasheff and Fasman (eds), vol. 2, Marcel Dekker, New York, p. 417-574.

Busby et al, Thermal Denaturation of Antithrombin, J Biol Chem 256:12140-12147, 1981.

International Searching Authority, International Search Report for related International Application No. PCT/US07/17473, mailed Aug. 5, 2008, p. 1-6.

International Searching Authority, International Search Report for related International Application No. PCT/US07/17474, mailed Jul. 24, 2008, p. 1-4.

International Searching Authority, International Search Report for related International Application No. PCT/US07/17475, mailed Jul. 24, 2008, p. 1-4.

Gorsky, V.A. et al., "Methods of Effecting Additional Hemostasis During Liver and Biliary Surgical Procedures", Aug. 3, 2005, 12 pages.

STB Lifesaving Technologies, STB FAST Dressing U.S. Appl. No. 11/882,872 re: Stroetmann US Patent #4,442,655, Prepared for USPTO Dec. 14, 2010.

Bijan S. Kheirabadi et al., "Clot-Inducing Minerals Versus Plasma Protein Dressing for Topical Treatment of External Bleeding in the Presence of Coagulopathy", The Journal of TRAUMA Injury, Infection, and Critical Care, vol. 69, No. 5, Nov. 2010, pp. 1062-1071.

STB Lifesaving Technologies, "Evaluation and Comparison of STB Dressings and Dressings Manufactured According to Stroetmann Patent #4,442,655", Stroetmann Patent Evaluation, Oct. 2010, pp. 1-16.

STB Lifesaving Technologies, "Evaluation and Comparison of STB Dressings and Dressings Manufactured According to American Red Cross Patent #6,762,336", Functional Comparison of STB & ARC Dressings, Nov. 3, 2010, pp. 1-17.

* cited by examiner

FIGURE 1. HUMAN CLOTTING CASCADE

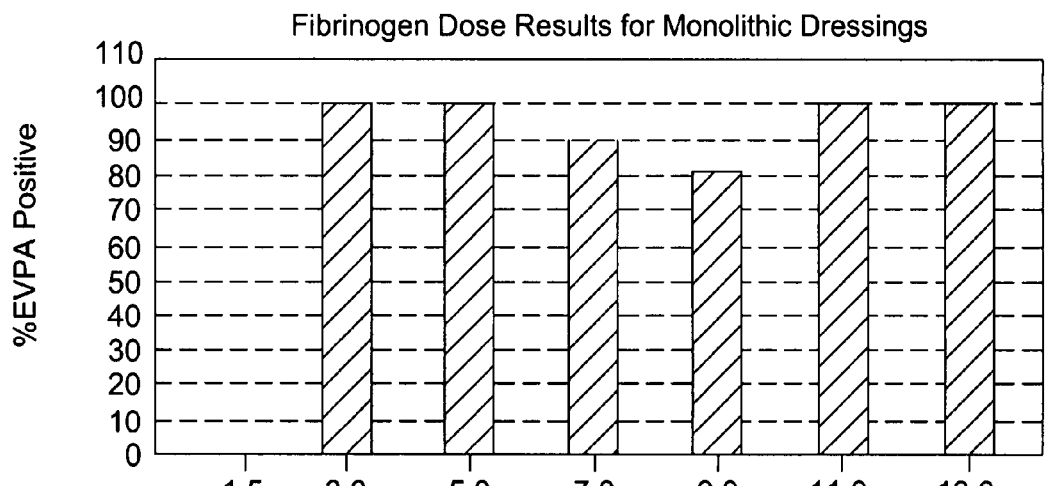
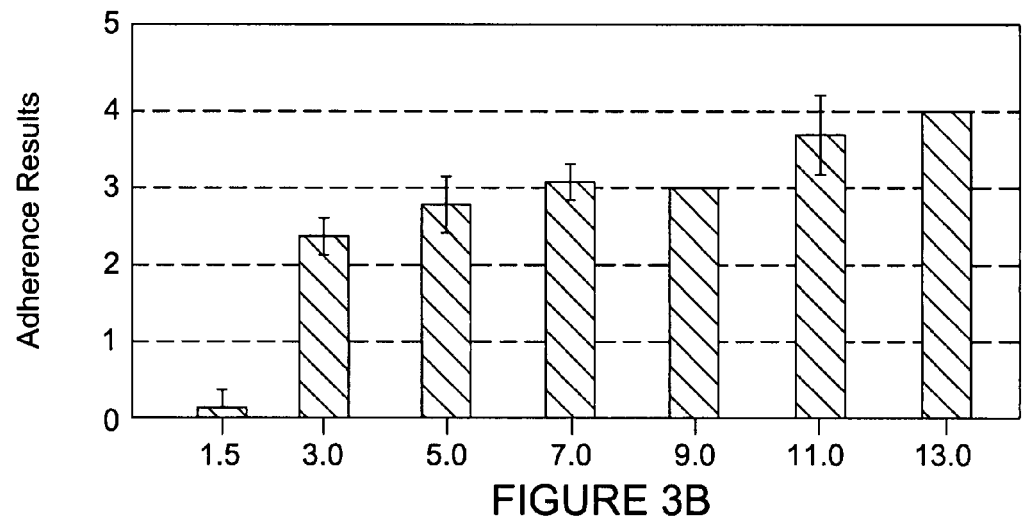
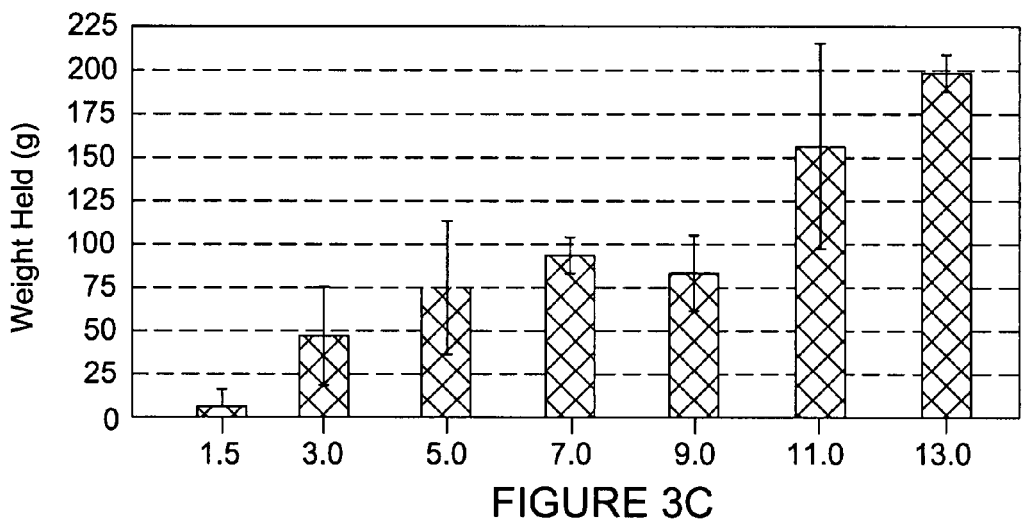
FIGURE 3A
FIGURE 3B
FIGURE 3C

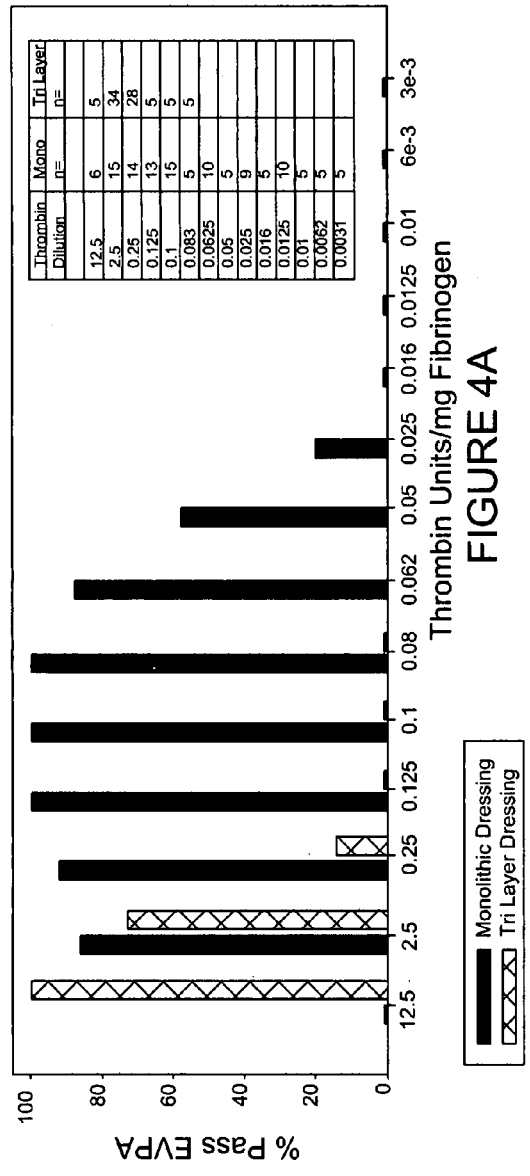
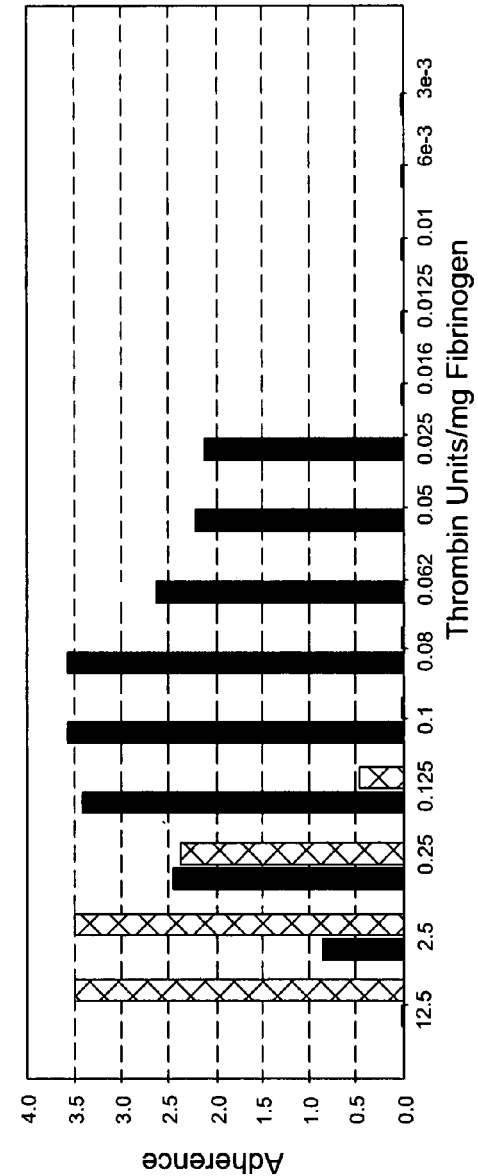

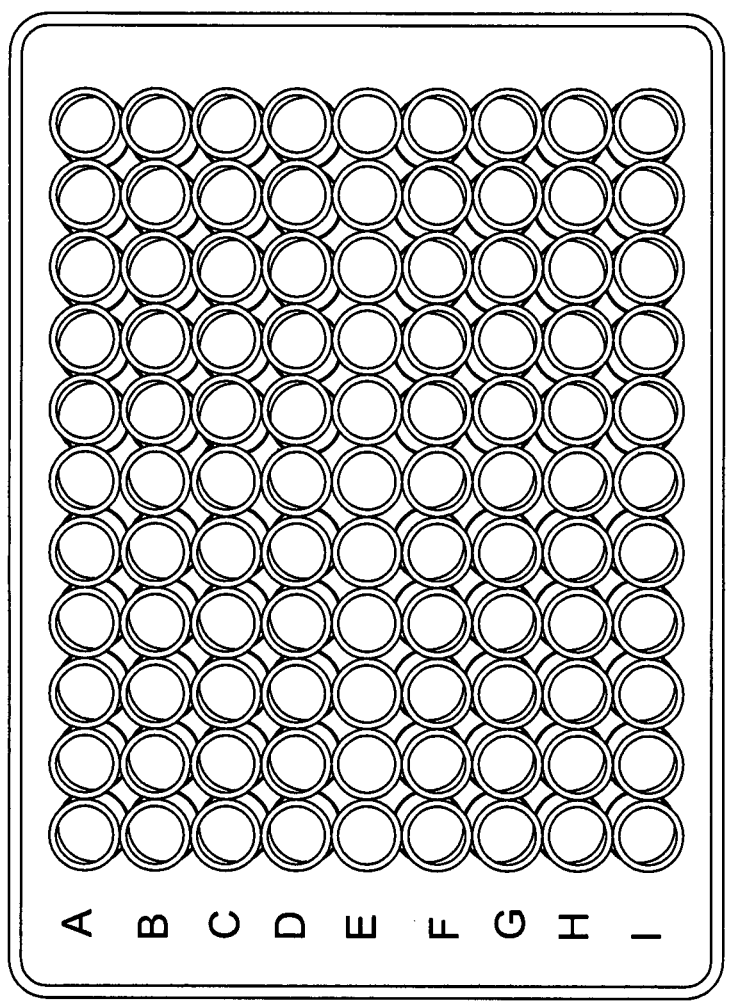

PROCESSES FOR THE PRODUCTION OF SOLID DRESSINGS FOR TREATING WOUNDED TISSUE

FIELD OF THE INVENTION

The present invention relates to processes for producing solid dressings for treating wounded tissue in a mammalian patient, such as a human, and to the dressings and intermediates produced thereby.

BACKGROUND OF THE INVENTION

The materials and methods available to stop bleeding in pre-hospital care (gauze dressings, direct pressure, and tourniquets) have, unfortunately, not changed significantly in the past 2000 years. See L. Zimmerman et al., Great Ideas in the History of Surgery (San Francisco, Calif.: Norman Publishing; 1993), 31. Even in trained hands they are not uniformly effective, and the occurrence of excessive bleeding or fatal hemorrhage from an accessible site is not uncommon. See J. M. Rocko et al., J. Trauma 22:635 (1982).

Mortality data from Vietnam indicates that 10% of combat deaths were due to uncontrolled extremity hemorrhage. See SAS/STAT Users Guide, 4th ed. (Cary, N.C.: SAS Institute Inc; 1990). Up to one third of the deaths from ex-sanguination during the Vietnam War could have been prevented by the use of effective field hemorrhage control methods. See SAS/STAT Users Guide, 4th ed. (Cary, N.C.: SAS Institute Inc; 1990).

Although civilian trauma mortality statistics do not provide exact numbers for pre-hospital deaths from extremity hemorrhage, case and anecdotal reports indicate similar occurrences. See J. M. Rocko et al. These data suggest that a substantial increase in survival can be affected by the pre-hospital use of a simple and effective method of hemorrhage control.

There are now in use a number of newer haemostatic agents that have been developed to overcome the deficiencies of traditional gauze bandages. These haemostatic agents include the following:

Microporous polysaccharide particles (TraumaDEX®, Medafor Inc., Minneapolis, Minn.);
Zeolite (QuikClot®, Z-Medica Corp, Wallington, Conn.);
Acetylated poly-N-acetyl glucosamine (Rapid Deployment Hemostat™ (RDH), Marine Polymer Technologies, Danvers, Mass.);
Chitosan (HemCon® bandage, HemCon Medical Technologies inc., Portland Oreg.);
Liquid Fibrin Sealants (Tisseel VH, Baxter, Deerfield, Ill.)
Human fibrinogen and thrombin on equine collagen (TachoComb-S, Hafslund Nycomed Pharma, Linz, Austria);
Microdispersed oxidized cellulose (M•Doc™, Alltracel Group, Dublin, Ireland);
Propyl gallate (Hemostatin™, Analytical Control Systems Inc., Fishers, Ind.);
Epsilon aminocaproic acid and thrombin (Hemarrest™ patch, Clarion Pharmaceuticals, Inc);
Purified bovine corium collagen (Avitene® sheets (non-woven web or Avitene Microfibrillar Collagen Hemostat (MCH), Davol, Inc., Cranston, R.I.);
Controlled oxidation of regenerated cellulose (Surgicel®, Ethicon Inc., Somerville, N.J.);
Aluminum sulfate with an ethyl cellulose coating (Sorbastace Microcaps, Hemostace, LLC, New Orleans, La.);
Microporous hydrogel-forming polyacrylamide (BioHemostat, Hemodyne, Inc., Richmond Va.); and
Recombinant activated factor VII (NovoSeven®, NovoNordisk Inc., Princeton, N.J.).

These agents have met with varying degrees of success when used in animal models of traumatic injuries and/or in the field.

One such agent is a starch-based haemostatic agent sold under the trade name TraumaDEX™. This product comprises microporous polysaccharide particles that are poured directly into or onto a wound. The particles appear to exert their haemostatic effect by absorbing water from the blood and plasma in the wound, resulting in the accumulation and concentration of clotting factors and platelets. In two studies of a lethal groin wound model, however, this agent showed no meaningful benefit over standard gauze dressings. See McManus et al., Business Briefing: Emergency Medical Review 2005, pp. 76-79 (presently available on-line at www.touchbriefings.com/pdf/1334/Wedmore.pdf).

Another particle-based agent is QuickClot™ powder, a zeolite granular haemostatic agent that is poured directly into or onto a wound. The zeolite particles also appear to exert their haemostatic effect through fluid absorption, which cause the accumulation and concentration of clotting factors and platelets. Although this agent has been used successfully in some animal studies, there remains concern about the exothermic process of fluid absorption by the particles. Some studies have shown this reaction to produce temperatures in excess of 143° C. in vitro and in excess of 50° C. in vivo, which is severe enough to cause third-degree burns. See McManus et al., Business Briefing: Emergency Medical Review 2005, at 77. The exothermic reaction of QuikClot™ has also been observed to result in gross and histological tissue changes of unknown clinical significance. Acheson et al., J. Trauma 59:865-874 (2005).

Unlike these particle-based agents, the Rapid Deployment Hemostat™ appears to exert its haemostatic effect through red blood cell aggregation, platelet activation, clotting cascade activation and local vasoconstriction. The Rapid Deployment Hemostat™ is an algae-derived dressing composed of poly-N-acetyl-glucosamine. While the original dressing design was effective in reducing minor bleeding, it was necessary to add gauze backing in order to reduce blood loss in swine models of aortic and liver injury. See McManus et al., Business Briefing: Emergency Medical Review 2005, at 78.

Another poly-N-acetyl-glucosamine-derived dressing is the HemCon™ Chitosan Bandage, which is a freeze-dried chitosan dressing purportedly designed to optimize the mucoadhesive surface density and structural integrity of the chitosan at the site of the wound. The HemCon™ Chitosan Bandage apparently exerts its haemostatic effects primarily through adhesion to the wound, although there is evidence suggesting it may also enhance platelet function and incorporate red blood cells into the clot it forms on the wound. This bandage has shown improved hemostasis and reduced blood loss in several animal models of arterial hemorrhage, but a marked variability was observed between bandages, including the failure of some due to inadequate adherence to the wound. See McManus et al., Business Briefing: Emergency Medical Review 2005, at 79.

Liquid fibrin sealants, such as Tisseel VH, have been used for years as an operating room adjunct for hemorrhage control. See J. L. Garza et al., J. Trauma 30:512-513 (1990); H. B. Kram et al., J. Trauma 30:97-101 (1990); M. G. Ochsner et al., J. Trauma 30:884-887 (1990); T. L. Matthew et al., Ann. Thorac. Surg. 50:40-44 (1990); H. Jakob et al., J. Vasc. Surg., 1:171-180 (1984). The first mention of tissue glue used for hemostasis dates back to 1909. See Current Trends in Surgical Tissue Adhesives: Proceedings of the First International Symposium on Surgical Adhesives, M. J. MacPhee et al., eds. (Lancaster, Pa.: Technomic Publishing Co; 1995). Liquid fibrin sealants are typically composed of fibrinogen and thrombin, but may also contain Factor XIII/XIIIa, either as a by-product of fibrinogen purification or as an added ingredient (in certain applications, it is therefore not necessary that Factor XIII/Factor XIIIa be present in the fibrin sealant because there is sufficient Factor XIII/XIIIa, or other transaminase, endogenously present to induce fibrin formation). As liquids, however, these fibrin sealants have not proved useful for treating traumatic injuries in the field.

Dry fibrinogen-thrombin dressings having a collagen support (e.g. TachoComb™, TachoComb™ H and TachoSil available from Hafslund Nycomed Pharma, Linz, Austria) are also available for operating room use in many European countries. See U. Schiele et al., Clin. Materials 9:169-177 (1992). While these fibrinogen-thrombin dressings do not require the pre-mixing needed by liquid fibrin sealants, their utility for field applications is limited by a requirement for storage at 4° C. and the necessity for pre-wetting with saline solution prior to application to the wound. These dressings are also not effective against high pressure, high volume bleeding. See Sondeen et al., J. Trauma 54:280-285 (2003).

A dry fibrinogen/thrombin dressing for treating wounded tissue is also available from the American Red Cross (ARC). As disclosed in U.S. Pat. No. 6,762,336, this particular dressing is composed of a backing material and a plurality of layers, the outer two of which contain fibrinogen (but no thrombin) while the inner layer contains thrombin and calcium chloride (but no fibrinogen). While this dressing has shown great success in several animal models of hemorrhage, the bandage is fragile, inflexible, and has a tendency to break apart when handled. See McManus et al., Business Briefing: Emergency Medical Review 2005, at 78; Kheirabadi et al., J. Trauma 59:25-35 (2005).

Other fibrinogen/thrombin-based dressings have also been proposed. For example, U.S. Pat. No. 4,683,142 discloses a resorptive sheet material for closing and healing wounds which consists of a glycoprotein matrix, such as collagen, containing coagulation proteins, such as fibrinogen and thrombin. U.S. Pat. No. 5,702,715 discloses a reinforced biological sealant composed of separate layers of fibrinogen and thrombin, at least one of which also contains a reinforcement filler such as PEG, PVP, BSA, mannitol, FICOLL, dextran, myo-inositol or sodium chlorate. U.S. Pat. No. 6,056,970 discloses dressings composed of a bioabsorbable polymer, such as hyaluronic acid or carboxymethylcellulose, and a haemostatic composition composed of powdered thrombin and/or powdered fibrinogen. U.S. Pat. No. 7,189,410 discloses a bandage composed of a backing material having thereon: (i) particles of fibrinogen; (ii) particles of thrombin; and (iii) calcium chloride. U.S. Patent Application Publication No. US 2006/0155234 A1 discloses a dressing composed of a backing material and a plurality of fibrinogen layers which have discrete areas of thrombin between them. To date, none of these dressings have been approved for use or are available commercially.

In addition, past efforts to prepare fibrinogen/thrombin solid dressings have always been hampered by the very property that makes them desirable ingredients for treating wounds—their inherent ability to rapidly react under aqueous conditions to form fibrin. The presence of Factor XIII results in the mixture results in further conversion of fibrin Ia into cross-linked fibrin II.

The overall coagulation process for a human is shown in FIG. 1. As depicted therein, the conversion of fibrinogen into fibrin I involves the cleavage of two small peptides (A and B) from the alpha ($\alpha$) and beta ($\beta$) chains of fibrinogen respectively. These small peptides are difficult to detect and monitor directly; the decrease in the molecular weight of the alpha and beta chains, however, resulting from this cleavage can be monitored by gel electrophoresis. Similarly, the conversion of fibrin I to cross-linked fibrin II can be followed by the disappearance on gels of the gamma ($\gamma$) chain monomer of fibrinogen (as it is converted into $\gamma$-$\gamma$ dimers by the action of Factor XIII upon the $\gamma$ chain monomers).

To avoid premature reaction, previous attempts to manufacture fibrinogen/thrombin solid dressings have emphasized the separation of the fibrinogen and thrombin components as much as possible in order to prevent them from forming too much fibrin prior to use of the dressing. For example, the fibrinogen-thrombin dressings having a collagen support (e.g. TachoComb™, TachoComb™ H and TachoSil) available from Hafslund Nycomed Pharma are prepared by suspending particles of fibrinogen and thrombin in a non-aqueous liquid and then spraying the suspension onto the collagen base. The use of a non-aqueous environment, as opposed to an aqueous one, is intended to prevent excessive interaction between the fibrinogen and thrombin.

Alternatives to this process have been proposed, each similarly designed to maintain the fibrinogen and thrombin as separately as possible. For example, the fibrinogen/thrombin solid dressing disclosed in U.S. Pat. No. 7,189,410 was prepared by mixing powdered fibrinogen and powdered thrombin in the absence of any solvent and then applying the dry powder mixture to the adhesive side of a backing material. The fibrinogen/thrombin solid dressings disclosed in U.S. Pat. No. 6,762,336 and U.S. Patent Application Publication No. US 2006/0155234 A1 contain separate and discrete layers of fibrinogen or thrombin, each substantially free of the other. These approaches, however, have not been completely successful.

In order to function properly, a fibrinogen/thrombin-based solid dressing must meet several criteria. To begin with, the fibrinogen and thrombin must be able to successfully interact to form a clot and the more this clot adheres to the wound, the better the dressing performs. Grossly, the dressing must have a high degree of integrity, as the loss of active ingredients due to cracking, flaking and the like will ultimately result in decreased performance and meet with poor user acceptance. There have been reports that known fibrinogen/thrombin solid dressings are deficient in one or more of these characteristics.

Furthermore, the dressing must be homogenous, as all areas of the dressing must function equally well in order to assure its successful use. The dressing must also hydrate rapidly and without significant or special efforts. Relatively flat dressings are generally preferred, with curling or irregular, non-planar structures to be avoided if possible (these ten to interfere with effective application and, in some instances, may result in poor performance). Flexibility is another characteristic that is greatly preferred, both to improve performance and to increase the number of wound geometries and locations that can be treated effectively. Although known fibrinogen/thrombin solid dressings may be flexible when hydrated, they do not possess sufficient moisture content prior to hydration to be flexible. See, e.g., Sondeen et al., J. Trauma 54:280-285 (2003); Holcomb et al: J. Trauma, 55 518-526; McManus & Wedmore, Emergency Medicine Review, pp 76-79, 2005.

The amount of fibrin present in the dressing prior to use, particularly insoluble, cross-linked fibrin II, must be relatively small. This latter characteristic is important for several reasons. First, the presence of insoluble fibrin during manufacture normally results in poor quality dressings, which can exhibit decreased integrity, lack of homogeneity and difficult/slow hydration. These consequences can usually be detected visually by one of skill in the art.

For example, the presence of pre-formed fibrin in a fibrinogen/thrombin-based solid dressing can be detected visually by deviations from a homogenous surface appearance. In particular, a rough or lumpy appearance frequently signals that there are significant masses of fibrin that have formed during manufacture and will likely impede future performance. Solid, smooth and glossy "sheets" on the surface of solid dressings are also signs of fibrin that will tend to slow (or even block) hydration during use. Excessive curling-up of a solid dressing is another sign that a significant amount of fibrin has formed during manufacture. Upon addition of water or an aqueous solution, dressings with excessive fibrin content are slow to hydrate and often require forceful application of the liquid, sometimes with mechanical penetration of the surface, in order to initiate hydration. Moreover, once hydrated, dressings with a significant amount of pre-formed fibrin usually have a mottled and distinctly non-homogenous appearance.

The amount of pre-formed fibrin can also be assessed by various biochemical assays, such as the method described in U.S. Patent Application Publication No. US 2006/0155234 A1. According to this assay, the conversion of the fibrinogen γ chains to cross-linked γ-γ dimers is used as an indication of the presence of fibrin (the proportion of γ chain that is converted to γ-γ dimer being a measure of the amount of fibrin produced).

Other assays could assess changes in the other component chains of fibrinogen, such as the conversion of the Aα chain into free α chain and fibrinopeptide A or the conversion of the Bβ chain into free β chain and fibrinopeptide B. These changes can be monitored by gel electrophoresis in a similar manner to the γ to γ-γ conversion described in U.S. Patent Application Publication No. US 2006/0155234 A1. Interestingly, in U.S. Patent Application Publication No. US 2006/0155234 A1, relatively high levels of γ-γ dimerization (up to 10%) were reported, indicating that these dressings included substantial amounts of fibrin prior to use. This observation may account for the delamination and/or cracking observed in some of these dressings.

For a properly functioning fibrinogen/thrombin-based solid dressing, hydration should normally be completed within a few seconds and require nothing more than applying water (or some aqueous solution) onto the dressing. This solution could be blood or another bodily fluid from an injury site that the dressing is applied to, or it may be from some external source, such as a saline or other physiologically acceptable aqueous liquid applied to the dressing while it is on the wound to be treated. Longer hydration times, i.e. generally greater than 5 seconds, will impede the dressing's performance as portions of the dressing may be lost or shed into the fluids which will continue to freely flow prior to formation of sufficient cross-linked fibrin. Given the potentially fatal consequences of continued bleeding, any delay in dressing hydration during use is highly undesirable. In addition, the performance of dressings with excessive fibrin content are usually poor, as reflected by decreased scores in the EVPA and Adherence assays described herein, as well as during in vivo tests and clinical use.

Accordingly, there remains a need in the art for a solid dressing that can be used to treat wounded tissue, particularly wounded tissue resulting from traumatic injury in the field.

SUMMARY OF THE INVENTION

It is therefore an object of the present invention to provide processes for the production of solid dressings that can treat wounded mammalian tissue, particularly wounded tissue resulting from a traumatic injury. It is further an object of the present invention to provide solid dressings for treating wounded mammalian tissue, particularly human tissue, and intermediates useful in the manufacture of such dressings. Other objects, features and advantages of the present invention will be set forth in the detailed description of preferred embodiments that follows, and will in part be apparent from that description and/or may be learned by practice of the present invention. These objects and advantages will be realized and attained by the methods and compositions described in this specification and particularly pointed out in the claims that follow.

In accordance with these and other objects, a first embodiment of the present invention is direct to a process for producing a solid dressing for treating wounded tissue in a mammal comprising: (a) forming a liquid aqueous mixture of a fibrinogen component and a fibrinogen activator at a temperature sufficiently low to inhibit activation of the fibrinogen component by the fibrinogen activator; (b) reducing the temperature of the aqueous mixture to form a frozen aqueous mixture; and (c) reducing the moisture content of the frozen aqueous mixture to produce a solid dressing having a haemostatic layer consisting essentially of the fibrinogen component and the fibrinogen activator.

Other embodiments of the invention are directed to solid dressings produced by this process and intermediates produced during this process.

It is to be understood that the foregoing general description and the following detailed description of preferred embodiments are exemplary and explanatory only and are intended to provide further explanation, but not limitation, of the invention as claimed herein.

BRIEF DESCRIPTION OF DRAWINGS

FIGS. 3A-3C are graphs showing the results achieved in Example 1.

FIG. 4A and FIG. 4B are graphs depicting the results of the EVPA and Adherence Assays for the dressings made in Examples 6 to 12.

FIGS. 6A-6D and 7A-7B show the results achieved in Example 20, 21 and 22.

DETAILED DESCRIPTION OF PREFERRED EMBODIMENTS

Figure 1:
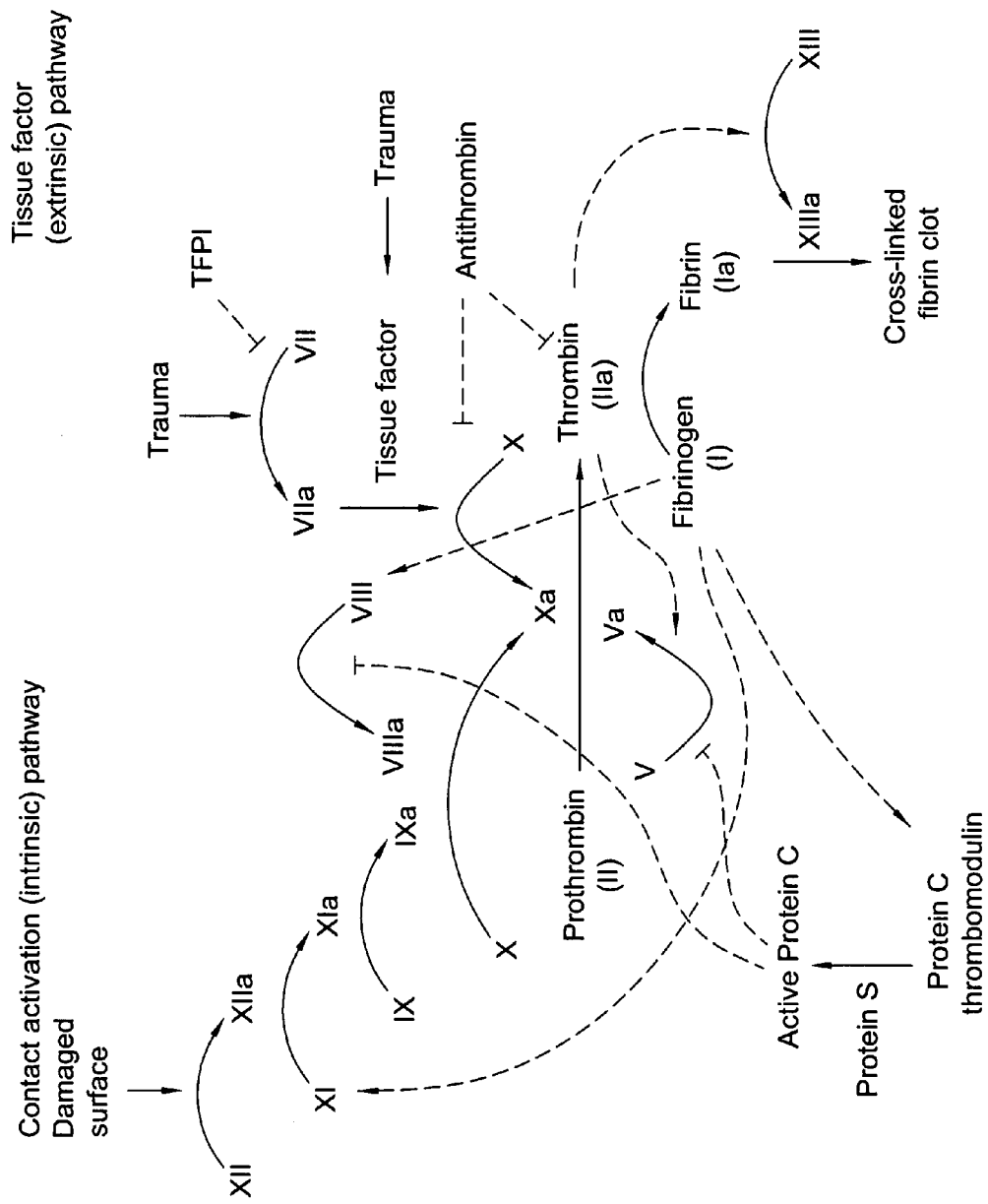
FIG. 1 is an overview of the human clotting cascade as provided by ERL's website (http://www.enzymeresearch.co.uk/coag.htm).

Unless defined otherwise, all technical and scientific terms used herein have the same meaning as is commonly understood by one of skill in the art to which this invention belongs. All patents and publications mentioned herein are incorporated by reference.

As used herein, use of a singular article such as "a," "an," and "the" is not intended to excluded pluralities of the article's object unless the context clearly and unambiguously dictates otherwise.

"Patient" as used herein refers to human or animal individuals in need of medical care and/or treatment.

"Wound" as used herein refers to any damage to any tissue of a patient which results in the loss of blood from the circulatory system and/or any other fluid from the patient's body. The tissue may be an internal tissue, such as an organ or blood vessel, or an external tissue, such as the skin. The loss of blood may be internal, such as from a ruptured organ, or external, such as from a laceration. A wound may be in a soft tissue, such as an organ, or in hard tissue, such as bone. The damage may have been caused by any agent or source, including traumatic injury, infection or surgical intervention.

"Resorbable material" as used herein refers to a material that is broken down spontaneously in and/or by the mammalian body into components which are consumed or eliminated in such a manner as not to interfere significantly with wound healing and/or tissue regeneration, and without causing any significant metabolic disturbance.

"Stability" as used herein refers to the retention of those characteristics of a material that determine activity and/or function.

"Suitable" as used herein is intended to mean that a material does not adversely affect the stability of the dressings or any component thereof.

"Binding agent" as used herein refers to a compound or mixture of compounds that improves the adherence and/or cohesion of the components of the haemostatic layer(s) of the dressings.

"Solubilizing agent" as used herein refers to a compound or mixture of compounds that improves the dissolution of a protein or proteins in aqueous solvent.

"Filler" as used herein refers to a compound or mixture of compounds that provide bulk and/or porosity to the haemostatic layer(s) of a dressing.

"Release agent" as used herein refers to a compound or mixture of compounds that facilitates removal of a dressing from a manufacturing mold.

"Foaming agent" as used herein refers to a compound or mixture of compounds that produces gas when hydrated under suitable conditions.

"Solid" as used herein is intended to mean that the dressing will not substantially change in shape or form when placed on a rigid surface, wound-facing side down, and then left to stand at room temperature for 24 hours.

"Frozen" as used herein is intended to mean that the composition will not substantially change in shape or form when placed on a rigid surface, wound-facing side down, and then left to stand at $-40°$ C. for 24 hours, but will substantially change in shape or form when placed on a rigid surface, wound-facing side down, and then left at room temperature for 24 hours. Thus, in the context of the present invention, a "solid" dressing is not "frozen" and a "frozen" composition or mixture is not "solid".

A first preferred embodiment of the present invention is directed to a process for producing a solid dressing for treating wounded tissue in a mammal comprising: (a) forming a liquid aqueous mixture of a fibrinogen component and a fibrinogen activator at a temperature sufficiently low to inhibit activation of the fibrinogen component by the fibrinogen activator; (b) reducing the temperature of the aqueous mixture to form a frozen aqueous mixture; and (c) reducing the moisture content of the frozen aqueous mixture to produce a solid dressing having a haemostatic layer consisting essentially of the fibrinogen component and the fibrinogen activator.

As used herein, "consisting essentially of" is intended to mean that the fibrinogen component and the fibrinogen activator are the only necessary and essential ingredients of the haemostatic layer(s) of the solid dressing when it is used as intended to treat wounded tissue. Accordingly, the haemostatic layer may contain other ingredients in addition to the fibrinogen component and the fibrinogen activator as desired for a particular application, but these other ingredients are not required for the solid dressing to function as intended under normal conditions, i.e. these other ingredients are not necessary for the fibrinogen component and fibrinogen activator to react and form enough fibrin to reduce the flow of blood and/or fluid from normal wounded tissue when that dressing is applied to that tissue under the intended conditions of use. If, however, the conditions of use in a particular situation are not normal, for example the patient is a hemophiliac suffering from Factor XIII deficiency, then the appropriate additional components, such as Factor XIII/XIIIa or some other transaminase, may be added to the haemostatic layer(s) without deviating from the spirit of the present invention. Similarly, the solid dressing of the present invention may contain one or more of these haemostatic layers as well as one or more other layers, such as one or more support layers (e.g. a backing material or an internal support material) and release layers.

Other preferred embodiments of the present invention are directed to methods for treating wounded tissue in a mammal, comprising placing a solid dressing of the present invention to wounded tissue and applying sufficient pressure to the dressing for a sufficient time for enough fibrin to form to reduce the loss of blood and/or other fluid from the wound.

Still other preferred embodiments are directed to compositions consisting essentially of a mixture of a fibrinogen component, a fibrinogen activator and water, wherein these compositions are stable at reduced temperature for at least 24 hours. These include frozen compositions and liquid compositions. Such compositions are particularly useful for preparing the haemostatic layer(s) of the inventive solid dressings, but may also be used themselves to treat wounded tissue.

According to certain embodiments of the present invention, the haemostatic layer(s) of the solid dressing is cast as a single piece. According to these embodiments, the haemostatic layer may be formed by introducing an aqueous solution of the fibrinogen component and an aqueous solution of the fibrinogen activator into a suitable vessel, such as a mold or the like, with mixing. The resulting aqueous mixture is then cooled to form a frozen aqueous mixture of the fibrinogen component and the fibrinogen activator.

According to certain other embodiments of the present invention, the haemostatic layer is made from a single source, e.g. an aqueous solution containing a mixture of the fibrinogen and the fibrinogen activator. According to these embodiments, the haemostatic layer may be formed by introducing a liquid aqueous mixture of the fibrinogen component and the fibrinogen activator into a suitable vessel, such as a mold or the like, and then reducing the temperature to form a frozen aqueous mixture of the fibrinogen component and the fibrinogen activator.

Preferably, in each of the embodiments of the present invention, the haemostatic layer(s) is substantially homogeneous throughout.

According to certain preferred embodiments of the present invention, the solid dressing is manufactured using a mold.

According to these embodiments, the solid dressings may also optionally further comprise a release layer in addition to the haemostatic layer(s) and support layer(s). As used herein, a "release layer" refers to a layer containing one or more agents ("release agents") which promote or facilitate removal of the solid dressing from a mold in which it has been manufactured. A preferred such agent is sucrose, but other suitable release agents include gelatin, hyaluron and its derivatives, such as hyaluronic acid, mannitol, sorbitol and glucose. Such a release layer is preferably placed or formed in the mold prior to introducing the liquid aqueous mixture or the solutions of fibrinogen component and fibrinogen activator.

Alternatively, such one or more release agents may be contained in the haemostatic layer. According to these embodiments, the release agent may introduced into the liquid aqueous mixture prior to or during introduction of the liquid aqueous mixture into the mold. The release agent may also be introduced into the solution of fibrinogen component and/or the solution of fibrinogen activator prior to or during formation of the liquid aqueous mixture.

The aqueous mixture of the fibrinogen component and the fibrinogen activator may be performed in any suitable vessel. According to certain preferred embodiments, the vessel used for mixing is the mold in which the liquid aqueous mixture is to be subsequently frozen. According to such embodiments, separate liquid aqueous solutions of the fibrinogen component and the fibrinogen activator are simultaneously introduced into the mold, thereby causing the two solutions to mix. Alternatively, a single liquid aqueous solution of the fibrinogen component and the fibrinogen activator may be prepared in a vessel and then subsequently introduced into the mold.

The size and geometry of a given mold may be determined empirically by one skilled in the art depending upon the desired size and shape of the solid dressing being produced. Suitable materials for a mold include, but are not limited to, polymers such as polyvinyl chloride (PVC), Glycol-modified polyethlylenetetrapthalate (PETG) and polyethylene. Other suitable materials include metals, such as stainless steel, paper, cardboard and waterproofed paper or cardboard. The mold may also be fabricated from a rapidly dissolving material that is solid at the temperatures at which the mold is kept and/or from a material that is capable of being lyophylized into a solid state.

According to the methods of the present invention, formation of a liquid aqueous mixture of the fibrinogen component and the fibrinogen activator is performed at a temperature that is sufficiently low to inhibit the activation of the fibrinogen component by the fibrinogen activator.

Activation of the fibrinogen component by the fibrinogen activator may be determined by any suitable method known and available to those skilled in the art. For example, the formation of fibrin from activation of the fibrinogen component can be detected visually by noting deviations from a homogenous surface appearance in the resulting solid dressing. Solid, smooth and glossy "sheets" on the surface of solid dressings are also signs of fibrin, as is excessive curling of the edges. Moreover, once hydrated, dressings with a significant amount of fibrin usually have a mottled and distinctly non-homogenous appearance.

Preferably, activation of the fibrinogen component may be assessed by various biochemical assays, such as the method described in U.S. Patent Application Publication No. US 2006/0155234 A1. According to this assay, the conversion of the fibrinogen γ chains to cross-linked γ-γ dimers may be used as an indication of the activation of the fibrinogen component by the fibrinogen activator (the proportion of γ chain that is converted to γ-γ dimer being related to the amount of fibrinogen activated).

Other biochemical assays could assess changes in the other component chains of fibrinogen, such as the conversion of the Aα chain into free α chain and fibrinopeptide A or the conversion of the Bβ chain into free β chain and fibrinopeptide B. These changes can be monitored by gel electrophoresis in a similar manner to the γ to γ-γ conversion described in U.S. Patent Application Publication No. US 2006/0155234 A1.

Preferred liquid aqueous mixtures prepared using the inventive processes generally contain no detectable to γ-γ dimer, although it may be acceptable in certain circumstances for the dressing to contain up to 9% γ-γ dimer or even up to 38% γ-γ dimer. Similarly, preferred liquid aqueous mixtures may contain up to 60% free α chain and yet still perform acceptably. Particularly preferred aqueous mixtures will contain less than 60% free α chain, more preferably less than 50%, and even more preferably less than 40%, less than 30%, less than 20% or less than 100% free α chain. According to certain preferred embodiments, these values do not significantly change over time when the liquid aqueous mixture is maintained at a suitable temperature, preferably at or below 4° C.±2° C.

The temperature for preparing the liquid aqueous mixtures is sufficient to inhibit the activation of the fibrinogen component by the fibrinogen activator. Preferably, this temperature is at or below 2° C. to 8° C., or more preferably 4° C.±2° C. Any suitable method may be used to achieve the desired temperature for preparing the liquid aqueous mixture.

According to certain preferred embodiments, the vessel or mold is cooled to a desired temperature by placing it in an environment having a temperature at or below the desired temperature. Preferably, the vessel or mold is cooled to a temperature substantially below the desired temperature for preparing the liquid aqueous mixture. According to a particularly preferred embodiment, the vessel or mold is cooled by placing it in an environment having a temperature of about −80° C. for a sufficient time.

According to other embodiments, the aqueous solution of the fibrinogen component and the aqueous solution of the fibrinogen activator are cooled to a desired temperature before preparing the liquid aqueous mixture. Such cooling may be achieved by any suitable method, such as placing vessels containing the aqueous solutions on ice.

Once the liquid aqueous mixture has been prepared, it may be stored at a suitable temperature or it may be used directly to prepare the frozen aqueous mixture of the present invention. Preferably, the liquid aqueous mixture is used directly to prepare the frozen aqueous mixture.

According to certain preferred embodiments of the present invention, the liquid aqueous mixture is subsequently cooled to a temperature where it becomes a frozen aqueous mixture of the fibrinogen component and the fibrinogen activator. Such a frozen aqueous mixture may be used directly, or it may be stored at a suitable temperature.

The liquid aqueous mixture may be cooled to the requisite temperature using any of the methods and techniques known and available to those skilled in the art. For example, the liquid aqueous mixture may be introduced into a second vessel or mold which has been cooled to a temperature sufficient to cause the liquid aqueous mixture to freeze. Alternatively, the liquid aqueous mixture in the vessel or mold may be placed in an environment having a temperature sufficient to cause the liquid aqueous mixture to freeze. Such an environment could include, for example, a freezer set to a predetermined temperature, such as −5° C., −10° C., −15° C., −20° C., −25° C., −30° C., −40° C., −50° C. or −80° C. The mold may be placed such that one or more surfaces thereof is in intimate contact with a surface that has been and/or is cooled to a desired temperature. Alternatively, the mold or vessel containing the liquid aqueous solution can be placed directly on dry ice (−78° C.) or into a suitable cooling bath, such as dry ice/acetone, dry ice/liquid nitrogen or liquid nitrogen alone. The mold or vessel may also be placed in a stream of nitrogen gas produced by the evaporation of liquid nitrogen or other suitable cryogenic gas coolant. In this case, it may be desirable for the gaseous stream to contact a single side of the mold to be cooled. In a more preferred embodiment, such a stream could be directed to two or more sides of the object to be cooled.

Preferred frozen aqueous mixtures prepared using the inventive processes generally contain no detectable to γ-γ dimer, although it may be acceptable in certain circumstances for the mixture to contain up to 9% γ-γ dimer or even 38% γ-γ dimer. Similarly, preferred frozen aqueous mixtures may contain up to 57% free α chain and yet still perform acceptably. Particularly preferred frozen aqueous mixtures will contain less than 57% free α chain, more preferably less than 46%, and even more preferably less than 46%, less than 310%, less than 20%, less than 16% or less than 10% free α chain. According to certain preferred embodiments, these values do not significantly change over time.

The frozen aqueous mixture may be stored or used directly, either to prepare solid dressings or to treat wounded tissue. Certain embodiments of the present invention are directed to these frozen aqueous mixtures, and to their use either for the preparation of solid dressings or for the treatment of wounded tissue.

Preferably, when used to prepare a solid dressing, the frozen aqueous mixture is subjected to a process, such as lyophilization or freeze-drying, that will reduce the moisture content to the desired level, i.e. to a level where the dressing is solid, but not frozen, and therefore will not substantially change in shape or form upon standing, wound-facing surface down, at room temperature for 24 hours. Similar processes that achieve the same result, such as drying, spray-drying, vacuum drying and vitrification, may also be employed.

As used herein, "moisture content" refers to the amount freely-available water in the dressing. "Freely-available" means the water is not bound to or complexed with one or more of the non-liquid components of the dressing. The moisture content referenced herein refers to levels determined by procedures substantially similar to the FDA-approved, modified Karl Fischer method (Meyer and Boyd, Analytical Chem., 31:215-219, 1959; May et al., J. Biol. Standardization, 10:249-259, 1982; Centers for Biologics Evaluation and Research, FDA, Docket No. 89D-0140, 83-93; 1990) or by near infrared spectroscopy.

One skilled in the art may determine empirically the appropriate conditions for lyophilization or freeze-drying, including (but not limited to) the temperature and duration thereof, of the frozen aqueous mixture to form a solid dressing. Such conditions will depend, for example, upon the moisture content of the frozen aqueous mixture, the desired moisture content of the solid dressing, the environment in which the process is performed and the equipment used.

The solid dressings produced by the inventive methods are also preferred embodiments of the present invention. Such dressings contain sufficient fibrinogen component and sufficient fibrinogen activator to form a fibrin clot when applied to wounded tissue, either with or without additional hydration. Such dressings do not contain an undesirable amount of fibrin, whether cross-linked or not. One skilled in the art may determine empirically whether a particular amount of fibrin is undesirable based upon pre-determined characteristics of the solid dressing, such as visual appearance, flexibility, hydration time and the like, as well as the intended use thereof (e.g. a dressing intended for use on an oozing wound may tolerate larger amounts of fibrin than a dressing intended for use on an arterial wound).

The amount of fibrin present in a given dressing may be determined by any suitable method known and available to those skilled in the art. For example, the amount of fibrin in a particular dressing can be detected visually by noting deviations from a homogenous surface appearance. Solid, smooth and glossy "sheets" on the surface of solid dressings are also signs of fibrin, as is excessive curling of the edges. Moreover, once hydrated, dressings with a significant amount of fibrin usually have a mottled and distinctly non-homogenous appearance.

Alternatively, the amount of fibrin may be determined by can also be assessed by various biochemical assays, such as the method described in U.S. Patent Application Publication No. US 2006/0155234 A1. According to this assay, the conversion of the fibrinogen γ chains to cross-linked γ-γ dimers is used as an indication of the presence of fibrin (the proportion of γ chain that is converted to γ-γ dimer being a measure of the amount of fibrin produced).

Other biochemical assays could assess changes in the other component chains of fibrinogen, such as the conversion of the Aα chain into free α chain and fibrinopeptide A or the conversion of the Bβ chain into free β chain and fibrinopeptide B. These changes can be monitored by gel electrophoresis in a similar manner to the γ to γ-γ conversion described in U.S. Patent Application Publication No. US 2006/0155234 A1.

Preferred solid dressings prepared using the inventive processes generally contain no detectable to γ-γ dimer, although it may be acceptable in certain circumstances for the dressing to contain up to up to 9% γ-γ dimer or even 38% γ-γ dimer. Similarly, preferred frozen aqueous mixtures may contain up to 57% free α chain and yet still perform acceptably. Particularly preferred frozen aqueous mixtures will contain less than 57% free α chain, more preferably less than 46%, and even more preferably less than 46%, less than 31%, less than 20%, less than 16% or less than 10% free α chain.

According to certain preferred embodiments, the haemostatic layer(s) of the solid dressing may also contain a binding agent to facilitate or improve the adherence of the layer(s) to one another and/or to any support layer(s). Illustrative examples of suitable binding agents include, but are not limited to, sucrose, mannitol, sorbitol, gelatin, hyaluron and its derivatives, such as hyaluronic acid, maltose, povidone, starch, chitosan and its derivatives, and cellulose derivatives, such as carboxymethylcellulose, as well as mixtures of two or more thereof. Such a binding agent may be introduced into the aqueous mixture of the fibrinogen component and the fibrinogen activator, or may be introduced into an aqueous solution of the fibrinogen component and/or an aqueous solution of the fibrinogen activator prior to mixing.

The haemostatic layer(s) of the solid dressing may also optionally contain one or more suitable fillers, such as sucrose, lactose, maltose, silk, fibrin, collagen, albumin, polysorbate (Tween™), chitin, chitosan and its derivatives, such as NOCC-Chitosan, alginic acid and salts thereof, cellulose and derivatives thereof, proteoglycans, hyaluron and its derivatives, such as hyaluronic acid, glycolic acid polymers, lactic acid polymers, glycolic acid/lactic acid co-polymers, and mixtures of two or more thereof. Such a filler may be introduced into the aqueous mixture of the fibrinogen component and the fibrinogen activator, or may be introduced into an aqueous solution of the fibrinogen component and/or an aqueous solution of the fibrinogen activator prior to mixing.

The haemostatic layer of the solid dressing may also optionally contain one or more suitable solubilizing agents, such as sucrose, dextrose, mannose, trehalose, mannitol, sorbitol, albumin, hyaluron and its derivatives, such as hyaluronic acid, sorbate, polysorbate (Tween™), sorbitan (SPAN™) and mixtures of two or more thereof. Such a solubilizing agent may be introduced into the aqueous mixture of the fibrinogen component and the fibrinogen activator, or may be introduced into an aqueous solution of the fibrinogen component and/or an aqueous solution of the fibrinogen activator prior to mixing.

The haemostatic layer of the solid dressing may also optionally contain one or more suitable foaming agents, such as a mixture of a physiologically acceptable acid (e.g. citric acid or acetic acid) and a physiologically suitable base (e.g. sodium bicarbonate or calcium carbonate). Other suitable foaming agents include, but are not limited to, dry particles containing pressurized gas, such as sugar particles containing carbon dioxide (see, e.g., U.S. Pat. No. 3,012,893) or other physiologically acceptable gases (e.g. Nitrogen or Argon), and pharmacologically acceptable peroxides. Such a foaming agent may be introduced into the aqueous mixture of the fibrinogen component and the fibrinogen activator, or may be introduced into an aqueous solution of the fibrinogen component and/or an aqueous solution of the fibrinogen activator prior to mixing.

The haemostatic layer(s) of the solid dressing may also optionally contain a suitable source of calcium ions, such as calcium chloride, and/or a fibrin cross-linker, such as a transaminase (e.g. Factor XIII/XIIIa) or glutaraldehyde. Sources of calcium ions and/or fibrin cross-linkers may be introduced into the aqueous mixture of the fibrinogen component and the fibrinogen activator, or may be introduced into an aqueous solution of the fibrinogen component and/or an aqueous solution of the fibrinogen activator prior to mixing.

Suitable moisture content(s) for a particular solid dressing may be determined empirically by one skilled in the art depending upon the intended application(s) thereof.

For example, in certain embodiments of the present invention, higher moisture contents are associated with more flexible solid dressings. Thus, in solid dressings intended for extremity wounds, it may be preferred to have a moisture content of at least 6% and even more preferably in the range of 6% to 44%.

Similarly, in other embodiments of the present invention, lower moisture contents are associated with more rigid solid dressings. Thus, in solid dressings intended for flat wounds, such as wounds to the abdomen or chest, it may be preferred to have a moisture content of less than 6% and even more preferably in the range of 1% to 6%.

Accordingly, illustrative examples of suitable moisture contents for solid dressings include, but are not limited to, the following (each value being ±0.9%): less than 53%; less than 44%; less than 28%; less than 24%; less than 16%; less than 12%; less than 6%; less than 5%; less than 4%; less than 3%; less than 2.5%; less than 2%; less than 1.4%; between 0 and 12%, non-inclusive; between 0 and 6%; between 0 and 4%; between 0 and 3%; between 0 and 2%; between 0 and 1%; between 1 and 16%; between 1 and 11%; between 1 and 8%; between 1 and 6%; between 1 and 4%; between 1 and 3%; between 1 and 2%; and between 2 and 4%.

The fibrinogen component in the haemostatic layer(s) of the solid dressings may be any suitable fibrinogen known and available to those skilled in the art. The fibrinogen component may also be a functional derivative or metabolite of a fibrinogen, such the fibrinogen $\alpha$, $\beta$ and/or $\gamma$ chains, soluble fibrin I or fibrin II, or a mixture of two or more thereof. A specific fibrinogen (or functional derivative or metabolite) for a particular application may be selected empirically by one skilled in the art. As used herein, the term "fibrinogen" is intended to include mixtures of fibrinogen and small amounts of Factor XIII/Factor XIIIa, or some other such transaminase. Such small amounts are generally recognized by those skilled in the art as usually being found in mammalian fibrinogen after it has been purified according to the methods and techniques presently known and available in the art, and may be of any amount, and typically range from, 0.1 to 20 Units/mL.

Preferably, the fibrinogen employed as the fibrinogen component of the solid dressing is a purified fibrinogen suitable for introduction into a mammal. Typically, such fibrinogen is a part of a mixture of human plasma proteins which include Factor XIII/XIIIa and have been purified to an appropriate level and virally inactivated. A preferred aqueous solution of fibrinogen for preparation of a solid dressing contains around 37.5 mg/mL fibrinogen at a pH of around 7.4±0.1, although a pH in the range of 5.5-8.5 may be acceptable. Suitable fibrinogen for use as the fibrinogen component has been described in the art, e.g. U.S. Pat. No. 5,716,645, and similar materials are commercially available, e.g. from sources such as Sigma-Aldrich, Enzyme Research Laboratories, Haematologic Technologies and Aniara.

Preferably, the fibrinogen component is present in an amount of from about 1.5 to about 13.0 mg (±0.9 mg) of fibrinogen per square centimeter of solid dressing, and more preferably from about 3.0 to about 13.0 mg/cm$^2$. Greater or lesser amounts, however, may be employed depending upon the particular application intended for the solid dressing. For example, according to certain embodiments where increased adherence is desired, the fibrinogen component is present in an amount of from about 11.0 to about 13.0 mg (±0.9 mg) of fibrinogen per square centimeter of solid dressing. Likewise, according to certain embodiments which are intended for treating low pressure-containing vessels, lower levels of the fibrinogen component may be employed.

The fibrinogen activator employed in the haemostatic layer(s) of the solid dressing may be any of the substances or mixtures of substances known by those skilled in the art to convert fibrinogen into fibrin. Illustrative examples of suitable fibrinogen activators include, but are not limited to, the following: thrombins, such as human thrombin or bovine thrombin, and prothrombins, such as human prothrombin or prothrombin complex concentrate (a mixture of Factors II, VII, IX and X); snake venoms, such as batroxobin, reptilase (a mixture of batroxobin and Factor XIIIa), bothrombin, calobin, fibrozyme, and enzymes isolated from the venom of Bothrops jararacussu; and mixtures of any two or more of these. See, e.g., Dascombe et al., Thromb. Haemost. 78:947-51 (1997); Hahn et al., J. Biochem. (Tokyo) 119:835-43 (1996); Fortova et al, J. Chromatogr. S. Biomed. Appl. 694: 49-53 (1997); and Andriao-Escarso et al., Toxicon. 35: 1043-52 (1997).

Preferably, the fibrinogen activator is a thrombin. More preferably, the fibrinogen activator is a mammalian thrombin, although bird and/or fish thrombin may also be employed in appropriate circumstances. While any suitable mammalian thrombin may be used in the solid dressing, the thrombin employed in the haemostatic layer is preferably a lyophilized mixture of human plasma proteins which has been sufficiently purified and virally inactivated for the intended use of the solid dressing. Suitable thrombin is available commercially from sources such as Sigma-Aldrich, Enzyme Research Laboratories, Haematologic Technologies and Biomol International. A particularly preferred aqueous solution of thrombin for preparing a solid dressing contains thrombin at a potency of between 10 and 2000±50 International Units/mL, and more preferred at a potency of 25±2.5 International Units/mL. Other constituents may include albumin (generally about 0.1 mg/mL) and glycine (generally about 100 mM±0.1 mM). The pH of this particularly preferred aqueous solution of thrombin is generally in the range of 6.5-7.8, and preferably 7.4±0.1, although a pH in the range of 5.5-8.5 may be acceptable.

In addition to the haemostatic layer(s), the solid dressing may optionally further comprise one or more support layers. As used herein, a "support layer" refers to a material that sustains or improves the structural integrity of the solid dressing and/or the fibrin clot formed when such a dressing is applied to wounded tissue.

According to certain preferred embodiments of the present invention the support layer comprises a backing material on the side of the dressing opposite the side to be applied to wounded tissue. Such a backing material may be affixed with a physiologically-acceptable adhesive or may be self-adhering (e.g. by having a sufficient surface static charge). Preferably, the backing material is placed in the mold or vessel prior to introducing the liquid aqueous mixture or the solutions of fibrinogen component and fibrinogen activator. A physiologically-acceptable adhesive may be placed on the backing material prior to introducing the liquid aqueous mixture or solutions of fibrinogen component and fibrinogen activator.

The backing material may comprise one or more resorbable materials or one or more non-resorbable materials or mixtures thereof. Preferably, the backing material is a single resorbable material.

Any suitable resorbable material known and available to those skilled in the art may be employed in the present invention. For example, the resorbable material may be a proteinaceous substance, such as silk, fibrin, keratin, collagen and/or gelatin. Alternatively, the resorbable material may be a carbohydrate substance, such as alginates, chitin, cellulose, proteoglycans (e.g. poly-N-acetyl glucosamine), hyaluron and its derivatives (e.g. hyaluronic acid), glycolic acid polymers, lactic acid polymers, or glycolic acid/lactic acid co-polymers. The resorbable material may also comprise a mixture of proteinaceous substances or a mixture of carbohydrate substances or a mixture of both proteinaceous substances and carbohydrate substances. Specific resorbable material(s) may be selected empirically by those skilled in the art depending upon the intended use of the solid dressing.

According to certain preferred embodiments of the present invention, the resorbable material is a carbohydrate substance. Illustrative examples of particularly preferred resorbable materials include, but are not limited to, the materials sold under the trade names VICRYL™ (a glycolic acid/lactic acid copolymer) and DEXON™ (a glycolic acid polymer).

Any suitable non-resorbable material known and available to those skilled in the art may be employed as the backing material. Illustrative examples of suitable non-resorbable materials include, but are not limited to, plastics, silicone polymers, paper and paper products, latex, gauze and the like.

According to other preferred embodiments, the support layer comprises an internal support material. Such an internal support material is preferably fully contained within a haemostatic layer of the solid dressing, although it may be placed between two adjacent haemostatic layers in certain embodiments. Preferably, the internal support material is placed in the mold or vessel during the introduction of the liquid aqueous mixture or solutions of fibrinogen component and fibrinogen activator.

As with the backing material, the internal support material may be a resorbable material or a non-resorbable material, or a mixture thereof, such as a mixture of two or more resorbable materials or a mixture of two or more non-resorbable materials or a mixture of resorbable material(s) and non-resorbable material(s).

According to still other preferred embodiments, the support layer may comprise a front support material on the wound-facing side of the dressing, i.e. the side to be applied to wounded tissue. As with the backing material and the internal support material, the front support material may be a resorbable material or a non-resorbable material, or a mixture thereof, such as a mixture of two or more resorbable materials or a mixture of two or more non-resorbable materials or a mixture of resorbable material(s) and non-resorbable material(s).

According to still other preferred embodiments, the solid dressing comprises both a backing material and an internal support material in addition to the haemostatic layer(s), i.e. the solid dressing comprises two support layers in addition to the haemostatic layer(s). According to still other preferred embodiments, the solid dressing comprises both a front support material and an internal support material in addition to the haemostatic layer(s). According to still other preferred embodiments, the solid dressing comprises a backing material, a front support material and an internal support material in addition to the haemostatic layer(s).

The various layers of the inventive dressings may be affixed to one another by any suitable means known and available to those skilled in the art. For example, a physiologically-acceptable adhesive may be applied to a backing material (when present), and the haemostatic layer(s) subsequently affixed thereto.

In certain embodiments of the present invention, the physiologically-acceptable adhesive has a shear strength and/or structure such that the backing material can be separated from the fibrin clot formed by the haemostatic layer after application of the dressing to wounded tissue. In other embodiments, the physiologically-acceptable adhesive has a shear strength and/or structure such that the backing material cannot be separated from the fibrin clot after application of the bandage to wounded tissue.

Suitable fibrinogens and suitable fibrinogen activators for the haemostatic layer(s) of the solid dressing may be obtained from any appropriate source known and available to those skilled in the art, including, but not limited to, the following: from commercial vendors, such as Sigma-Aldrich and Enzyme Research Laboratories; by extraction and purification from human or mammalian plasma by any of the methods known and available to those skilled in the art; from supernatants or pastes derived from plasma or recombinant tissue culture, viruses, yeast, bacteria, or the like that contain a gene that expresses a human or mammalian plasma protein which has been introduced according to standard recombinant DNA techniques; and/or from the fluids (e.g. blood, milk, lymph, urine or the like) of transgenic mammals (e.g. goats, sheep, cows) that contain a gene which has been introduced according to standard transgenic techniques and that expresses the desired fibrinogen and/or desired fibrinogen activator.

According to certain preferred embodiments of the present invention, the fibrinogen is a mammalian fibrinogen such as bovine fibrinogen, porcine fibrinogen, ovine fibrinogen, equine fibrinogen, caprine fibrinogen, feline fibrinogen, canine fibrinogen, murine fibrinogen or human fibrinogen.

According to other embodiments, the fibrinogen is bird fibrinogen or fish fibrinogen. According to any of these embodiments, the fibrinogen may be recombinantly produced fibrinogen or transgenic fibrinogen.

According to certain preferred embodiments of the present invention, the fibrinogen activator is a mammalian thrombin, such as bovine thrombin, porcine thrombin, ovine thrombin, equine thrombin, caprine thrombin, feline thrombin, canine thrombin, murine thrombin and human thrombin. According to other embodiments, the thrombin is bird thrombin or fish thrombin. According to any of these embodiments, the thrombin may be recombinantly produced thrombin or transgenic thrombin.

As a general proposition, the purity of the fibrinogen and/or the fibrinogen activator for use in the solid dressing will be a purity known to one of ordinary skill in the relevant art to lead to the optimal efficacy and stability of the protein(s). Preferably, the fibrinogen and/or the fibrinogen activator has been subjected to multiple purification steps, such as precipitation, concentration, diafiltration and affinity chromatography (preferably immunoaffinity chromatography), to remove substances which cause fragmentation, activation and/or degradation of the fibrinogen and/or the fibrinogen activator during manufacture, storage and/or use of the solid dressing. Illustrative examples of such substances that are preferably removed by purification include: protein contaminants, such as inter-alpha trypsin inhibitor and pre-alpha trypsin inhibitor; non-protein contaminants, such as lipids; and mixtures of protein and non-protein contaminants, such as lipoproteins.

The amount of the fibrinogen activator employed in the solid dressing is preferably selected to optimize both the efficacy and stability thereof. As such, a suitable concentration for a particular application of the solid dressing may be determined empirically by one skilled in the relevant art. According to certain preferred embodiments of the present invention, when the fibrinogen activator is human thrombin, the amount of human thrombin employed is between 2.50 Units/mg of fibrinogen component and 0.025 Units/mg of the fibrinogen (all values being ±0.001). Other preferred embodiments are directed to similar solid dressings wherein the amount of thrombin is between 0.250 Units/mg of fibrinogen and 0.062 Units/mg of fibrinogen and solid dressings wherein the amount of thrombin is between 0.125 Units/mg of fibrinogen and 0.080 Units/mg of fibrinogen.

During use of the solid dressing, the fibrinogen and fibrinogen activator are preferably activated at the time the dressing is applied to the wounded tissue by the endogenous fluids of the patient escaping from the hemorrhaging wound. Alternatively, in situations where fluid loss from the wounded tissue is insufficient to provide adequate hydration of the protein layers, the fibrinogen component and/or the thrombin may be activated by a suitable, physiologically-acceptable liquid, optionally containing any necessary co-factors and/or enzymes, prior to or during application of the dressing to the wounded tissue.

In some embodiments of the present invention, the haemostatic layer(s) may also contain one or more supplements, such as growth factors, drugs, polyclonal and monoclonal antibodies and other compounds. Illustrative examples of such supplements include, but are not limited to, the following: fibrinolysis inhibitors, such as aprotonin, tranexamic acid and epsilon-amino-caproic acid; antibiotics, such as tetracycline and ciprofloxacin, amoxicillin, and metronidazole; anticoagulants, such as activated protein C, heparin, prostacyclins, prostaglandins (particularly $PGI_2$), leukotrienes, antithrombin III, ADPase, and plasminogen activator; steroids, such as dexamethasone, inhibitors of prostacyclin, prostaglandins, leukotrienes and/or kinins to inhibit inflammation; cardiovascular drugs, such as calcium channel blockers, vasodilators and vasoconstrictors; chemoattractants; local anesthetics such as bupivacaine; and antiproliferative/antitumor drugs such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as alpha- or beta- or gamma-Interferon, alpha- or beta-tumor necrosis factor, and interleukins; colony stimulating factors; erythropoietin; antifungals, such as diflucan, ketaconizole and nystatin; antiparasitic gents, such as pentamidine; anti-inflammatory agents, such as alpha-1-antitrypsin and alpha-1-antichymotrypsin; anesthetics, such as bupivacaine; analgesics; antiseptics; hormones; vitamins and other nutritional supplements; glycoproteins; fibronectin; peptides and proteins; carbohydrates (both simple and/or complex); proteoglycans; antiangiogenins; antigens; lipids or liposomes; oligonucleotides (sense and/or antisense DNA and/or RNA); and gene therapy reagents. In other embodiments of the present invention, the backing layer and/or the internal support layer, if present, may contain one or more supplements. According to certain preferred embodiments of the present invention, the therapeutic supplement is present in an amount greater than its solubility limit in fibrin.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

EXAMPLES

The ability of the dressings to seal an injured blood vessel was determined by an ex vivo porcine arteriotomy (EVPA) performance test, which was first described in U.S. Pat. No. 6,762,336. The EVPA performance test evaluates the ability of a dressing to stop fluid flow through a hole in a porcine artery. While the procedure described in U.S. Pat. No. 6,762,336 has been shown to be useful for evaluating haemostatic dressings, it failed to replicate faithfully the requirements for success in vivo. More specifically, the procedure disclosed in U.S. Pat. No. 6,762,336 required testing at 37° C., whereas, in the real world, wounds are typically cooler than that. This decreased temperature can significantly reduce the rate of fibrin formation and its haemostatic efficacy in trauma victims. See, e.g., Acheson et al., J. Trauma 59:865-874 (2005). The test in U.S. Pat. No. 6,762,336 also failed to require a high degree of adherence of the dressing to the injured tissue. A failure mode in which fibrin forms but the dressing fails to attach tightly to the tissue would, therefore, not be detected by this test. Additionally, the pressure utilized in the procedure (200 mHg) may be exceeded during therapy for some trauma patients. The overall result of this is that numerous animal tests, typically involving small animals (such as rats and rabbits), must be conducted to accurately predict dressing performance in large animal, realistic trauma studies and in the clinical environment.

In order to minimize the amount of time and the number of animal studies required to develop the present invention, an improved ex vivo testing procedure was developed. To accomplish this, the basic conditions under which the dressing test was conducted were changed, and the severity of the test parameters was increased to include testing at lower temperatures (i.e. 29-33° C. vs. 37° C., representing the real physiologic challenge at realistic wound temperatures (Acheson et al., J. Trauma 59:865-874 (2005)), higher pressures (i.e. 250 mmHg vs. 200 mmHg), a longer test period (3 minutes vs. 2 minutes) and larger sized arterial injuries (U.S. Pat. No. 6,762,336 used an 18 gauge needle puncture, whereas the revised procedure used puncture holes ranging from 2.8 mm to 4 mm×6 mm).

In addition, a new test was derived to directly measure adherence of the dressing to the injured tissue. Both these tests showed greatly improved stringency and are thus capable of surpassing the previous ex vivo test and replacing many in vivo tests for efficacy.

The following is a list of acronyms used in the Examples below:
CFB: Complete Fibrinogen Buffer (100 mM Sodium Chloride, 1.1 mM Calcium Chloride, 10 mM Tris, 10 mM Sodium Citrate, 1.5% Sucrose, Human Serum Albumin (80 mg/g of total protein) and Tween™ 80 (animal source) 15 mg/g total protein)
CTB: Complete Thrombin Buffer (150 mM Sodium Chloride, 40 mM Calcium Chloride, 10 mM Tris and 100 mM L-Lysine with the addition of HSA at 100 ug/ml)
ERL: Enzyme Research Laboratories
EVPA: Ex Vivo Porcine Arteriotomy
FD: Inventive haemostatic dressing
HSA: Human Serum Albumin
HD: A "sandwich" fibrin sealant haemostatic dressing as disclosed in U.S. Pat. No. 6,762,336
IFB: Incomplete Fibrinogen Buffer; CFB without HSA and Tween
PETG: Glycol-modified Polyethlyenetetrapthalate
PPG: Polypropylene
PVC: Poly vinyl chloride
TRIS: trishydroxymethylaminomethane (2-amino-2-hydroxymethyl-1,3-propanediol)

Example 1

Backing material (DEXON™) was cut and placed into each PETG 2.4×2.4 cm mold. Twenty-five microliters of 2% sucrose was pipetted on top of each of the four corners of the backing material. Once completed the molds were placed in a −80° C. freezer for at least 60 minutes. Fibrinogen (Enzyme Research Laboratories™) was formulated in CFB. The final pH of the fibrinogen was 7.4±0.1. The fibrinogen concentrations were adjusted to 37.5, 31.7, 25.9, 20.16, 14.4, 8.64, and 4.3 mg/ml. When 2 ml of fibrinogen was delivered into the molds, this would result in a fibrinogen dose of 13, 11, 9, 7, 5, 3 or 1.5 mg/cm². Once prepared the fibrinogen was placed on ice until use. Thrombin was formulated in CTB. The final pH of the thrombin was 7.4±0.1. The concentrations of thrombin were adjusted so that when mixed with the fibrinogen solutions as described below, the combination would produce a solution that contained 0.1 units/mg of Fibrinogen. Once prepared the thrombin was placed on ice until use. The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Two ml of fibrinogen and 300 micro liters of thrombin were dispensed simultaneously into each mold. Once the molds were filled they were allowed to freeze and then returned to the −80° C. freezer for at least two hours. The frozen dressings were then placed into a pre-cooled Genesis™ lyophylizer (Virtis, Gardiner, N.Y.). The chamber was sealed and the temperature equilibrated. The chamber was then evacuated and the dressings lyophilized via a primary and secondary drying cycle.

The dressings were removed from the lyophylizer, sealed in foil pouches and stored at room temperature until testing. Subsequently, the dressings were evaluated in the EVPA, Adherence and Weight Assays.

The results are given in the following Table and depicted graphically in FIGS. 3A-3C.

| Group | EVPA Pass/Total | Peel Test Adherence | Adherence Std Dev | Weight Held (mean) (g) | Weight Held Std Dev |
| --- | --- | --- | --- | --- | --- |
| 13 mg/cm² | 6/6 | 4.0 | 0.0 | 198.0 | 12.6 |
| 11 mg/cm² | 6/6 | 3.8 | 0.4 | 163 | 48.5 |
| 9 mg/cm² | 5/6 | 3.0 | 0.0 | 88 | 20.0 |
| 7 mg/cm² | 6/6 | 3.2 | 0.4 | 93 | 17.6 |
| 7 mg/cm² | 5/6 | 3.0 | 0.0 | 94.7 | 8.2 |
| 5 mg/cm² | 5/5 | 2.8 | 0.4 | 76 | 34.2 |
| 3 mg/cm² | 5/5 | 2.4 | 0.5 | 48 | 27.4 |
| 1.5 mg/cm² | 0/6 | 0.1 | 0.2 | 4.7 | 11.4 |

Example 2

Monolithic dressings were manufactured as follows: backing material was cut and placed into each PETG 2.4×2.4 cm mold. Twenty-five microliters of 2% sucrose was pipetted on top of each of the four corners of the backing material. Once completed the molds were placed in a −80° C. freezer for at least 60 minutes.

For all dressings, ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use. Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use. The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophilized as described above. Once complete the dressings were stored in low moisture transmission foil bags containing 5 grams of desiccant.

Trilayer dressings were manufactured as described previously, using the same materials as described above. Subsequently, the dressings were placed under conditions of 100% relative humidity at 37° C. for various times in order to increase their relative moisture content to desired levels. The dressings were evaluated visually and for their handling and other physical characteristics. Following this evaluation, a sample of each of the dressings was tested to determine their moisture content. The remaining dressings were performance tested in the EVPA, Adherence and Weight Held assays.

Results

The results of the assays are given in the Tables below:

TABLE 1

Performance Data of Inventive Solid Dressings

| Exposure Time to 100% Humidity @ 37° C. (minutes) | % Moisture | EVPA # Pass/Total | Peel Test Adherence (±Std. Dev.) | Weight Held (g) (mean ± Std. Dev.) |
|---|---|---|---|---|
| 0 | 2.5 | 2/2 | 4.0 ± 0 | 148 ± 28.3 |
| 1 | 5.8 | 2/2 | 3.5 ± 0.71 | 123 ± 7.1 |
| 15 | 16 | 2/2 | 2.5 ± .71 | 108 ± 14.1 |
| 45 | 24 | 2/2 | 4.0 ± 0 | 168 ± 0 |
| 60 | 28 | 2/2 | 4.0 ± 0 | 273 ± 7.1 |
| 225 | 44 | 2/2 | 2 ± 0 | 58 ± 14.1 |
| 1200 | 52 | ND | ND | ND |

TABLE 2

Performance Data for Tri-layer Dressings

| Exposure Time to 100% Humidity @ 37° C. (minutes) | % Moisture | EVPA # Pass/Total | Peel Test Adherence | Weight Held (g) (mean) |
|---|---|---|---|---|
| 0 | 3 | 1/1 | 2.0 | 78 |
| 15 | 22 | 1/1 | 2.0 | 78 |
| 60 | 33.7 | 0/1 | 0.5 | 28 |

TABLE 3

Integrity and Handling Characteristics of Inventive Solid Dressings

| Exposure Time to 100% Humidity @ 37° C. (minutes) | Prior To Hydration | | | | During Hydration | | |
|---|---|---|---|---|---|---|---|
| | Surface Appearance | Curling | Integrity | Flexible | Speed of Hydration | Force Required for Hydration | After Hydration Appearance |
| 0 | Normal (Smooth, No "skin") | No | Excellent (No cracks or flaking off) | No | Normal | No | Normal |
| 1 | Normal (Smooth, No "skin") | " | Excellent (No cracks or flaking off) | Yes | " | " | " |
| 15 | Normal (Smooth, No "skin") | " | Excellent (No cracks or flaking off) | " | " | " | " |
| 45 | Normal (Smooth, No "skin") | " | Excellent (No cracks or flaking off) | " | " | " | " |
| 60 | Normal (Smooth, No "skin") | Slight | Excellent (No cracks or flaking off) | " | " | " | " |
| 225 | Normal (Smooth, No "skin") | Yes | Excellent (No cracks or flaking off) | " | " | " | " |
| 1200 | Normal (Smooth, No "skin") | Curling up on itself | Excellent (No cracks or flaking off) | " | n/d | n/d | Mottled and lumpy |

TABLE 4

Integrity and Handling Characteristics of Trilayer Dressings

| Exposure Time to 100% Humidity @ 37° C. (minutes) | Prior To Hydration | | | | During Hydration | | |
|---|---|---|---|---|---|---|---|
| | Surface Appearance | Curling | Integrity | Flexibility | Speed of Hydration | Force Required for Hydration | After Hydration Appearance |
| 0 | Normal | No | Good; some delamination | No | Normal | No | Normal |
| 15 | Irregular | No | Good; some delamination | Yes | Slow | No | Mottled |
| 60 | Skinned | Yes | Good; some delamination | Yes | Very Slow | Yes | Very Mottled and lumpy |

Conclusions:

The monolithic dressings were fully functional at very high levels of moisture. As much as 28% moisture was found to retain complete functionality. When the moisture levels rose to 44%, the dressings were still functional, however some of their activity was reduced Higher levels of moisture may also retain some function. The original dressings, at 2.5% moisture content, were not flexible, but had all the other desired properties including appearance, a flat surface, integrity, rapid and uncomplicated hydration and a smooth appearance post hydration. Once the moisture content was increased to 5.8%, the monolithic dressings became flexible, while retaining their functionality and desirable characteristics. They retained their flexibility, without curling or losing their integrity or appearing to form excessive amounts of fibrin prior to hydration.

This contrasted with the tri-layer dressings, which began to lose their desirable characteristics upon the addition of moisture, and lost them entirely by the time moisture had increased to 33%.

Example 3

For dressings utilizing a backing, the backing material was cut and placed into each PETG 2.4×2.4 cm mold. Twenty-five microliters of 2% sucrose was pipetted on top of each of the four corners of the backing material. Once completed the molds were placed in a −80° C. freezer for at least 60 minutes. For dressings without backing material, PETG 2.4×2.4 cm molds were placed in a −80° C. freezer for at least 60 minutes.

For all dressings, ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use. Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use. The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filed with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophylized as described below.

Both groups were performance tested in the EVPA assay. In addition, the group which had a backing was also tested in the Adherence and Weight Held assays.

Results:

| Group | EVPA # Pass/Total | Peel Test Adherence | Adherence Std Dev | Weight Held (mean) (g) | Weight Held Std Dev |
|---|---|---|---|---|---|
| Backing | 6/6 | 3.7 | 0.5 | 153 | 37.3 |
| No Backing | 9/12 | | | | |

Conclusions:

Dressings formulated with backing material performed well, with all dressings passing the EVPA test, and high values for adherence and weight held. Dressings without backing material were not quite as effective in the EVPA assay, however, surprisingly 75% of them passed the EVPA test. Without the backing the other tests could not be performed. The ability of the dressings made without a backing to succeed in the EVPA assay indicates that these dressings would be effective in treating arterial injuries and even more effective in treating venous and small vessel injuries.

Example 4

For all dressings, ERL fibrinogen lot 3130 was formulated in CFB. The final pH of the fibrinogen was 7.4±0.1. The fibrinogen concentration was adjusted to 37.5 mg/ml. Once prepared the fibrinogen was placed on ice until use. Thrombin was formulated in CTB. The final pH of the thrombin was 7.4±0.1. The thrombin was adjusted to deliver 0.1 units/mg of Fibrinogen or 25 Units/ml thrombin. For the group with shredded VICRYL™ mesh dispersed within, this support material was cut into approximately 1 mm×1 mm pieces and dispersed within the thrombin solution prior to filling the molds. Once prepared the thrombin was placed on ice until use. The temperature of the fibrinogen and thrombin prior to dispensing was 4° C.±2° C. Cylindrical molds made of 10 or 3 mL polypropylene syringes (Becton Dickinson) with the luer-lock end removed were used. The plungers were withdrawn to the 6 mL and 2 mL mark respectively. For dressings utilizing a backing, the support material was cut and placed into each mold and pushed down until it was adjacent to the plunger. Once prepared the molds were placed upright and surrounded by dry ice, leaving the opening exposed at the top. 1 ml of fibrinogen and 0.15 mL of thrombin (with or without backing material dispersed within) were dispensed into the 10 L molds and 1 ml of fibrinogen and 0.15 mL of thrombin (with or without support material dispersed within) were dispensed into the 3 mL molds, which were allowed to freeze for 5 minutes. The molds were then placed into the −80° C. freezer for at least two hours before being placed into the freeze dryer and lyophylized as described above.

Upon removal from the lyophylizer, both groups were performance tested in a modified EVPA assay. Briefly, a plastic foam form was slipped over the artery. This covering had a hole in it that corresponded to the hole in the artery and the surrounding tissue. Warm saline was added to the surface of the dressing and the mold was immediately passed down thru the hole in the foam to the artery surface. The plunger was then depressed and held by hand for 3 minutes, after which the mold was withdrawn as the plunger was depressed further. At this point the artery was pressurized and the assay continued as before.

Results

| Support Material | Mold Size | EVPA Result (@250 mmHg) | Maximum Pressure |
|---|---|---|---|
| None | 10 ml | Pass | >250 mmHg |
| Dexon Mesh Backing | 10 ml | Pass | " |
| " | 3 ml | Pass | " |
| Shredded Dexon Mesh (Dispersed) | 10 ml | Pass | " |
| Shredded Dexon Mesh (Dispersed) | 3 ml | Fail | 150 mmHg |

Conclusions:

Dressings that included no backing or a DEXON™ mesh backing performed well, with all passing the EVPA test at 250 mmHg. When the support material was dispersed throughout the composition, the dressings also performed well, with the large size (10 mL mold) dressings holding the full 250 mmHg of pressure, while the smaller held up to 150 mmHg of pressure. This indicates that the use of a support material may be optional, and it's location may be on the 'back' of the dressing, or dispersed throughout the composition, as desired.

Example 5

Dressings made with a support material on the "back" (i.e. the non wound-facing side) of the dressing were manufactured by first cutting the mesh support material and placing it into each PETG 10×10 cm mold. Twenty-five microliters of 2% sucrose was pipetted on top of each of the four corners of the backing material. Once completed the molds were placed in a −80° C. freezer for at least 60 minutes.

For dressings made with a support material on the "front" (i.e. the wound-facing side) of the dressing, these were manufactured without any support material in the mold. The support mesh was placed atop the dressing immediately after dispensing of the fibrinogen and thrombin into the mold (see below), and lightly pressing it into the surface prior to its freezing. In all other ways the manufacture of the dressings was similar as described below.

For all dressings, ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use. Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use. The thrombin was adjusted to deliver 0.1 units/mg of Fibrinogen or 25 Units/ml thrombin. Once prepared the thrombin was placed on ice until use. The temperature of the fibrinogen and thrombin prior to dispensing was 4° C.±2° C. The mold was removed from the −80° C. freezer and placed on an aluminum plate that was placed on top of dry ice. The aluminum plate had a 0.25 inch hole drilled in the center and a fitting attached so that a piece of tubing could be attached to a vacuum source. The mold was centered over the hole in the aluminum plate and vacuum was turned on. The vacuum served two purposes it prevented the mold from moving and it held it flat against the aluminum plate. Thirty-five milliliters of fibrinogen and 5.25 milliliters of Thrombin were placed in 50 ml test tube, inverted three times and poured into the mold. Once the molds were filled and the support material applied as described above, they were returned to the −80° C. freezer for at least two hours before being placed into the freeze dryer. Dressings were then lyophylized as described previously.

Both groups were performance tested in the EVPA assay. In addition, the group which had a backing was also tested in the Adherence and Weight Held assays.

Results:

| Support Material (Mesh) Orientation | EVPA # Pass/Total | Adherence Test Score | Adherence Std Dev | Weight Held (mean) (g) | Weight Held Std Dev |
|---|---|---|---|---|---|
| Back (away from injury site) | 6/6 | 3.5 | 0.5 | 136 | 49 |
| Front (immediately adjacent to injury site) | 6/6 | 3.8 | 0.4 | 163 | 32 |

Conclusions:

Dressings formulated with backing material in either orientation well, with all dressings passing the EVPA test, and high values for adherence and weight held. This indicates that the location of a support material may be on the 'back' of the dressing, or the 'front', of the composition as desired.

Example 6

Backing material (DEXON™) was placed into 2.4×2.4 cm PETG molds. Twenty-five microliters of 2% sucrose was pipetted on top of each of the four corners of the backing material. Once completed the molds were placed in a −80° C. freezer for at least 60 minutes.

Fibrinogen (Enzyme Research Laboratories™ (ERL) lot 3114) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1. The thrombin concentrations were adjusted with CTB to produce 12.5 units/mg of Fibrinogen (upon mixing), which corresponded to 3120 Units/ml thrombin prior to mixing. Once prepared the thrombin was placed on ice until use.

The temperature of the fibrinogen and thrombin prior to dispensing was 4° C.±2° C. Molds were removed from the −80° C. freezer and placed on a copper plate that was pre-cooled on top of dry ice. A repeat pipettor was filled with fibrinogen and second repeat pipettor was filled with thrombin. Two ml of fibrinogen and 300 micro liters of thrombin were dispensed simultaneously into each mold. Once the molds were filled they were returned to the −80° C. freezer for at least two hours before being placed into the freeze dryer. They were then lyophilized as described below, and performance tested using the EVPA and Adherence Assays as described below. These results are shown in FIG. 4A and FIG. 4B.

Example 7

Backing material was placed into each 1.5×1.5 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes. Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use. Thrombin was formulated in CTB. The final pH of the thrombin was 7.4±0.1. The thrombin concentrations were adjusted using CTB to deliver the following amounts 2.5, 0.25, 0.1, 0.05, 0.025, 0.016, 0.0125 and 0.01 units/mg of Fibrinogen (upon mixing), which corresponded to 624, 62.4, 25, 12.5, 6.24, 3.99, 3.12, and 2.5 Units/ml thrombin prior to mixing. Once prepared the thrombin was placed on ice until use. The temperature of the fibrinogen and thrombin prior to dispensing was 4° C.±2° C. Molds were then removed from the −80° C. freezer and placed on an aluminum plate that was pre-cooled on top of dry ice. Three holes were punched at the top of the mold using an 18 gauge needle. One hole was used for injecting fibrinogen, the second for injecting thrombin, and the third hole served as a vent to release air that was displaced from inside the mold. A pipette was then filled with fibrinogen and a second pipette with thrombin. Simultaneously 0.78 ml of fibrinogen and 0.17 ml of thrombin were injected via these pipettes into each mold. Once filled the molds were placed on top of a pool of liquid nitrogen for thirty seconds and then returned to the −80° C. freezer for at least two hours before being placed into the freeze dryer. They were then lyophilized as described below, and performance tested using the EVPA and Adherence Assays as described below. These results are shown in FIG. 4A and FIG. 4B.

Example 8

Backing material was placed into 2.4×2.4 cm PVC molds. Twenty-five microliters of 2% sucrose was pipetted on top of each of the four corners of the backing material. Once completed the molds were placed in a −80° C. freezer for at least 60 minutes. Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use. Thrombin was formulated in CTB. The final pH of the thrombin was 7.4±0.1. Using CTB, the thrombin concentrations were adjusted to deliver the following amounts 0.125, 0.025, 0.0125, 0.00625 and 0.0031 units/mg of Fibrinogen upon mixing, which corresponded to 31.2, 6.24, 3.12, 1.56 and 0.78 Units/ml thrombin prior to mixing. Once prepared the thrombin was placed on ice until use. The temperature of the fibrinogen and thrombin prior to dispensing was 4° C.±2° C. The molds were removed from the −80° C. freezer and placed on an aluminum plate that that was precooled on top of dry ice. A 3 ml syringe fitted with an 18 gauge needle was filled with 2 ml of fibrinogen and a second, 1 ml, syringe fitted with a 22 gauge needle was filled with 0.3 ml of thrombin. The contents of both syringes were dispensed simultaneously into each mold. Once filled the molds were placed on top of liquid nitrogen for thirty seconds and then returned to the −80° C. freezer for at least two hours before being placed into the freeze dryer. They were then lyophilized as described below, and performance tested using the EVPA and Adherence Assays as described below. These results are shown in FIG. 4A and FIG. 4B.

Example 9

Backing material was placed into PVC 2.4×2.4 cm molds. Twenty-five microliters of 2% sucrose was pipetted on top of each of the four corners of the backing material. Once completed the molds were placed in a −80° C. freezer for at least 60 minutes. A vial containing 3 grams of Fibrinogen (Sigma™ Lot# F-3879) was removed the −20° C. freezer and placed at 4° C. for 18 hours. The bottle was then removed from the freezer and allowed to come to room temperature for 60 minutes. To the bottle, 60 ml of 37° C. water was added and allowed to mix for 15 minutes at 37° C. Once in solution the fibrinogen was dialyzed against incomplete fibrinogen buffer (IFB, which was CFB without HSA and Tween™) for 4 hours at room temperature. At the end of the four hours HSA was added to a concentration of 80 mg/g of total protein, and Tween™ 80 (animal source) was added to a concentration of 15 mg/g total protein. The final pH of the fibrinogen was 7.4±0.1. The fibrinogen concentration was then adjusted to 37.5 mg/m with CFB. Once prepared the fibrinogen was placed on ice until use. Thrombin was formulated in CTB. The final pH of the thrombin was 7.4±0.1. Using CTB, the thrombin concentrations were adjusted to deliver the following amounts 2.5, 0.25, 0.125, 0.083 and 0.0625 units/mg of Fibrinogen (upon mixing) which corresponded to 624, 62.4, 31.2, 20.8 and 15.6 Units/ml thrombin prior to mixing. Once prepared the thrombin was placed on ice until use. The temperature of the fibrinogen and thrombin prior to dispensing was 4° C.±2° C. Molds were removed from the −80° C. freezer and placed on an aluminum plate that was that was precooled on top of dry ice. A 3 ml syringe fitted with an 18 gauge needle was filled with 2 ml of fibrinogen and a second 1 ml syringe fitted with a 22 gauge needle was filled with 0.3 ml of thrombin. The contents of both syringes were dispensed simultaneously into each mold. Once filled the molds were placed on top of liquid nitrogen for thirty seconds and then returned to the −80° C. freezer for at least two hours before being placed into the freeze dryer. They were then lyophilized as described below, and performance tested using the EVPA and Adherence Assays as described below. These results are shown in FIG. 4A and FIG. 4B.

Example 10

Backing material was placed into 2.4×2.4 cm PVC molds. Twenty-five microliters of 2% sucrose was pipetted on top of each of the four corners of the backing material. A second piece of PETG plastic was cut to fit on top of the molds and held in place by clips located at each end of the mold, producing closed molds. Once completed the molds were placed in a −80° C. freezer for at least 60 minutes. Fibrinogen (ERL lot 3060 was formulated in CFB. The final pH of the fibrinogen was 7.4±0.1. The fibrinogen concentration was adjusted to 37.5 mg/ml using CFB. Once prepared the fibrinogen was placed on ice until use. Thrombin was formulated in CTB. The final pH of the thrombin was 7.4±0.1. Using CTB, thrombin concentrations were adjusted to deliver the following amounts 2.5, 0.25, 0.125, 0.083 and 0.062 units/mg of Fibrinogen (after mixing), which corresponded to 624, 62.4, 31.2, 20.8, and 15.6 Units/ml thrombin (prior to mixing). Once prepared the thrombin was placed on ice until use. The temperature of the fibrinogen and thrombin prior to dispensing was 4° C.±2° C. Molds were removed from the −80° C. freezer and placed on an aluminum plate that was that was precooled on top of dry ice. A 3 ml syringe fitted with an 18 gauge needle was filled with 2 ml of fibrinogen and a second, 1 ml, syringe fitted with a 22 gauge needle was filled with 0.3 ml of thrombin. The contents of both syringes were dispensed simultaneously into each mold. Once filled the molds were placed on top of liquid nitrogen for thirty seconds and then returned to the −80° C. freezer for at least two hours before being placed into the freeze dryer. They were then lyophilized as described below, and performance tested using the EVPA and Adherence Assays as described below. These results are shown in FIG. 4A and FIG. 4B.

Example 11

Backing material was placed into 2.4×2.4 cm PVC molds. Twenty-five microliters of 2% sucrose was pipetted on top of each of the four corners of the backing material. A second piece of PETG plastic was cut to fit on top of the 2.4×2.4 molds and held in place by the use of clips located at each end of the mold to create closed molds. The molds were then placed in a −80° C. freezer for at least 60 minutes. A vial containing 3 grams of Fibrinogen (Sigma Lot# F-3879) was removed the −20° C. freezer and placed at 4° C. for 18 hours. The bottle was then removed from the freezer and allowed to come to room temperature for 60 minutes. To the bottle, 60 ml of 37° C. water was added and allowed to mix for 15 minutes at 37° C. Once in solution the fibrinogen was dialyzed against IFB. At the end of the four hours HSA was added to a concentration of 80 mg/g of total protein, and Tween™ 80 (animal source) was added to a concentration of 15 mg/g total protein. The final pH of the fibrinogen was 7.4±0.1. The fibrinogen concentration was adjusted to 37.5 mg/ml using CFB. Once prepared the fibrinogen was placed on ice until use. Thrombin was formulated in CTB. The final pH of the thrombin was 7.4±0.1. Thrombin concentration was adjusted to deliver the following amounts 2.5, 0.25, 0.125, 0.1 and 0.083 units/mg of Fibrinogen (upon mixing), which corresponded to 624, 62.4, 31.2, 24.96 and 20.79 Units/ml thrombin (before mixing). Once prepared the thrombin was placed on ice until use. The temperature of the fibrinogen and thrombin prior to dispensing was 4° C.±2° C. Molds were removed from the −80° C. freezer and placed on an aluminum plate that was that was pre-cooled on top of dry ice. A 3 ml syringe fitted with an 18 gauge needle was filled with 2 ml of fibrinogen and a second, 1 ml, syringe fitted with a 22 gauge needle was filled with 0.3 ml of thrombin. The contents of both syringes were dispensed simultaneously into each mold. Once filled the molds were placed on top of liquid nitrogen for thirty seconds and then returned to the −80° C. freezer for at least two hours before being placed into the freeze dryer. They were then lyophilized as described below, and performance tested using the EVPA and Adherence Assays as described below. These results are shown in FIG. 4A and FIG. 4B.

Example 12

Backing material was placed into 2.4×2.4 cm PVC molds. Twenty-five microliters of 2% sucrose was pipetted on top of each of the four corners of the backing material. A second piece of PETG plastic was cut to fit on top of the molds and held in place by the use of clips located at each end of the mold to create closed molds. Once completed, the molds were placed in a −80° C. freezer for at least 60 minutes.

A vial containing 3 grams of Fibrinogen (Siga™ Lot# F-3879) was removed from the −20° C. freezer and placed at 4° C. for 18 hours. The bottle was then allowed to come to room temperature for 60 minutes. To the bottle, 60 ml of 37° C. water was added and allowed to mix for 20 minutes at 37° C. Once in solution, the fibrinogen was dialyzed against IFB. At the end of the four hours, human serum albumin (HSA) was added to a concentration of 80 mg/g of total protein, and Tween™ 80 (animal source) was added to a concentration of 15 mg/g total protein. The final pH of the fibrinogen was 7.4±0.1. The fibrinogen concentration was adjusted to 37.5 mg/ml using CFB. Once prepared the fibrinogen was placed on ice until use.

Thrombin was formulated in CTB. The final pH of the thrombin was 7.4±0.1. Thrombin was adjusted to deliver the following amounts 2.5, 0.25, 0.125, 0.08 and 0.06 units/mg of Fibrinogen (after mixing), which corresponded to 624, 62.4, 31.2, 20.8 and 15.6 Units/ml thrombin (prior to mixing). Once prepared the thrombin was placed on ice until use. The temperature of the fibrinogen and thrombin prior to dispensing was 4° C.±2° C. Molds were removed from the −80° C. freezer and placed on an aluminum plate that was that was precooled on top of dry ice. A 3 ml syringe fitted with an 18 gauge needle was filled with 2 ml of fibrinogen and a second, 1 ml, syringe fitted with a 22 gauge needle was filled with 0.3 ml of thrombin. The contents of both syringes were dispensed simultaneously into each mold. Once filled the molds were placed on top of liquid nitrogen for thirty seconds and then returned to the −80° C. freezer for at least two hours before being placed into the freeze dryer. They were then lyophilized as described below, and performance tested using the EVPA and Adherence Assays as described below.

Trilayer (Sandwich) Dressings

Trilayer dressings were produced using the process described in U.S. Pat. No. 6,762,336, using the same sources of fibrinogen and thrombin as utilized to produce the monolithic dressings above.

Results

The results of the EVPA and Adherence Assays are shown in FIGS. 4A and 4B, respectively.

Conclusions (Examples 6 thru 12):

Dressings produced with between 2.5 to 0.025 thrombin Units/mg of fibrinogen were active in both assays, while those with greater or lesser ratios of thrombin to fibrinogen were not. Significantly greater activity was seen over the range of 2.5 to 0.05 thrombin Units/mg of fibrinogen. Greatly improved performance was seen between the ranges of 0.25 to 0.062 thrombin Units/mg of fibrinogen, while optimum performance was seen between the ranges of 0.125 to 0.08 thrombin Units/mg of fibrinogen. This contrasted with the dressings produced using the process described in U.S. Pat. No. 6,762,336 which reached full performance at 12.5 thrombin Units/mg of fibrinogen, with unacceptable performance occurring as the thrombin concentration was diminished below 12.5 thrombin Units/mg of fibrinogen, with essentially no activity remaining at 1.4 thrombin Units/mg of fibrinogen. This difference in both the limits of performance and the optimum levels is all the more profound given that the performance of the trilayer dressings from U.S. Pat. No. 6,762, 336 was decreased by the use of decreasing amounts of thrombin, while the dressing described herein showed an increased activity over this range.

Example 13

Backing material was cut and placed into each PETG 2.4× 2.4 cm mold. Twenty-five microliters of 2% sucrose was pipeted on top of each of the four corners of the backing material. Once completed the molds were placed in a −80° C. freezer for at least 60 minutes. Enzyme Research Laboratories (ERL) fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use. Thrombin was formulated in CTB The final pH of the thrombin was 7.4±0.1. The thrombin was adjusted with CTB to deliver 0.1 units/mg of fibrinogen or 25 Units/ml thrombin. Once prepared the thrombin was placed on ice until use. The temperature of the fibrinogen and thrombin prior to dispensing was 4° C.±2° C. Molds were removed from the −80 C freezer and placed on an aluminum plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. One group of dressings was lyophylized on day 0, while the remainders were kept frozen at −80° C. A second group of dressings were lyophylized on day seven and a third group was lyophylized on day fourteen.

Once all the dressings had been lyophilized, they were tested using the EVPA, Adherence, and Weight Assays described herein.

Results:

| Days Frozen Prior to Freeze Drying | EVPA # Pass/Total | Peel Test Adherence | Adherence Std Dev | Weight Held (mean) (g) | Weight Held Std Dev |
|---|---|---|---|---|---|
| 0 | 5/6 | 3.5 | 0.5 | 168.0 | 63.2 |
| 7 | 6/6 | 3.8 | 0.4 | 164.7 | 29.4 |
| 14 | 6/6 | 3.7 | 0.5 | 139.7 | 39.7 |

Figure 5A:
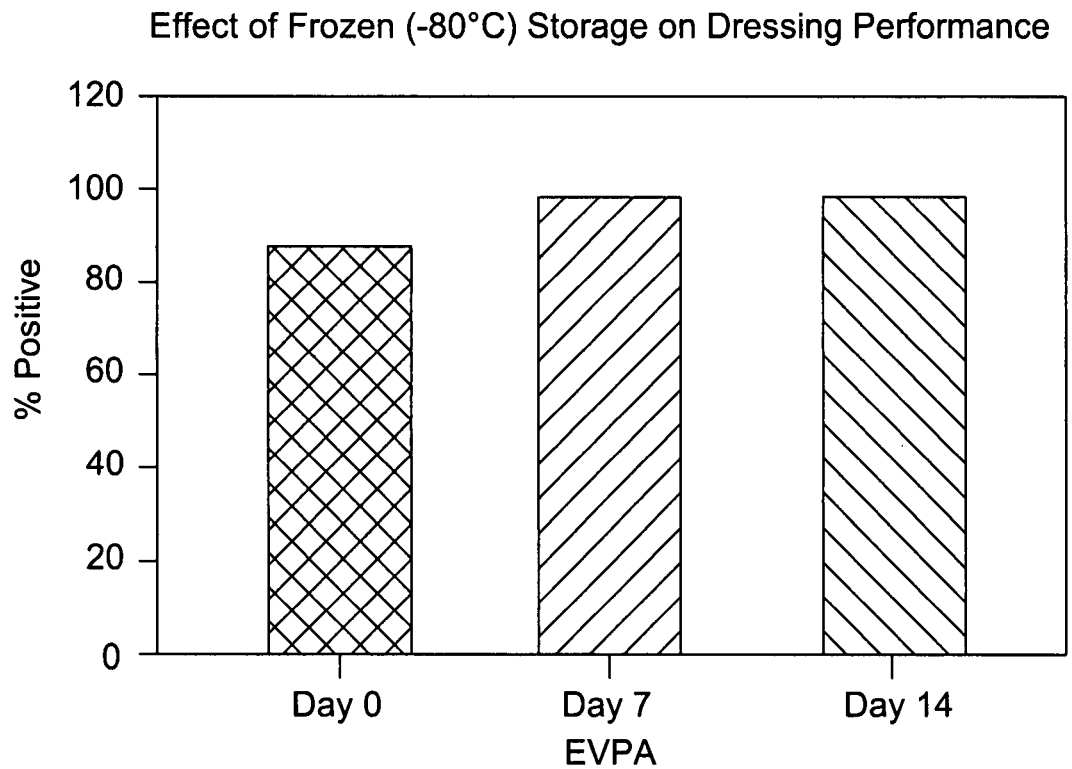
FIGS. 5A and 5B are graphs showing the performance characteristics of frozen compositions stored at −80° C. as shown in Example 13.
Figure 5B:
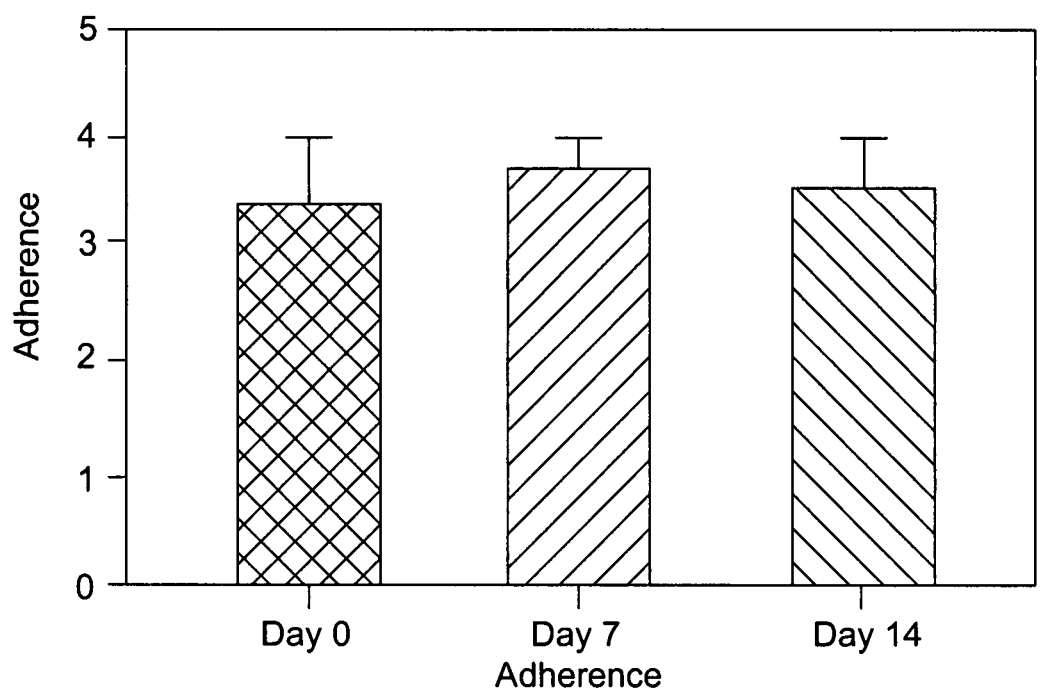

These are also shown graphically in FIG. 5A and FIG. 5B.

Conclusions:

The compositions of fully mixed, frozen fibrinogen and thrombin remained stable and functional for 7 and 14 days, with no apparent degradation in their performance. Longer storage would be expected to produce similar results.

Example 14

Backing material was cut and placed into each PETG 2.4× 2.4 cm mold. Twenty-five microliters of 2% sucrose was pipetted on top of each of the four corners of the backing material, Once completed the molds were placed in a −80° C. freezer for at least 60 minutes.

Dressings Group 1 (no Albumin, no Tween 80): Enzyme Research Laboratories (ERL) Fibrinogen lot 3130 was formulated in 100 mM Sodium Chloride, 1.1 mM Calcium Chloride, 10 mM Tris, 10 mM Sodium Citrate, and 1.5% Sucrose. The final pH of the fibrinogen was 7.4±0.1. The fibrinogen concentration was adjusted to 37.5 mg/ml.

Dressings Group 2 (no Albumin, Tween 80): ERL Fibrinogen was formulated in 100 mM Sodium Chloride, 1.1 mM Calcium Chloride, 10 mM Tris, 10 mM Sodium Citrate, and 1.5% Sucrose. Tween 80 (animal source) was added to 15 mg/g total protein. The final pH of the fibrinogen was 7.4±0.1. The fibrinogen concentration was adjusted to 37.5 mg/ml.

Dressings Group 3 (Albumin, no Tween 80): ERL Fibrinogen was formulated in 100 mM Sodium Chloride, 1.1 mM Calcium Chloride, 10 mM Tris, 10 mM Sodium Citrate, and 1.5% Sucrose. HSA was added to 80 mg/g of total protein. The final pH of the fibrinogen was 7.4±0.1. The fibrinogen concentration was adjusted to 37.5 mg/ml.

Dressings group 4 (Albumin, Tween 80): ERL Fibrinogen was formulated in 100 nM Sodium Chloride, 1.1 mM Calcium Chloride, 10 mM Tris, 10 mM Sodium Citrate, and 1.5% Sucrose (Fibrinogen complete buffer). In addition, HSA was added to 80 mg/g of total protein and Tween 80 (animal source) was added to 15 mg/g total protein. The final pH of the fibrinogen was 7.4±0.1. The fibrinogen concentration was adjusted to 37.5 mg/ml. Once prepared, the fibrinogen solutions were placed on ice until use.

Thrombin was formulated in 150 mM Sodium Chloride, 40 mM Calcium Chloride, 10 mM Tris and 100 mM L-Lysine with the addition of HSA at 100 ug/ml. The final pH of the thrombin was 7.4±0.1. The thrombin was adjusted to deliver 0.1 Units/mg of fibrinogen or 25 Units/ml thrombin. Once prepared the thrombin solution was placed on ice until use.

The temperature of the fibrinogen and thrombin solutions prior to dispensing was 4° C.±2° C. Molds were removed from the −80° C. freezer and placed on an aluminum plate that was placed on top of dry ice. A repeat pipetor was filled with fibrinogen solution and second repeat pipetor was filled with thrombin solution. Simultaneously 2 ml of fibrinogen solution and 300 micro liters of thrombin solution were dispensed into each mold. Once the molds were filled they were returned to the −80° C. freezer for at least two hours before being placed into the freeze dryer.

Results:

| Formulation | EVPA # Pass/Total | Adherence | Adherence Std Dev | Weight Held (mean) (g) | Weight Held Std Dev |
|---|---|---|---|---|---|
| −Alb − Tween | 0/6 | 0.8 | 1.0 | 24.0 | 26.3 |
| −Alb + Tween | 3/6 | 3.3 | 0.8 | 114.7 | 40.8 |
| +Alb − Tween | 1/6 | 1.7 | 1.0 | 45.0 | 39.9 |
| +Alb + Tween | 5/6 | 3.5 | 0.5 | 131.3 | 32.0 |

Conclusions:

The results show that the addition of Albumin improved dressing performance. The addition of Tween improved performance even further. The combination of both resulted in the best performance.

Example 15

Molds consisted of a pair of aluminum plates, separated by a plastic spacer of 3/16" Plexiglas with 1"×1" square notches cut into it. In use, the open side of the notches was oriented to the top of the vertically mounted plate-spacer-plate "sandwich" which together formed the mold for the dressing. The mold was pre-cooled by submersion in dry ice pellets, with the top standing slightly above the dry ice. Backing material was then cut and placed into each mold. ERL fibrinogen was formulated in CFB. The final pH of the fibrinogen was 7.4±0.1. The fibrinogen concentration was adjusted to produce dressings with 13 mg/cm$^2$ of fibrinogen in the final product. Thrombin was formulated in CTB. The final pH of the thrombin was 7.4±0.1. The thrombin was adjusted to deliver 0.1 Units/mg of fibrinogen in the final dressing.

Fibrinogen and thrombin were chilled to the required temperatures (2, 4, 6 and 8° C.) and mixed in a pre-chilled 15 ml conical tube and mixed using a vortex at high speed for 5 seconds, prior to dispensing into the molds. The fibrinogen-thrombin mixture was then pipetted into the molds using a serological pipette.

Results:

| Initial Temperature of Fibrinogen and Thrombin (° C.) | Performance Testing | | Biochemical Characterization | |
|---|---|---|---|---|
| | EVPA (Passed/ Tested) | Adherence (Mean) | % Aα Converted to Free α Chain | % of γ Chain Converted to γ-γ Dimer |
| 2 | 5/5 | 4.0 | 51 | 0 |
| 4 | 5/5 | 4.0 | 38 | 0 |
| 6 | 5/5 | 3.8 | 57 | 0 |
| 8 | 4/4 | 4.0 | 44 | 0 |

Conclusions:

Functional dressings were made that comprised between 38-57% free α chain and no γ-γ dimer.

Example 16

Molds consisted of a pair of aluminum or steel plates, separated by a plastic spacer of 3/16" Plexiglas with 1"×1" square notches cut into it. In use, the open side of the notches was oriented to the top of the vertically mounted plate-spacer-plate "sandwich" which together formed the mold for the dressings. In some groups, a thin plastic (PVC) liner was used to provide the product contact surface for the mold cooling plates. The molds were pre-cooled to the desired temperature, and backing material was cut and placed into each mold.

ERL fibrinogen was formulated in CFB. The final pH of the fibrinogen was 7.4±0.1. The fibrinogen concentration was adjusted to produce dressings with 13 mg/cm$^2$ of fibrinogen in the final product. Thrombin was formulated in CTB. The final pH of the thrombin was 7.4±0.1. The thrombin was adjusted to deliver 0.1 units/mg of Fibrinogen in the final dressing.

Fibrinogen and thrombin were dispensed into the molds. Once the molds were filled they were allowed to freeze, and then kept at −80° C.s before being placed into the freeze dryer. Dressings were then lyophilized as described above. Once complete the dressings were stored in low moisture transmission foil bags containing 5 grams of desiccant.

Dressings were evaluated from performance in the EVPA and Adherence assays as described previously. Biochemical characterization of the manufactured dressings was performed by the gel electrophoresis assay as described above.

Results:

Conclusions:

Dressings were manufactured that passed all performance tests. The percentage of free α chain ranged from 46 to 56%, while there was no detectable γ-γ dimer in any of the dressings.

Example 17

Molds consisted of a pair of aluminum plates, separated by a plastic spacer of 3/16" Plexiglas with 1"×1" square notches cut into it. In use, the open side of the notches was oriented to the top of the vertically mounted plate-spacer-plate "sandwich" which together formed the mold for the dressings. The mold was pre-cooled by submersion in dry ice pellets, with the top standing slightly above the dry ice. Backing material was then cut and placed into each mold. ERL fibrinogen was formulated in CFB. The final pH of the fibrinogen was 7.4±0.1. The fibrinogen concentration was adjusted to produce dressings with 13 mg/cm$^2$ of fibrinogen in the final product. Thrombin was formulated in CTB. The final pH of the thrombin was 7.4±0.1. The thrombin was adjusted to deliver 0.1 units/mg of Fibrinogen in the final dressing.

Fibrinogen and thrombin were kept on ice and either: added to a pre-chilled 15 ml conical tube and mixed using a vortex at high speed for 5 seconds and then pipetted into the molds using a serological pipette, or loaded into a 60 mL syringe for dispensing fibrinogen and a 3 mL syringe for dispensing thrombin, the syringes placed into a linear syringe pump, and tubing used to connect each syringe to opposite ends of a T-shaped connector. The pump was then activated and the bottom portion of the connector was used to dispense the fibrinogen-thrombin mixture into the molds.

Once the molds were filled they were allowed to freeze, and then kept at −80° C.s before being placed into the freeze dryer. Dressings were then lyophilized as described above. Once complete the dressings were stored in low moisture transmission foil bags containing 5 grams of desiccant.

Dressings were evaluated from performance in the EVPA and Adherence assays as described previously. Biochemical characterization of the manufactured dressings was performed by the gel electrophoresis assay as described above.

| Freezing | | | Performance Testing | | | Biochemical Characterization | |
|---|---|---|---|---|---|---|---|
| Plate Temperature (° C.) | Plate Material | Plate to Dressing Interface | EVPA (Passed/ Tested) | Adherence (Mean ±− Std Dev) | Weight (Mean ±− Std Dev) | % Aα Converted to Free α Chain | % of γ Chain Converted to γ-γ Dimer |
| −20 | Aluminum | Aluminum | 5/5 | 4.0 ± 0.0 | 180 ± 16.7 | 53 | 0 |
| −30 | " | " | 5/5 | 4.0 ± 0.0 | 162 ± 34.4 | 51 | 0 |
| −40 | " | " | 5/5 | 4.0 ± 0.0 | 184 ± 21.9 | 56 | 0 |
| −60 | " | " | 5/5 | 4.0 ± 0.0 | 198 ± 30.8 | 55 | 0 |
| " | Steel | Plastic | 5/5 | 3.8 ± 0.4 | 158 ± 25.5 | 53 | 0 |
| " | " | Steel | 5/5 | 4.0 ± 0.0 | 172 ± 33.6 | 46 | 0 |

Results:

|  | Performance Testing | | | Biochemical Characterization | |
|---|---|---|---|---|---|
| | | | | | % of γ Chain |
| Mixing Method | EVPA # Pass/Total | Adherence Score (Mean ± Std Dev) | Weight Held (g) (Mean ± Std Dev) | % Aα Converted to Free α Chain | Converted to γ-γ Dimer |
| T Fitting | 0/2 | 0.0 ± 0.0 | 0.0 ± 0.0 | 100 | 55 |
| Vortexing | 0/1 | 0 | 0.0 | 100 | 58 |

Conclusions:

Dressings were produced that failed all performance tests. The free α levels in these dressings was 100% indicating complete conversion from native fibrinogen to Fibrin Ia. The γ-γ dimer level ranged from 55-58%. There were not differences between the methods used to mix the fibrinogen and thrombin.

Example 18

Backing material was cut and placed into each PVC 1.5× 1.5 cm mold. Fifteen microliters of 2% sucrose was pipetted on top of each of the four corners of the backing material. Once completed the molds were placed in a −80° C. freezer for at least 60 minutes. ERL fibrinogen lot 3112 was formulated in CFB. The final pH of the fibrinogen was 7.4±0.1. The fibrinogen concentration was adjusted to 37.5 mg/ml. Once prepared the fibrinogen was placed on ice until use. Thrombin was formulated in CTB. The final pH of the thrombin was 7.4±0.1. Thrombin was adjusted to deliver the following amounts 0.1 units/mg of Fibrinogen or 25.0 Units/ml thrombin. Once prepared the thrombin was placed on ice until use. The temperature of the fibrinogen and thrombin prior to dispensing was 4° C.±2° C.

Molds were removed from the −80° C. freezer and placed on an aluminum plate that was placed on top of dry ice. 2.4 ml of fibrinogen was pipetted into a 12×75 mm, pre-chilled tube, followed by the addition of 360 μl of thrombin. Tubes were vortexed for 3 seconds and 897 ul aliquots were removed and pipetted into molds. Six time points (25 seconds, 1, 2, 3, 5, and 8 minutes) and one control dressings were manufactured. Control dressings were not pre-mixed, 780 ul of fibrinogen and 117 μl of thrombin were simultaneously pipetted into molds on dry ice. Once each mold was filled they were placed in the −80° C. freezer for at least two hours before being placed into the freeze dryer.

Results:

|  | Performance Testing | | | Biochemical Characterization | |
|---|---|---|---|---|---|
| | | | | | % of γ Chain |
| Mixing Hold Time | EVPA # Pass/Total | Adherence Score (Mean ± Std Dev) | Weight Held (g) (Mean ± Std Dev) | % Aα Converted to Free α Chain | Converted to γ-γ Dimer |
| Control | 3/4 | 2.8 ± 0.5 | 61 ± 15.0 | 0 | 0 |
| 25 sec | 4/4 | 3.3 ± 0.5 | 93 ± 26.5 | nt* | nt |
| 1 min | 5/5 | 3.0 ± 0.0 | 86 ± 11.0 | nt | nt |
| 2 min | 5/5 | 3.2 ± 0.4 | 94 ± 32.1 | nt | nt |
| 3 min | 5/5 | 2.6 ± 0.5 | 74 ± 26.1 | 20 | 0 |
| 5 min | 4/4 | 2.8 ± 1.0 | 83 ± 23.8 | 26 | 0 |
| 8 min | 3/3 | 2.7 ± 0.6 | 81 ± 15.3 | 42 | 0 | nt: not tested

Conclusions:

Fully functional dressings were manufactured with free α levels from 0 to 42%.

Example 19

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

Enzyme Research Laboratories (ERL) Fibrinogen lot 3112 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and several groups placed on steel freeze dryer shelves. Shelf temperatures were the following, −10° C., −20° C., −30° C., and −40° C. and the molds were placed on the shelf for 30 minutes to allow for equilibration. A 3 ml syringe fitted with an 18 gauge needle was filled with 2 ml of fibrinogen and a second 1 ml syringe fitted with a 22 gauge needle was filled with 0.3 ml of thrombin. Simultaneously both syringes were dispensed into each mold. Once the molds were filled they remained inside the freeze dryer at their set temperatures for 30 minutes. After which they were returned to the −80° C. freezer for at least 2 hours before freeze drying as described previously.

In addition, two groups of dressings were manufactured by being placed on an aluminum plate that was placed on top of dry ice. A 3 ml syringe fitted with an 18 gauge needle was filled with 2 ml of fibrinogen and a second 1 ml syringe fitted with a 22 gauge needle was filled with 0.3 ml of thrombin. Simultaneously both syringes were dispensed into each mold. Once the molds were filled they either remained on the dry ice for 5 minutes or they were placed on liquid nitrogen for 30 seconds. After which they were returned to the −80° C. freezer for at least 2 hours before freeze drying as described previously.

The lyophilized dressings were tested for performance in the EVPA, Adherence and Weigh assays. Additionally, they were analyzed using the gel electrophoresis assay as described.

Results:

| Freezing Temperature(s) | Performance Testing | | Weight | Biochemical Characterization | |
|---|---|---|---|---|---|
| | EVPA # Pass/Total | Peel Test Adherence (±Std. Dev.) | Held (mean) (g) | % Aα Converted to Free α Chain | % of γ Chain Converted to γ-γ Dimer |
| −10 | 2/5 | 0.1 ± 0.2 | 6.0 ± 12.5 | 33 | 0 |
| −20 | 2/4 | 0.0 ± 0.0 | 0 ± 0 | 19 | 0 |
| −30 | 4/5 | 1.3 ± 1.2 | 68 ± 39.2 | 11 | 0 |
| −40 | 3/5 | 1.5 ± 1.2 | 74 ± 77.8 | 16 | 0 |
| Dry Ice (−78°) | 4/5 | 1.8 ± 1.3 | 50 ± 47.1 | 11 | 0 |
| Dry Ice (−78° C.) and Liquid N$_2$ (−196° C.) | 5/5 | 2.8 ± 0.8 | 126 ± 39.6 | 10 | 0 |

Conclusions:

Dressings were manufactured with free α chain levels from 10% to 33%, and no detectable γ-γ dimer. Performance was inversely correlated with the level of free α chain, and with freezing temperature(s).

Example 20

Human fibrinogen (Sigma, St. Louis) was formulated in CFB at a concentration of 35 mg of fibrinogen/ml, Bovine thrombin (Sigma, St. Louis) was formulated in CTB at 87.5 U/ml. The pH of the buffers was adjusted to suit the target pH for each well.

The range of pH for both fibrinogen and thrombin was 5.5 to 8.5, in 0.5 unit increments. Two test temperatures were used, 4° C. and 24° C. The experiment was carried out in flat bottom 96 well ELISA plates (Nalgene, VWR).

One hundred μl of fibrinogen was pipetted into each well (3.5 mg/well) of the 96 well plates, followed by the addition of 100 μl of thrombin (8.75 U/well). See plate setup below. The plate was allowed to incubate for 10 minutes before evaluation. Clot formation and structure were evaluated by: inversion to detect clot formation and adherence, and opacity.

Plate Setup:

| | Fibrinogen pH | | | | | | |
|---|---|---|---|---|---|---|---|
| Thrombin pH | 5.5 | 6.0 | 6.5 | 7.0 | 7.5 | 8.0 | 8.5 |
| 5.5 | | | | | | | |
| 6.0 | | | | | | | |
| 6.5 | | | | | | | |
| 7.0 | | | | | | | |
| 7.5 | | | | | | | |
| 8.0 | | | | | | | |
| 8.5 | | | | | | | |

Figure 6A:
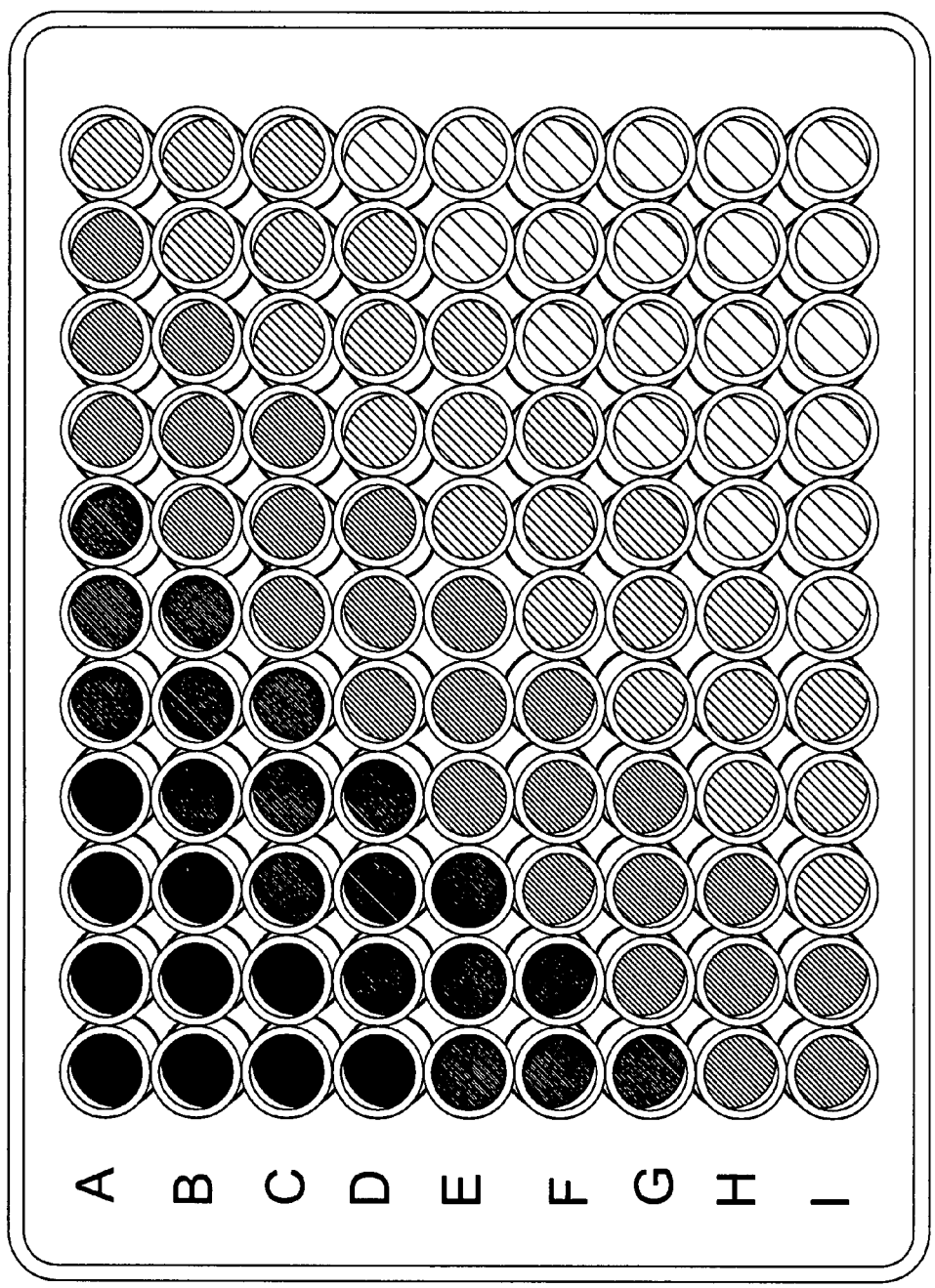

Results:

Room Temperature Plate:

Clots were formed in all wells. Fibrinogen at pH of 5.5 and 6.0 had clots that were very opaque at all pH ranges of the thrombin. The pH of fibrinogen at 6.5 had clots that were opaque using thrombin between pH ranges of 5.5 to 7.0. With thrombin above pH 7.5 the clots were clear. Fibrinogen at pH levels of 7.0 and above formed clear clots at all pH levels of thrombin. The results are shown in FIG. 6A.

Figure 6B:
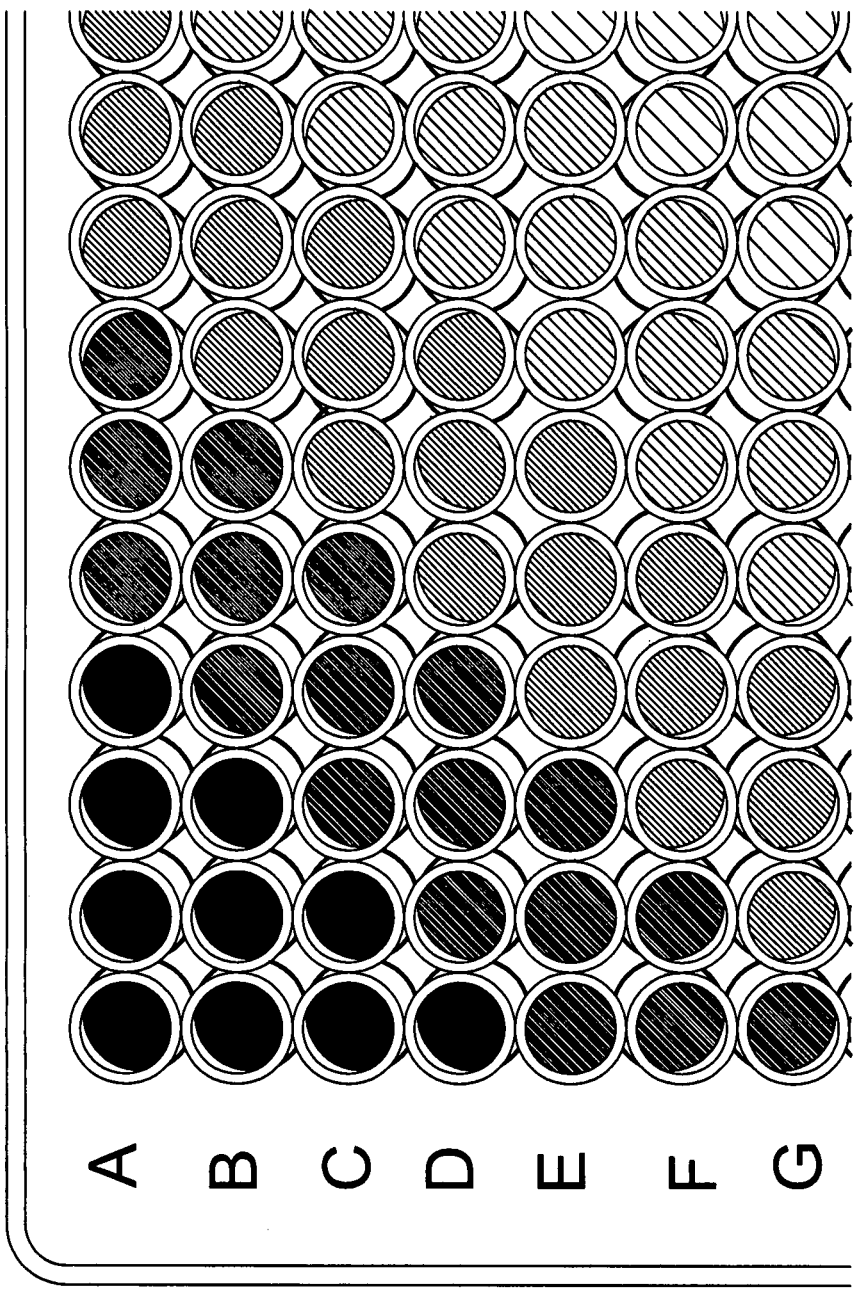

4° C. Plate:

Clots were formed in all wells. Fibrinogen at pH of 5.5 and 6.0 had clots that were very opaque at all pH ranges of the thrombin. The pH of fibrinogen at 6.5 had clots that were opaque using thrombin between pH ranges of 5.5 to 7.0. With thrombin above pH 7.5 the clots were clear. Fibrinogen at pH levels of 7.0 and above formed clear clots at all pH levels of thrombin. The results are shown in FIG. 6B.

Adherence:

Adherence of clots was determined by inverting the plate on a paper towel and lightly tapping the back of the plate. The plate was removed after 30 seconds and clots that remained in the plate were considered adherent, whereas clots that landed on the paper towel were not adherent.

Observations:

Although clots were formed that varied in their opaqueness, clots formed using fibrinogen at pH 5.5 and 6.0 lacked adherence. This was also true for fibrinogen at pH 6.5 when the thrombin pH was between 5.5 and 7.0. Once the fibrinogen pH was 7.0 or greater, adhesive clots were formed at all thrombin pH ranges tested. This was true for both room temperature and 4° C. plates.

Conclusions:

From these results it was determined that dressings preferably have fibrinogen at a pH of 7.0 or greater, but the pH of the thrombin may vary from 5.5 to 8.5.

Example 21

Human fibrinogen (Sigma, St. Louis) was formulated in modified CFB (that lacked calcium chloride) at a concentration of 35 mg of fibrinogen/ml, Bovine thrombin (Sigma, St. Louis) was formulated in modified CTB (that lacked calcium chloride) at 87.5 U/ml. The pH of the buffers was adjusted to suit the target pH for each well.

The range of pH for both Fibrinogen and Thrombin was 5.5 to 8.5, in 0.5 unit increments. Two test temperatures were used, 4° C. and 24° C. The experiment was carried out in flat bottom 96 well ELISA plates (Nalgene, VWR).

One hundred μl of fibrinogen was pipetted into each well (3.5 mg/well) of the 96 well plates, followed by the addition of 100 μl of Thrombin (8.75 U/well). See plate setup below. The plate was allowed to incubate for 10 minutes before evaluation. Clot formation and structure were evaluated by: inversion to detect clot formation and adherence, and opacity.

Plate Setup:

|             | Fibrinogen pH |     |     |     |     |     |     |
|-------------|-----|-----|-----|-----|-----|-----|-----|
| Thrombin pH | 5.5 | 6.0 | 6.5 | 7.0 | 7.5 | 8.0 | 8.5 |
| 5.5         |     |     |     |     |     |     |     |
| 6.0         |     |     |     |     |     |     |     |
| 6.5         |     |     |     |     |     |     |     |
| 7.0         |     |     |     |     |     |     |     |
| 7.5         |     |     |     |     |     |     |     |
| 8.0         |     |     |     |     |     |     |     |
| 8.5         |     |     |     |     |     |     |     |

Figure 6C:
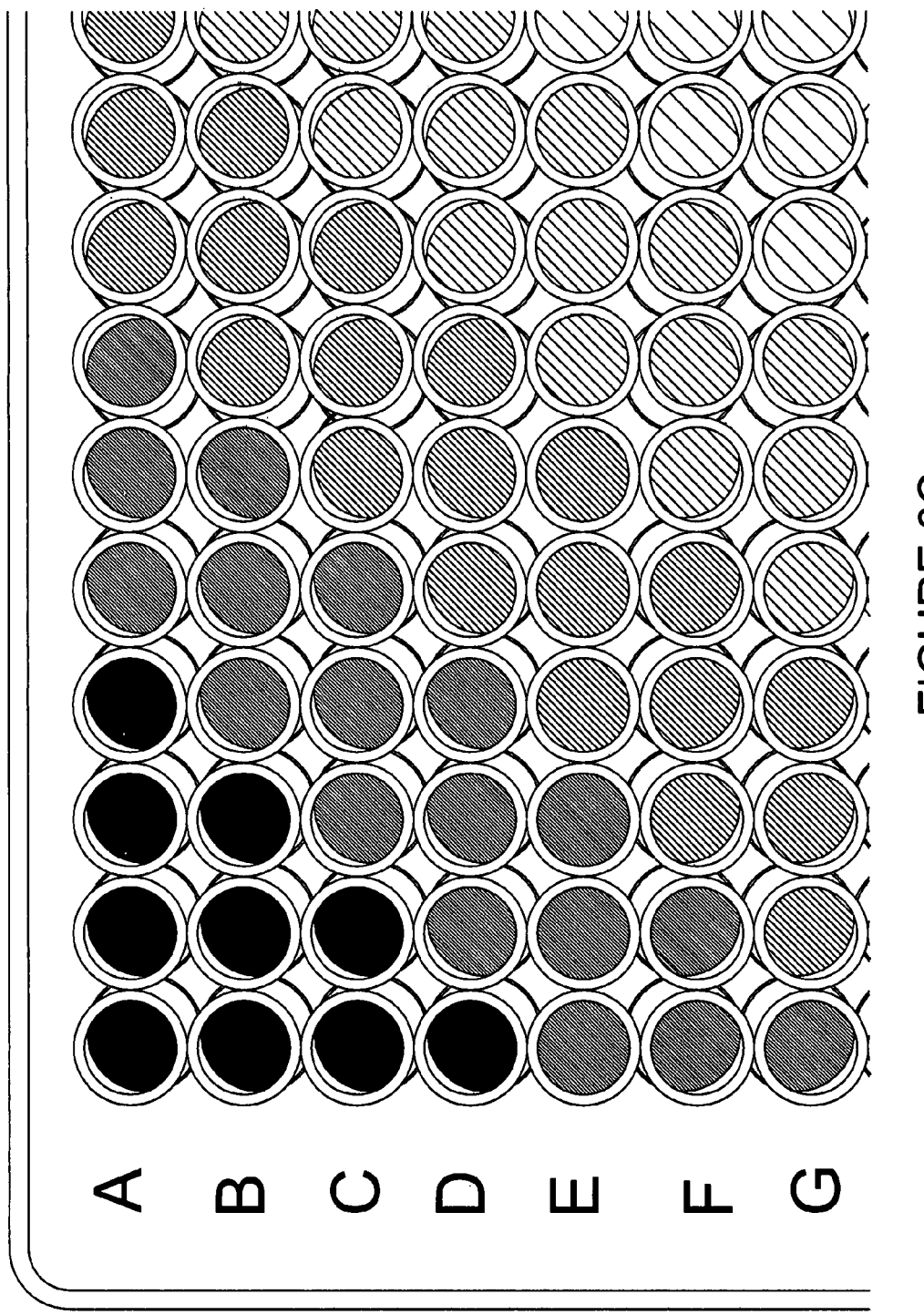

Results:

Room Temperature Plate:

Clots were formed in all wells. Fibrinogen at pH of 5.5 and 6.0 had clots that were very opaque at all pH ranges of the thrombin. The pH of fibrinogen at 6.5 had clots that were not opaque using thrombin between pH ranges of 5.5 to 8.5 which is different than the previous results. With thrombin above pH 7.5 the clots were clear. Fibrinogen at pH levels of 6.5 and above formed clots at all pH levels of thrombin. The results are shown in FIG. 6C.

4° C. Plate:

Clots were formed in all wells. Fibrinogen at pH of 5.5 and 6.0 had clots that were very opaque at all pH ranges of the thrombin. The pH of fibrinogen at 6.5 had clots that were opaque using thrombin between pH ranges of 5.5 to 7.0. With thrombin above pH 7.5 the clots were clear. Fibrinogen at pH levels of 7.0 and above formed clots at all pH levels of thrombin. The results are shown in FIG. 6D.

Adherence:

Adherence of clots was determined by inverting the plate on a paper towel and lightly tapping the back of the plate. The plate was removed after 30 seconds and clots that remained in the plate were considered adherent, whereas clots that landed on the paper towel were not adherent.

Observations:

Although clots were formed that varied in their opaqueness, clots formed using fibrinogen at pH 5.5 and 6.0 lacked adherence. Once the fibrinogen pH was 6.5 or greater, adhesive clots were formed at all thrombin pH ranges tested. This was true for both room temperature and 4° C. plates. These results are different than the previous results in that fibrinogen at pH 6.5 formed adhesive clots when the buffer did not contain $CaCl_2$.

Conclusions:

From these results it was determined that in the absence of $CaCl_2$, dressings should have fibrinogen at a pH of 6.5 or greater, but the pH of the thrombin could vary from at least 5.5 to 8.5.

Example 22

Human fibrinogen (Sigma, St. Louis) was formulated in CFB at a concentration of 35 mg of fibrinogen/ml. Bovine thrombin (Sigma, St. Louis) was formulated in CTB at 87.5 U/ml. The pH of the buffers was adjusted to suit the target pH for each well. The dressings were manufactured in Disposable 2.4×2.4 cm histology molds. Absorbable backing material. Syringes (2.0 ml). Vertical, bi-directional freezing on dry ice.

Backing material was placed into each 2.4×2.4 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes.

Fibrinogen (Sigma) was formulated in CFB. The fibrinogen concentration was adjusted to 37.5 mg/ml using CFB. The final pH of the fibrinogen was adjusted as shown below. Once prepared the fibrinogen was placed on ice until use.

Thrombin was formulated in CTB. The final pH of the thrombin was adjusted as shown below. The thrombin concentrations were adjusted using CTB to deliver the 0.1 units/mg of Fibrinogen (upon mixing), which corresponded to 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed between aluminum plates that were precooked in dry ice. Three holes were punched at the top of the mold using an 18 gauge needle. One hole was used for injecting fibrinogen, the second for injecting thrombin. These holes were located at the opposite ends of the molds, and the third hole, which was located in the center of the top of the mold, served as a vent to release air that was displaced from inside the mold. Two 3 ml syringes were then filled with 2.0 ml fibrinogen and thrombin respectively. These were then simultaneously injected into the molds via the two holes at the ends of the mold. Once filled the molds were covered with dry ice pellets and allowed to freeze for 2 minutes, after which they were returned to the −80° C. freezer for at least two hours before being placed into the freeze dryer. They were then lyophilized as described below.

Dressing Manufacturing Combinations:

| Dressing # | Fibrinogen pH | Thrombin pH |
|------------|---------------|-------------|
| 1          | 5.5           | 6.0         |
| 2          | 6.0           | 6.5         |
| 3          | 6.5           | 8.0         |
| 4          | 7.0           | 7.0         |
| 5          | 7.5           | 7.0         |
| 6          | 8.0           | 7.5         |
| 7          | 8.5           | 7.5         |

Evaluation Criteria

Dressings were evaluated for their appearance. Extensive experience with the manufacture of fibrin sealant based dressings has established that dressings that appear to be made up of a significant amount of powdered material are poor performers. Similarly, the visual detection of pre-formed fibrin in the dressings correlates inversely with performance, as this indicates that the dressing will have poor adherence. The ease and rate of hydration is also readily assessed, with good dressing performance being predicted by a dressing that easily and rapidly hydrates in an even manner. Finally, the ability to form a clot that consists of dense and uniform fibrin is also required for good performance and can be evaluated visually.

All dressings were evaluated visually. In addition, dressings 1-4 and 6 were hydrated with 2 ml of 37° C. water and the speed of hydration, their ability to form a clot, and their subsequent adherence evaluated visually.

Figure 7A:
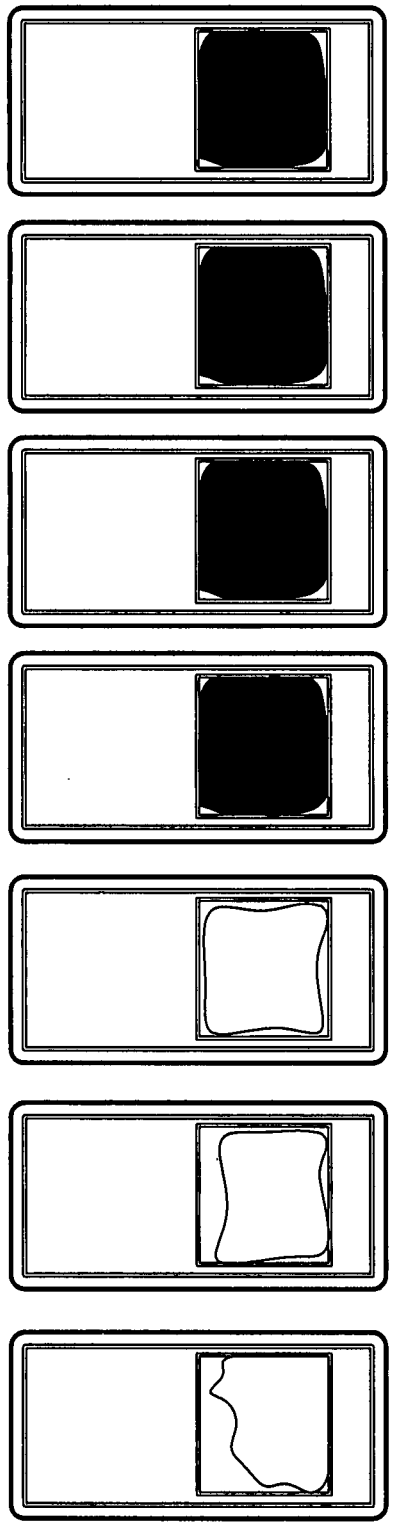
Figure 7B:
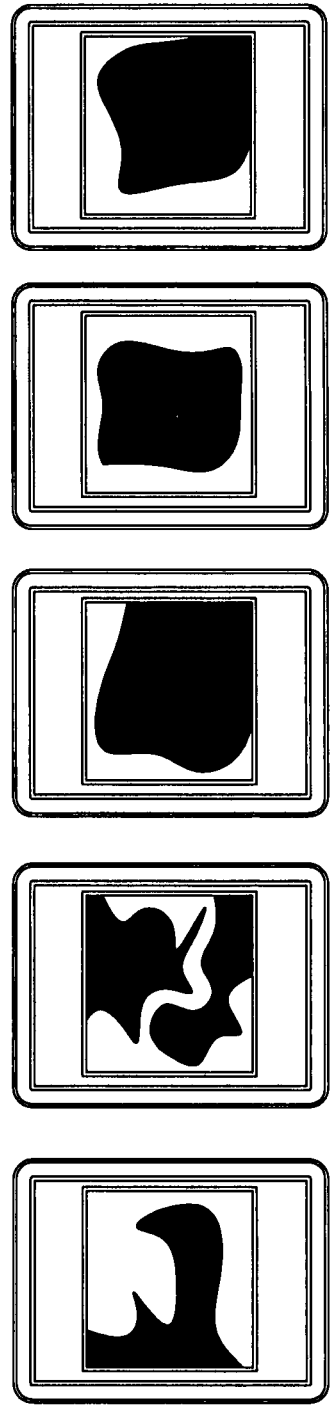

Results:

Appearance Post Freeze Drying:

All dressings were easily assessed by visual criteria (see FIGS. 7A and 7B) Dressings 1 and 2 were very powdery compared to the other dressings. The relative proportion of the dressing that was powdered decreased as the pH of the fibrinogen increased.

Dressings 1 and 2 had some pre formed fibrin, which can be seen in the picture below as the dense white mottled areas, whereas dressings 3, 4 and 6 had a large amount of pre-formed fibrin and were slow to solubilize. In contrast, dressing number 5 had a high integrity and had no visually detectable pre-formed fibrin. These results are summarized in the Table below.

| Dressing # | Fibrinogen pH | Thrombin pH | Integrity | Pre-Formed Fibrin | Speed of Hydration |
|---|---|---|---|---|---|
| 1 | 5.5 | 6.0 | Very powdery | Yes | Moderate |
| 2 | 6.0 | 6.5 | Powdery | " | " |
| 3 | 6.5 | 8.0 | Good | Large Proportion | Difficult and Slow |
| 4 | 7.0 | 7.0 | Excellent | Yes | Difficult and Slow |
| 5 | 7.5 | 7.0 | " | None | Not Tested |
| 6 | 8.0 | 7.5 | " | Large Proportion | Difficult and Slow |
| 7 | 8.5 | 7.5 | " | Yes | Not Tested |

Conclusions

The dressing characteristics are given in the Table above. All dressings formed clots at all portions of the pH range. Those with fibrinogen pH between 5.5 and 6.0 and thrombin between 6.0 and 6.5 had the least integrity prior to hydration. They also had a small amount of fibrin formed prior to hydration. Those with a fibrinogen pH between 6.5 to 7.0 and thrombin pH between 8.0 and 7.0 had greater integrity, but more fibrin prior to hydration. Dressings made using Fibrinogen between 8.0 and 8.5, and thrombin at 7.5 had good integrity, but showed large amounts of pre-hydration fibrin and were difficult to hydrate. In contrast, when both Fibrinogen and Thrombin were at pH 7.0, the resulting dressing had excellent integrity and a smaller amount of pre-formed fibrin. The best dressings were obtained using a combination of fibrinogen at pH 7.5 and thrombin at a pH of 7.0.

Example 23

Backing material (Dexon™) was cut and placed into each PVC 1.5×1.5 cm mold. Fifteen microliters of 2% sucrose was pipetted on top of each of the four corners of the backing material. A second piece of PETG plastic was cut to fit on top of the 1.5×1.5 molds and held in place by the addition of binder clips located at each end of the mold. In this way the mold was closed. Once completed the molds were placed in a −80° C. freezer for at least 60 minutes.

ERL fibrinogen lot 3100 was formulated in CFB. The final pH of the fibrinogen was 7.4±0.1. The fibrinogen concentration was adjusted to 37.5 mg/ml with CFB. Once prepared the fibrinogen was placed on ice until use.

Thrombin was formulated in CTB. The final pH of the thrombin was 7.4±0.1. Thrombin was adjusted with CTB to deliver the 0.1 units/mg of Fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed between two aluminum plates in an upright (vertical) position and then placed on dry ice. Three holes were punched at the top of the mold using an 18 gauge needle. One hole was used for entrance for fibrinogen, the second was for the entrance of thrombin and third hole was used to release any air that was in the mold. A pipette was filled with fibrinogen and second pipette was filled with thrombin. Simultaneously 0.78 ml of fibrinogen and 0.17 ml of thrombin were dispensed into each mold. Once each mold was filled they were placed on top of liquid nitrogen for thirty seconds and then returned to the −80° C. freezer for at least two hours before being placed into the freeze dryer and lyophylized as described previously.

Results:

| Group | EVPA # Pass/Total | Adherence Test Score (Mean ± Std. Dev. |
|---|---|---|
| Closed/Vertical | 5/5 | 3.4 ± 0.5 |

Conclusions:

From these results it was determined that dressings manufactured with an overall pH between 7.3 to 7.5 gave excellent performance.

Example 24

For dressings utilizing a backing, the backing material was cut and placed into each PETG 2.4×2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophylized as described.

Results:

| Group | EVPA # Pass/Total | Peel Test Adherence | Adherence Std Dev | Weight Held (mean) (g) | Weight Held Std Dev |
|---|---|---|---|---|---|
| Open/ Horizontal | 6/6 | 3.7 | 0.5 | 153 | 37.3 |

Example 25

Backing material was placed into each 1.5×1.5 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1. The thrombin concentrations were adjusted using CTB to deliver 0.1 units/mg of Fibrinogen (upon mixing), which corresponded 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed on an aluminum plate that was precooled on top of dry ice. Three holes were punched at the top of the mold using an 18 gauge needle. One hole was used for injecting fibrinogen, the second for injecting thrombin, and the third hole served as a vent to release air that was displaced from inside the mold. A pipette was then filled with fibrinogen and a second pipette with thrombin. Simultaneously 0.78 ml of fibrinogen and 0.17 ml of thrombin were injected via these pipettes into each mold. Once filled the molds were placed on top of a pool of liquid nitrogen for thirty seconds and then returned to the −80° C. freezer for at least two hours before being placed into the freeze dryer. They were then lyophilized as described.
Results:

| Group | EVPA # Pass/Total | Peel Test Adherence | Adherence Std Dev |
|---|---|---|---|
| Closed/ Vertical | 5/5 | 3.4 | 0.5 |

Example 26

For all dressings, ERL fibrinogen lot 3130 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. For the group with shredded Vicryl mesh dispersed within, this support material was cut into approximately 1 mm×1 mm pieces and dispersed within the thrombin solution prior to filling the molds. Once prepared the thrombin was placed on ice until use.

The temperature of the fibrinogen and thrombin prior to dispensing was 4° C.±2° C. Cylindrical molds made of 10 or 3 mL polypropylene syringes (Becton Dickinson) with the luer-lock end removed were used. The plungers were withdrawn to the 6 and 2 mL mark respectively. For dressings utilizing a backing, the support material was cut and placed into each mold and pushed down until it was adjacent to the plunger. Once prepared the molds were placed upright and surrounded by dry ice, leaving the opening exposed at the top. 1 ml of fibrinogen and 0.15 mL of thrombin (with or without backing material dispersed within) were dispensed into the 10 mL molds and 1 ml of fibrinogen and 0.15 mL of thrombin (with or without support material dispersed within) were dispensed into the 3 mL molds, which were allowed to freeze for 5 minutes. The molds were then placed into the −80° C. freezer for at least two hours before being placed into the freeze dryer and lyophylized as described.
Results:

| Group | EVPA # Pass/Total |
|---|---|
| Tubular (Syringe) | 3/3 |

Summary

| Group | EVPA # Pass/Total | Peel Test Adherence | Adherence Std Dev | Weight Held (mean) (g) | Weight Held Std Dev |
|---|---|---|---|---|---|
| Open/ Horizontal | 6/6 | 3.7 | 0.5 | 153 | 37.3 |
| Closed/ Vertical | 5/5 | 3.4 | 0.5 | | |
| Tubular (Syringe) | 3/3 | | | | |

Conclusions:

Dressings were manufactured that passed the EVPA test for manufacturing conditions.

Example 27

Backing material was placed into each 1.5×1.5 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1. The thrombin concentrations were adjusted using CTB to deliver 0.1 units/mg of Fibrinogen (upon mixing), which corresponded 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed on an aluminum plate that was precooled on top of dry ice. Three holes were punched at the top of the mold using an 18 gauge needle. One hole was used for injecting fibrinogen, the second for injecting thrombin, and the third hole served as a vent to release air that was displaced from inside the mold. A pipette was then filled with fibrinogen and a second pipette with thrombin. Simultaneously 0.78 ml of fibrinogen and 0.17 ml of thrombin were injected via these pipettes into each mold. Once filled the molds were placed on top of a pool of liquid nitrogen for thirty seconds and then returned to the −80° C. freezer for at least two hours before being placed into the freeze dryer. They were then lyophilized as described.
Results:

| Group | EVPA # Pass/Total | Peel Test Adherence | Adherence Std Dev |
|---|---|---|---|
| Pipet | 5/5 | 3.4 | 0.5 |

Example 28

For dressings utilizing a backing, the backing material was cut and placed into each PETG 2.4×2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophilized as described.
Results:

| Group | EVPA # Pass/Total | Peel Test Adherence | Adherence Std Dev | Weight Held (mean) (g) | Weight Held Std Dev |
|---|---|---|---|---|---|
| Repeat Pipetor | 6/6 | 3.7 | 0.5 | 153 | 37.3 |

Example 29

Backing material was placed into 2.4×2.4 cm PVC molds. Twenty-five microliters of 2% sucrose was pipetted on top of each of the four corners of the backing material. Once completed the molds were placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1 The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. The molds were removed from the −80° C. freezer and placed on an aluminum plate that that was precooled on top of dry ice. A 3 ml syringe fitted with an 18 gauge needle was filled with 2 ml of fibrinogen and a second, 1 ml, syringe fitted with a 22 gauge needle was filled with 0.3 ml of thrombin. The contents of both syringes were dispensed simultaneously into each mold. Once filled the molds were placed on top of liquid nitrogen for thirty seconds and then returned to the −80° C. freezer for at least two hours before being placed into the freeze dryer. They were then lyophilized as described.
Results:

| Group | EVPA # Pass/Total | Peel Test Adherence | Adherence Std Dev |
|---|---|---|---|
| Syringe | 4/4 | 3.8 | 0.5 |

Example 30

Backing material was cut and placed into each PETG 10×10 cm mold. Fifty microliters of 2% sucrose was pipeted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. The mold was removed from the −80° C. freezer and placed on an aluminum plate that was placed on top of dry ice. The aluminum plate had a 0.25 inch hole drilled in the center and a fitting attached so that a piece of tubing could be attached to a vacuum source. The mold was centered over the hole in the aluminum plate and vacuum was turned on. The vacuum served two purposes it prevented the mold from moving and it held it flat against the aluminum plate. Thirty-five milliliters of fibrinogen and 5.25 milliliters of Thrombin were placed in 50 ml test tube, inverted three times and poured into the mold. Once the molds were filled and the support material applied as described above, they were returned to the −80° C. freezer for at least two hours before being placed into the freeze dryer. Dressings were then lyophilized as described.

Results:

| Group | EVPA # Pass/Total | Peel Test Adherence | Adherence Std Dev | Weight Held (mean) (g) | Weight Held Std Dev |
|---|---|---|---|---|---|
| Mix and Pour | 6/6 | 3.8 | 0.4 | 163 | 31.5 |

Example 31

Backing material was cut and placed into each PVC 1.5× 1.5 cm mold. Fifteen microliters of 2% sucrose was pipeted on top of each of the four corners of the backing material. Molds were placed in a −80° C. freezer for at least 60 minutes.

ERL fibrinogen lot 2890 formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use. The thrombin was adjusted to deliver 0.1 units/mg of fibrinogen or 25 Units/ml thrombin.

The temperature of the fibrinogen and thrombin prior to dispensing was 4° C.±2° C. Molds were removed from the −80° C. freezer and placed on an aluminum plate that was placed on top of dry ice. Two automated dispensing systems from IJ Fisner were assembled according to the manufactures instructions. One syringe was filled with fibrinogen and a second was filled with thrombin. Simultaneously 0.78 ml of fibrinogen and 0.17 ml of thrombin were dispensed into each mold. Once each mold was filled they were placed on top of liquid nitrogen for thirty seconds and then returned to the −80° C. freezer for at least two hours before being placed into the freeze dryer.

Results:

| Group | EVPA # Pass/Total | Peel Test Adherence | Adherence Std Dev |
|---|---|---|---|
| Dispenser | 5/5 | 4.0 | 0.0 |

Summary:

| Group | EVPA # Pass/Total | Peel Test Adherence | Adherence Std Dev | Weight Held (mean) (g) | Weight Held Std Dev |
|---|---|---|---|---|---|
| Pipet | 5/5 | 3.4 | 0.5 | | |
| Repeat Pipetor | 6/6 | 3.7 | 0.5 | 153 | 37.3 |
| Syringe | 4/4 | 3.8 | 0.5 | | |
| Mix and Pour | 6/6 | 3.8 | 0.4 | 163 | 31.5 |
| Dispenser | 5/5 | 4.0 | 0.0 | | |

Conclusions:

Dressings manufactured using many various filling techniques all passed the assays they were tested against. This shows that there is acceptable mixing of the thrombin and fibrinogen components under many various filling procedures.

Example 32

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophilized as described.

Results:

| Group | EVPA # Pass/Total | Peel Test Adherence | Adherence Std Dev | Weight Held (mean) (g) | Weight Held Std Dev |
|---|---|---|---|---|---|
| Uni-directional | 6/6 | 3.7 | 0.5 | 153 | 37.3 |

Example 33

Backing material was placed into each 1.5×1.5 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1. The thrombin concentrations were adjusted using CTB to deliver 0.1 units/mg of fibrinogen (upon mixing), which corresponded 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed on an aluminum plate that was precooled on top of dry ice. Three holes were punched at the top of the mold using an 18 gauge needle. One hole was used for injecting fibrinogen, the second for injecting thrombin, and the third hole served as a vent to release air that was displaced from inside the mold. A pipette was then filled with fibrinogen and a second pipette with thrombin. Simultaneously 0.78 ml of fibrinogen and 0.17 ml of thrombin were injected via these pipettes into each mold. Once filled the molds were placed on top of a pool of liquid nitrogen for thirty seconds and then returned to the −80° C. freezer for at least two hours before being placed into the freeze dryer. They were then lyophilized as described.
Results:

| Group | EVPA # Pass/Total | Peel Test Adherence | Adherence Std Dev |
|---|---|---|---|
| Bi-directional | 5/5 | 3.4 | 0.5 |

Example 34

ERL fibrinogen lot 3130 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. For the group with shredded Vicryl mesh dispersed within, this support material was cut into approximately 1 mm×1 mm pieces and dispersed within the thrombin solution prior to filling the molds. Once prepared the thrombin was placed on ice until use.

The temperature of the fibrinogen and thrombin prior to dispensing was 4° C.±2° C. Cylindrical molds made of 10 or 3 mL polypropylene syringes (Becton Dickinson) with the luer-lock end removed were used. The plungers were withdrawn to the 6 and 2 ml mark respectively. For dressings utilizing a backing, the support material was cut and placed into each mold and pushed down until it was adjacent to the plunger. Once prepared the molds were placed upright and surrounded by dry ice, leaving the opening exposed at the top. 1 ml of fibrinogen and 0.15 ml of thrombin (with or without backing material dispersed within) were dispensed into the 10 ml molds and 1 ml of fibrinogen and 0.15 mL of thrombin (with or without support material dispersed within) were dispensed into the 3 mL molds, which were allowed to freeze for 5 minutes. The molds were then placed into the −80° C. freezer for at least two hours before being placed into the freeze dryer and lyophilized as described.
Results:

| Group | EVPA # Pass/Total |
|---|---|
| Surround | 3/3 |

Conclusions:
Dressings that were manufactured and frozen under various conditions all passed the assays that were used for each example. Fibrinogen and thrombin can be combined as liquids and frozen under a variety of conditions.

Example 35

Backing material was placed into each 1.5×1.5 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7f.4±0.1. The thrombin concentrations were adjusted using CTB to deliver 0.1 units/mg of fibrinogen (upon mixing), which corresponded 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed on an aluminum plate that was precooled on top of dry ice. Three holes were punched at the top of the mold using an 18 gauge needle. One hole was used for injecting fibrinogen, the second for injecting thrombin, and the third hole served as a vent to release air that was displaced from inside the mold. A pipette was then filled with fibrinogen and a second pipette with thrombin. Simultaneously 0.78 ml of fibrinogen and 0.17 ml of thrombin were injected via these pipettes into each mold. Once filled the molds were placed on top of a pool of liquid nitrogen for thirty seconds and then returned to the −80° C. freezer for at least two hours before being placed into the freeze dryer. They were then lyophilized as described.
Results:

| Group | EVPA # Pass/Total | Peel Test Adherence | Adherence Std Dev | Appearance |
|---|---|---|---|---|
| 1.5 × 1.5 cm | 5/5 | 3.4 | 0.5 | Smooth, Acceptable |

Example 36

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophylized as described.

Results:

| Group | EVPA # Pass/Total | Peel Test Adherence | Adherence Std Dev | Weight Held (mean) (g) | Weight Held Std Dev | Appearance |
|---|---|---|---|---|---|---|
| 2.4 × 2.4 cm | 6/6 | 3.7 | 0.5 | 153 | 37.3 | Smooth, Acceptable |

Example 37

Backing material was cut and placed into each PETG 10×10 cm mold. Fifty microliters of 2% sucrose was pipeted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. The mold was removed from the −80° C. freezer and placed on an aluminum plate that was placed on top of dry ice. The aluminum plate had a 0.25 inch hole drilled in the center and a fitting attached so that a piece of tubing could be attached to a vacuum source. The mold was centered over the hole in the aluminum plate and vacuum was turned on. The vacuum served two purposes it prevented the mold from moving and it held it flat against the aluminum plate. Thirty-five milliliters of fibrinogen and 5.25 milliliters of Thrombin were placed in 50 ml test tube, inverted three times and poured into the mold. Once the molds were filled and the support material applied as described above, they were returned to the −80° C. freezer for at least two hours before being placed into the freeze dryer. Dressings were then lyophylized as described.
Results:

| Group | EVPA # Pass/Total | Peel Test Adherence | Adherence Std Dev | Weight Held (mean) (g) | Weight Held Std Dev | Appearance |
|---|---|---|---|---|---|---|
| 10 × 10 cm | 6/6 | 3.8 | 0.4 | 163 | 31.5 | Smooth, Acceptable |

Example 38

Backing material was cut and placed into each PETG 3.7×2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3100 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on an aluminum plate that was placed on top of dry ice. A pipet was filled with fibrinogen and second pipet was filled with thrombin. Simultaneously 3.1 ml of fibrinogen and 0.465 ml of thrombin were dispensed into each mold. Once each mold was filled they were placed on top of liquid nitrogen for thirty seconds and then returned to the −80° C. freezer for at least two hours before being placed into the freeze dryer. Dressings were then lyophylized as described.
Results:

| Group | EVPA # Pass/Total | Peel Test Adherence | Adherence Std Dev | Appearance |
|---|---|---|---|---|
| 3.7 × 2.4 cm | 5/5 | 3.4 | 0.5 | Smooth, Acceptable |

Example 39

Backing material was cut and placed into a round 63.6 cm² mold. Fifty microliters of 2% sucrose was pipeted on top of the backing material. Once completed the mold was placed in a −80° C. freezer for at least 60 minutes.

ERL fibrinogen lot 3100 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. The mold was removed from the −80° C. freezer and placed on an aluminum plate that was placed on top of dry ice. Twenty-two milliliters on fibrinogen and 3.3 milliliters of Thrombin were placed in 50 ml test tube, inverted three times and poured into the mold. Once the mold was filled it was placed on top of liquid nitrogen for thirty seconds then returned to the −80° C. freezer for at least two hours before being placed into the freeze dryer. Dressings were then lyophylized as described.
Results:

| Group | Appearance |
|---|---|
| 63.6 cm$^2$ | Smooth, Acceptable |

Example 40

Backing material was cut and placed into a round 63.6 cm$^2$ mold. Fifty microliters of 2% sucrose was pipeted on top of the backing material. Once completed the mold was placed in a −80° C. freezer for at least 60 minutes.

ERL fibrinogen lot 3100 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. The mold was removed from the −80° C. freezer and placed on an aluminum plate that was placed on top of dry ice. For the 5.2×5.6 cm mold 10.1 milliliters of fibrinogen and 1.5 milliliters of thrombin were placed in 50 ml test tube, inverted three times and poured into the mold. The 13.0×8.0 cm mold received 36 ml of fibrinogen and 5.4 ml of thrombin. The 7.0×3.0 cm mold received 7.3 ml of fibrinogen and 1.1 ml of thrombin. Once filled the molds were returned to the −80° C. freezer for at least two hours before being placed into the freeze dryer. Dressings were then lyophylized as described.
Results:

| Group | EVPA # Pass/Total | Peel Test Adherence | Adherence Std Dev | Weight Held (mean) (g) | Weight Held Std Dev | Appearance |
|---|---|---|---|---|---|---|
| 5.2 × 5.6 cm | | | | | | Smooth, Acceptable |
| 13.0 × 8.0 cm | 8/8 | 3.3 | 1.0 | 99 | 43 | Smooth, Acceptable |
| 7.0 × 3.0 cm | 3/3 | 4 | 0 | 121 | 55 | Smooth, Acceptable |

Example 41

Backing material was cut and placed into a round 63.6 cm$^2$ mold. Fifty microliters of 2% sucrose was pipeted on top of the backing material. Once completed the mold was placed in a −80° C. freezer for at least 60 minutes.

ERL fibrinogen lot 3112 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. The mold was removed from the −80° C. freezer and placed on an aluminum plate that was placed on top of dry ice. For the 5.5×6.0 cm mold 11.5 milliliters of fibrinogen and 1.73 milliliters of thrombin were placed in 50 ml test tube, inverted three times and poured into the mold. The 10.0×8.0 cm mold received 27.7 ml of fibrinogen and 4.16 ml of thrombin. The 12.0×8.0 cm mold received 37.4 ml of fibrinogen and 5.62 ml of thrombin. Once each mold was filled it was returned to the −80° C. freezer for at least two hours before being placed into the freeze dryer.
Results:

| Group | Appearance |
|---|---|
| 5.5 × 6.0 cm | Smooth, Acceptable |
| 10.0 × 8.0 cm | Smooth, Acceptable |
| 12.0 × 9.0 cm | Smooth, Acceptable |

Conclusions:

Dressings can be produced in a number of sizes ranging from small (2.25 cm$^2$) to large (108 cm$^2$). All of the dressings produced passed their respective test criteria. As long as mixing of the reagents and freezing time and temperature are controlled dressings can be manufactured to any reasonable, useful and acceptable size.

Example 42

Backing material was placed into each 1.5×1.5 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1. The thrombin concentrations were adjusted using CTB to deliver 0.1 units/mg of fibrinogen (upon mixing), which corresponded 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed on an aluminum plate that was precooled on top of dry ice. Three holes were punched at the top of the mold using an 18 gauge needle. One hole was used for injecting fibrinogen, the second for injecting thrombin, and the third hole served as a vent to release air that was displaced from inside the mold. A pipette was then filled with fibrinogen and a second pipette with thrombin. Simultaneously 0.78 ml of fibrinogen and 0.17 ml of thrombin were injected via these pipettes into each mold. Once filled the molds were placed on top of a pool of liquid nitrogen for thirty seconds and then returned to the −80° C. freezer for at least two hours before being placed into the freeze dryer. They were then lyophilized as described.

Results:

| Group | EVPA # Pass/Total | Peel Test Adherence | Adherence Std Dev |
|---|---|---|---|
| PVC | 5/5 | 3.4 | 0.5 |

Example 43

For dressings utilizing a backing, the backing material was cut and placed into each PETG 2.4×2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophylized as described.

Results:

| Group | EVPA # Pass/Total | Peel Test Adherence | Adherence Std Dev | Weight Held (mean) (g) | Weight Held Std Dev |
|---|---|---|---|---|---|
| PETG | 6/6 | 3.7 | 0.5 | 153 | 37.3 |

Example 44

Backing material was cut and placed into stainless steel 2.4×2.4 cm molds. Twenty-five microliters of 2% sucrose was pipeted on top of each of the four corners of the backing material. Once completed the molds were placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1. The thrombin concentrations were adjusted using CTB to deliver 0.1 units/mg of fibrinogen (upon mixing), which corresponded 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed on an aluminum plate that was precooled on top of dry ice. A pipette was then filled with fibrinogen and a second pipette with thrombin. Simultaneously 2.0 ml of fibrinogen and 0.3 ml of thrombin were injected via these pipettes into each mold. Once the molds were filled they were returned to the −80° C. freezer for at least two hours before being placed into the freeze dryer. Dressings were then lyophylized as described.

Results:

| Group | EVPA # Pass/Total | Peel Test Adherence | Adherence Std Dev |
|---|---|---|---|
| Stainless Steel | 3/3 | 4.0 | 0.0 |

Example 45

ERL fibrinogen lot 3130 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. For the group with shredded Vicryl mesh dispersed within, this support material was cut into approximately 1 mm×1 mm pieces and dispersed within the thrombin solution prior to filling the molds. Once prepared the thrombin was placed on ice until use.

The temperature of the fibrinogen and thrombin prior to dispensing was 4° C.±2° C. Cylindrical molds made of 10 or 3 ml polypropylene syringes (Becton Dickinson) with the luer-lock end removed were used. The plungers were withdrawn to the 6 and 2 ml mark respectively. For dressings utilizing a backing, the support material was cut and placed into each mold and pushed down until it was adjacent to the plunger. Once prepared the molds were placed upright and surrounded by dry ice, leaving the opening exposed at the top. 1 ml of fibrinogen and 0.15 ml of thrombin (with or without backing material dispersed within) were dispensed into the 10 mL molds and 1 ml of fibrinogen and 0.15 ml of thrombin (with or without support material dispersed within) were dispensed into the 3 ml molds, which were allowed to freeze for 5 minutes. The molds were then placed into the −80° C. freezer for at least two hours before being placed into the freeze dryer and lyophylized as described.

Results:

| Group | EVPA # Pass/Total |
|---|---|
| Polypropylene | 3/3 |

Summary:

| Group | EVPA # Pass/Total | Peel Test Adherence | Adherence Std Dev | Weight Held (mean) (g) | Weight Held Std Dev |
|---|---|---|---|---|---|
| PVC | 5/5 | 3.4 | 0.5 | | |
| PETG | 6/6 | 3.7 | 0.5 | 153 | 37.3 |
| Stainless Steel | 3/3 | 4.0 | 0.0 | | |
| Polypropylene | 3/3 | | | | |

Conclusions:

Dressings can be manufactured using a variety of plastics or metal as the mold support. All of these dressings passed their test criteria.

Example 46

Backing material was cut and placed into each PETG 10×10 cm mold. Fifty microliters of 2% sucrose was pipeted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. The mold was removed from the −80° C. freezer and placed on an aluminum plate that was placed on top of dry ice. The aluminum plate had a 0.25 inch hole drilled in the center and a fitting attached so that a piece of tubing could be attached to a vacuum source. The mold was centered over the hole in the aluminum plate and vacuum was turned on. The vacuum served two purposes it prevented the mold from moving and it held it flat against the aluminum plate. Thirty-five milliliters of fibrinogen and 5.25 milliliters of Thrombin were placed in 50 ml test tube, inverted three times and poured into the mold. Once the molds were filled and the support material applied as described above, they were returned to the −80° C. freezer for at least two hours before being placed into the freeze dryer. Dressings were then lyophylized as described.
Results:

| Group | EVPA # Pass/Total | Peel Test Adherence | Adherence Std Dev | Weight Held (mean) (g) | Weight Held Std Dev |
|---|---|---|---|---|---|
| Aluminum with hole | 6/6 | 3.8 | 0.4 | 163 | 31.5 |

Example 47

Backing material was placed into each 1.5×1.5 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1. The thrombin concentrations were adjusted using CTB to deliver 0.1 units/mg of fibrinogen (upon mixing), which corresponded 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed on an aluminum plate that was precooled on top of dry ice. Three holes were punched at the top of the mold using an 18 gauge needle. One hole was used for injecting fibrinogen, the second for injecting thrombin, and the third hole served as a vent to release air that was displaced from inside the mold. A pipette was then filled with fibrinogen and a second pipette with thrombin. Simultaneously 0.78 ml of fibrinogen and 0.17 ml of thrombin were injected via these pipettes into each mold. Once filled the molds were placed on top of a pool of liquid nitrogen for thirty seconds and then returned to the −80° C. freezer for at least two hours before being placed into the freeze dryer. They were then lyophilized as described.
Results:

| Group | EVPA # Pass/Total | Peel Test Adherence | Adherence Std Dev |
|---|---|---|---|
| Aluminum | 5/5 | 3.4 | 0.5 |

Example 48

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophylized as described.

Results:

| Group | EVPA # Pass/Total | Peel Test Adherence | Adherence Std Dev | Weight Held (mean) (g) | Weight Held Std Dev |
|---|---|---|---|---|---|
| Copper | 6/6 | 3.7 | 0.5 | 153 | 37.3 |

Example 49

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3130 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on a steel freeze dryer shelf that had the temperature set at −50° C. The molds remained on the shelf for 30 minutes so the mold temperatures would equilibrate to −50° C. After 30 minutes a repeat pipettor was filled with fibrinogen and second repeat pipettor was filled with thrombin. Simultaneously 2 ml of fibrinogen and 300 micro liters of thrombin were dispensed into each mold. Once the molds were filled they remained inside the freeze dryer at −50° C. for 30 minutes. After which they were returned to the −80° C. freezer for 24 hours before being freeze dried.

Results:

| Group | EVPA # Pass/Total | Peel Test Adherence | Adherence Std Dev | Weight Held (mean) (g) | Weight Held Std Dev |
|---|---|---|---|---|---|
| Steel | 5/5 | 3.4 | 0.5 | 106 | 11 |

Summary:

| Group | EVPA # Pass/Total | Peel Test Adherence | Adherence Std Dev | Weight Held (mean) (g) | Weight Held Std Dev |
|---|---|---|---|---|---|
| Aluminum with hole | 6/6 | 3.8 | 0.4 | 163 | 31.5 |
| Aluminum | 5/5 | 3.4 | 0.5 | | |
| Copper | 6/6 | 3.7 | 0.5 | 153 | 37.3 |
| Steel | 5/5 | 3.4 | 0.5 | 106 | 11 |

Conclusions:

Dressings produced on metal plates that allow fast freezing and rapid heat transfer pass all test criteria. It would be expected that other metals or similar materials that can transfer heat at comparable rates would produce the similar results.

Example 50

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3114 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on a copper plate that was placed on top of dry ice. A repeat pipettor was filled with fibrinogen and second repeat pipettor was filled with thrombin. Simultaneously 2 ml of fibrinogen and 300 micro liters of thrombin were dispensed into each mold. Once the molds were filled they were returned to the −80° C. freezer for at least two hours before being placed into the freeze dryer. Dressings were then lyophilized as described.

Results:

| Group | EVPA # Pass/Total | Peel Test Adherence | Adherence Std Dev | Weight Held (mean) (g) | Weight Held Std Dev |
|---|---|---|---|---|---|
| Dry Ice | 6/6 | 3.7 | 0.5 | 153 | 37.3 |

Example 51

Backing material was placed into each 1.5×1.5 cm PVC molds. Fifteen microliters of 2% sucrose was pipetted on top of each of the four corners of the backing material. A second piece of PETG plastic was fitted on top of the 1.5×1.5 molds and held in place. This formed a closed mold. The molds were then placed in a −80° C. freezer for at least 60 minutes.

Fibrinogen (ERL lot 3100) was formulated in CFB. The fibrinogen concentration was adjusted to 37.5 mg/ml using CFB. The final pH of the fibrinogen was 7.4±0.1. Once prepared the fibrinogen was placed on ice until use.

Thrombin was formulated in CTB. The final pH of the thrombin was 7.4±0.1. The thrombin concentrations were adjusted using CTB to deliver 0.1 units/mg of fibrinogen (upon mixing), which corresponded 25 Units/ml thrombin prior to mixing. Once prepared the thrombin was placed on ice until use.

The temperature of the fibrinogen and thrombin prior to dispensing was 4° C.±2° C. Molds were then removed from the −80° C. freezer and placed on an aluminum plate that was precooled on top of dry ice. Three holes were punched at the top of the mold using an 18 gauge needle. One hole was used for injecting fibrinogen, the second for injecting thrombin, and the third hole served as a vent to release air that was displaced from inside the mold. A pipette was then filled with fibrinogen and a second pipette with thrombin. Simultaneously 0.78 ml of fibrinogen and 0.17 ml of thrombin were injected via these pipettes into each mold. Once filled the molds were placed on top of a pool of liquid nitrogen for thirty seconds and then returned to the −80° C. freezer for at least two hours before being placed into the freeze dryer. They were then lyophilized as described below, and performance tested using the EVPA and Adherence Assays as described.
Results:

| Group | EVPA # Pass/Total | Peel Test Adherence | Adherence Std Dev |
|---|---|---|---|
| Dry Ice and Liquid Nitrogen | 5/5 | 3.4 | 0.5 |

Example 52

Backing material was placed into 1.5×1.5 cm PVC molds. Fifteen microliters of 2% sucrose was pipetted on top of each of the four corners of the backing material. The molds were then placed in a −80° C. freezer for at least 60 minutes.

A vial containing 3 grams of Fibrinogen (Sigma Lot# F-3879) was removed the −20° C. freezer and placed at 4° C. for 18 hours. The bottle was then removed from the freezer and allowed to come to room temperature for 60 minutes. To the bottle, 60 ml of 37° C. water was added and allowed to mix for 15 minutes at 37° C. Once in solution the fibrinogen was dialyzed against IFB. At the end of the four hours HSA was added to a concentration of 80 mg/g of total protein, and Tween 80 (animal source) was added to a concentration of 15 mg/g total protein. The final pH of the fibrinogen was 7.4±0.1. The fibrinogen concentration was adjusted to 37.5 mg/ml using CFB. Once prepared the fibrinogen was placed on ice until use.

Thrombin was formulated in CTB. The final pH of the thrombin was 7.4±0.1. Thrombin concentration was adjusted to deliver 0.1 units/mg of fibrinogen (upon mixing), which corresponded to 25 Units/ml thrombin (before mixing). Once prepared the thrombin was placed on ice until use.

The temperature of the fibrinogen and thrombin prior to dispensing was 4° C.±2° C. Molds were removed from the −80° C. freezer and placed on an aluminum plate that was that was precooled on top of dry ice. A 3 ml syringe fitted with an 18 gauge needle was filled with 2 ml of fibrinogen and a second, 1 ml, syringe fitted with a 22 gauge needle was filled with 0.3 ml of thrombin. The contents of both syringes were dispensed simultaneously into each mold. Once filled the molds were placed on top of liquid nitrogen for thirty seconds and then returned to the −80° C. freezer for at least two hours before being placed into the freeze dryer. They were then lyophilized as described.
Results:

| Group | EVPA # Pass/Total | Peel Test Adherence | Adherence Std Dev |
|---|---|---|---|
| Liquid Nitrogen | 5/5 | 3.6 | 0.5 |

Example 53

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3130 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of Fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on an aluminum support that was located inside a small nitrogen freezing tunnel. Liquid nitrogen was pumped into the front of the tunnel where it then turns from a liquid to gas. This change in state and the pressure that it is entering the tunnel forces the gas up a ramp and allows it to flow over the molds and out the tunnel. Prior to the addition of fibrinogen or thrombin, the tunnel and molds were cooled with the liquid nitrogen gas for 5 minutes.

After 5 minutes a repeat pipetor was filled with fibrinogen and second repeat pipetor was filled with thrombin. The aluminum support holding the molds was slid out of the freezing tunnel. Simultaneously 2 ml of fibrinogen and 300 micro liters of thrombin were dispensed into each mold. Once the molds were filled they were returned to the inside of the freezing tunnel. Liquid nitrogen was then turned on and allowed to run for 3 minutes. After which the dressings were returned to the −80° C. freezer for at least 2 hours before being freeze dried.
Results:

| Group | EVPA # Pass/Total | Peel Test Adherence | Adherence Std Dev | Weight Held (mean) (g) | Weight Held Std Dev |
|---|---|---|---|---|---|
| Liquid Nitrogen Vapor | 3/6 | 2.8 | 0.98 | 93 | 48 |

Example 54

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3130 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on steel freeze dryer shelves. Shelf temperatures were the following, −5° C., −10° C., −15° C., −20° C., −25° C., −30° C., −40° C. and −50° C. At each temperature molds were placed on the shelf for 30 minutes to allow for equilibration. After 30 minutes a repeat pipetor was filled with fibrinogen and second repeat pipetor was filled with thrombin. Simultaneously 2 ml of fibrinogen and 300 micro liters of thrombin were dispensed into each mold. Once the molds were filled they remained inside the freeze dryer at their set temperatures for 30 minutes. After which they were returned to the −80° C. freezer for 24 hours before being freeze dried.
Results:

| Group Silicone Coolant (° C.) | EVPA # Pass/Total | Peel Test Adherence | Adherence Std Dev | Weight Held (mean) (g) | Weight Held Std Dev |
|---|---|---|---|---|---|
| −5 | 5/5 | 0.3 | 0.4 | 15.2 | 22.0 |
| −10 | 5/5 | 2.2 | 0.8 | 80.0 | 20.5 |
| −15 | 5/5 | 1.4 | 0.5 | 62.0 | 13.4 |
| −20 | 3/5 | 2.0 | 0.7 | 72.0 | 18.2 |
| −25 | 5/5 | 2.5 | 1.5 | 82 | 41.0 |
| −30 | 5/5 | 2.8 | 0.4 | 88 | 22.4 |
| −40 | 4/5 | 2.8 | 1.1 | 108 | 54.8 |
| −50 | 5/5 | 3.4 | 0.5 | 106 | 11.0 |

Example 55

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes.

ERL fibrinogen lot 3112 was formulated in CFB. The final pH of the fibrinogen was 7.4±0.1. The fibrinogen concentration was adjusted to 37.5 mg/ml. Once prepared the fibrinogen was placed on ice until use.

Thrombin was formulated in CTB. The final pH of the thrombin was 7.4±0.1. The thrombin was adjusted to deliver 0.1 units/mg of fibrinogen or 25 Units/ml thrombin. Once prepared the thrombin was placed on ice until use.

The temperature of the fibrinogen and thrombin prior to dispensing was 4° C.±2° C. Molds were removed from the −80° C. freezer and placed on steel freeze dryer shelves. Shelf temperatures were the following, −10° C., −20° C., −30° C., and −40° C. At each temperature molds were placed on the shelf for 30 minutes to allow for equilibration. A 3 ml syringe fitted with an 18 gauge needle was filled with 2 ml of fibrinogen and a second 1 ml syringe fitted with a 22 gauge needle was filled with 0.3 ml of thrombin. Simultaneously both syringes were dispensed into each mold. Once the molds were filled they remained inside the freeze dryer at their set temperatures for 30 minutes. After which they were returned to the −80° C. freezer for at least 2 hours before freeze drying.

In addition a group of dressings was manufactured by being placed on an aluminum plate that was placed on top of dry ice, either alone or followed by placement on liquid nitrogen for 30 seconds. A 3 ml syringe fitted with an 18 gauge needle was filled with 2 ml of fibrinogen and a second 1 ml syringe fitted with a 22 gauge needle was filled with 0.3 ml of thrombin. Simultaneously both syringes were dispensed into each mold. Once the molds were filled they remained on the dry ice for 5 minutes or they were placed on liquid nitrogen for 30 seconds. After which they were returned to the −80° C. freezer for at least 2 hours before freeze drying.

| Group Silicone Coolant (° C.) | EVPA # Pass/Total | Peel Test Adherence | Adherence Std Dev | Weight Held (mean) (g) | Weight Held Std Dev |
|---|---|---|---|---|---|
| −10 | 2/5 | 0.1 | 0.2 | 6.0 | 12.5 |
| −20 | 2/4 | 0.0 | 0.0 | 0 | 0 |
| −30 | 4/5 | 1.3 | 1.2 | 68 | 39.2 |
| −40 | 3/5 | 1.5 | 1.2 | 74 | 77.8 |
| Dry Ice (−78°) | 4/5 | 1.8 | 1.3 | 50 | 47.1 |
| Dry Ice (−78° C.) and Liquid Nitrogen (−196° C.) | 5/5 | 2.8 | 0.8 | 126 | 39.6 |

Summary

| Group | EVPA # Pass/Total | Peel Test Adherence | Adherence Std Dev | Weight Held (mean) (g) | Weight Held Std Dev |
|---|---|---|---|---|---|
| Dry Ice (−78° C.) | 6/6 | 3.7 | 0.5 | 153 | 37.3 |
| Dry Ice (−78°) | 4/5 | 1.8 | 1.3 | 50 | 47.1 |
| Dry Ice (−78° C.) and Liquid Nitrogen (−196° C.) | 5/5 | 3.4 | 0.5 | | |
| Dry Ice (−78° C.) and Liquid Nitrogen (−196° C.) | 5/5 | 2.8 | 0.8 | 126 | 39.6 |
| Liquid Nitrogen (−196°) | 5/5 | 3.6 | 0.5 | | |
| Liquid Nitrogen Vapor (−196° C.) | 3/6 | 2.8 | 0.98 | 93 | 48 |
| Silicone Coolant −5° C. | 5/5 | 0.3 | 0.4 | 15.2 | 22.0 |
| Silicone Coolant −10° C. | 5/5 | 2.2 | 0.8 | 80.0 | 20.5 |
| Silicone Coolant −10° C. | 2/5 | 0.1 | 0.2 | 6.0 | 12.5 |
| Silicone Coolant −15° C. | 5/5 | 1.4 | 0.5 | 62.0 | 13.4 |
| Silicone Coolant −20° C. | 3/5 | 2.0 | 0.7 | 72.0 | 18.2 |
| Silicone Coolant −20° C. | 2/4 | 0.0 | 0.0 | 0 | 0 |
| Silicone Coolant −25° C. | 5/5 | 2.5 | 1.5 | 82 | 41.0 |
| Silicone Coolant −30° C. | 5/5 | 2.8 | 0.4 | 88 | 22.4 |

-continued

| Group | EVPA # Pass/Total | Peel Test Adherence | Adherence Std Dev | Weight Held (mean) (g) | Weight Held Std Dev |
|---|---|---|---|---|---|
| Silicone Coolant −30° C. | 4/5 | 1.3 | 1.2 | 68 | 39.2 |
| Silicone Coolant −40° C. | 4/5 | 2.8 | 1.1 | 108 | 54.8 |
| Silicone Coolant −40° C. | 3/5 | 1.5 | 1.2 | 74 | 77.8 |
| Silicone Coolant −50° C. | 5/5 | 3.4 | 0.5 | 106 | 11.0 |

Example 56

Backing material was cut and placed into each PETG 2.4× 2.4 cm mold. Twenty-five microliters of 2% sucrose was pipetted on top of each of the four corners of the backing material. Once completed the molds were placed in a −80° C. freezer for at least 60 minutes. Fibrinogen (ERL lot 3150) was formulated in CFB. The fibrinogen concentration was adjusted to 37.5 mg/ml using CFB. The final pH of the fibrinogen was 7.4±/−0.1. Once prepared the fibrinogen was placed on ice until use. Thrombin was formulated in CTB. The final pH of the thrombin was 7.4±/−0.1. The thrombin concentration was adjusted using CTB to deliver 0.1 units/mg of Fibrinogen or 25 Units/ml thrombin. The temperature of the fibrinogen and thrombin prior to dispensing was 4° C.+/−2° C. Three molds were removed from the −80° C. freezer and placed on an aluminum plate that was pre-cooled on top of dry ice. A repeat pipettor was filled with fibrinogen and second repeat pipettor was filled with thrombin. Simultaneously 2 ml of fibrinogen and 300 micro liters of thrombin were dispensed into each of the molds. Once the molds were filled they were returned to the −80° C. freezer for at least two hours before being placed into the freeze dryer. This was the "Control" process for the experiment. The remaining molds were removed from the −80° C. and placed on the lab bench and allowed to equilibrate to room temperature (25° C.±5° C.). A repeat pipettor was filled with fibrinogen and second repeat pipettor was filled with thrombin. Simultaneously 2 ml of fibrinogen and 300 micro liters of thrombin were dispensed into the molds. The molds were allowed to remain at room temperature for the following times, (1, 5, 10 and 15 minutes). At the end of each time point the molds were placed on an aluminum plate that was pre-cooled on top of dry ice for 5 minutes. At the end of the 5 minutes the molds were returned to the −80° C. freezer for at least two hours before being placed into the freeze dryer. They were then lyophilized and their performance and biochemical characteristics tested as described.

Results:

| | Performance Testing | | | Biochemical Characterization | | |
|---|---|---|---|---|---|---|
| | | Adherence | | | | |
| Mixing Hold Time | EVPA # Pass/Total | Score (Mean ± Std Dev) | Weight Held (Mean ± Std Dev) | % Aα | % Aα Converted to Free α Chain | % of γ Converted to γ-γ Dimer |
| Control | 2/2 | 4.0 ± 0 | 118 ± 14 | 69 | 31 | 0 |
| 1 min | 2/2 | 3.5 ± 0.7 | 113 ± 50 | 65 | 35 | 0 |
| 5 min | 2/2 | 2.0 ± 0 | 58 ± 14 | 63 | 37 | 9 |
| 10 min | 0/2 | 2.0 ± 0 | 48 ± 0 | 45 | 55 | 39 |
| 15 min | 0/2 | 0 ± 0 | 0 ± 0 | 59 | 41 | 38 |

Conclusions

Fully functional dressings were manufactured using the Control process that contained 31% free α chain and no γ-γ dimer. Similar results were seen when the process was altered to allow the mixed fibrinogen and thrombin to sit at room temperature for one minute. When the reactants were mixed and held for 5 minutes, their performance was still acceptable, although somewhat reduced. γ-γ dimer was detected at a level of 9% in these dressings. Increasing the time further to 10 minutes resulted in an unacceptable loss of activity in the EVPA assay and a significant increase in the amount of free α chain and a high level of γ-γ dimer (39%). Increasing the holding time to 15 minutes resulted in the loss of both adherence and the ability to hold any weight.

EVPA Performance Testing

Equipment and Supplies:
  In-line high pressure transducer (Ashcroft Duralife™ or equivalent)
  Peristaltic pump (Pharmacia Biotech™, Model P-1 or equivalent)
  Voltmeter (Craftsman™ Professional Model 82324 or equivalent)
  Computer equipped with software for recording pressure or voltage information
  Tygon™ tubing (assorted sizes) with attachments
  Water bath (Baxter Durabath™ or equivalent), preset to 37° C.
  Incubation chamber (VWR™, Model 1400G or equivalent), preset to 37° C.
  Thermometer to monitor temperatures of both water bath and oven
  Assorted forceps, hemostats, and scissors 10 cc. and 20 cc. syringes with an approximately 0.6 cm hole drilled in center and smaller hole drilled through both syringe and plunger. This hole, drilled into the end of the syringe, will be used to keep the plunger drawn back and stationary.

O-rings (size 10 and 13)

Plastic Shields to fit the 10 cc and 20 cc syringes (approximately 3.5 cm in length)

P-1000 Pipetman™ with tips

Sphygmomanometer with neonatal size cuff and bladder

Programmable Logic Controller (PLC) to control the pumps to maintain the desired pressure profile (Optional. Manual control may be used if desired.)

1. Materials and Chemicals

Porcine descending aortas (Pel-Freez Biologicals™, Catalog #59402-2 or equivalent)

Cyanoacrylate glue (Vetbond™, 3M or equivalent)

18-gauge needle(s)

0.9% Saline, maintained at 37° C.

Red food coloring

Vascular Punch(es), 2.8 mm or other

Plastic Wrap

2. Artery Cleaning and Storage
  1. Store arteries at −20° C. until used.
  2. Thaw arteries at 37° C. in H$_2$O bath.
  3. Clean fat and connective tissue from exterior surface of artery.
  4. Cut the arteries into ~5 cm segments.
  5. The arteries may be refrozen to −20° C. and stored until use.

3. Artery Preparation for Assay
  1. Turn the artery inside-out so that the smooth, interior wall is facing outwards.
  2. Stretch a size 13 O-ring over a 20 cc syringe or a size 10 O-ring over a 10 cc syringe with an approximately 0.6 cm (0.25 in) hole drilled into one side.
  3. Pull the artery onto the syringe, taking care not to tear the artery or have a too loose fit. The artery should fit snugly to the syringe. Slide another O-ring of the same size onto the bottom of the syringe
  4. Carefully pull both O-rings over the ends of the artery. The distance between the O-rings should be at least 3.5 cm
  5. Using the blade of some surgical scissors, gently scrape the surface of the artery in order to roughen the surface of the artery.
  6. Use a 18-gauge needle to poke a hole through the artery over the site of the hole in the syringe barrel (see note above)
  7. The tip of the biopsy punch is inserted through the hole in the artery. Depress the punch's plunger to make an open hole in the artery. Repeat a couple of times to ensure that the hole is open and free of connective tissue.
  8. Patch holes left by collateral arteries. Generally this is done by cutting a patch from a latex glove and gluing it over the hole with cyanoacrylate glue. Allow the glue to cure for at least 10 minutes.
  9. Place the artery in the warmed, moistened container and place in the incubation chamber. Allow the arteries to warm for at least 30 minutes.

4. Solution and Equipment Preparation
  1. Check to see that the water bath and incubation chamber are maintained at 29-33° C.
  2. Make sure that there is sufficient 0.9% saline in the pump's reservoir for completion of the day's assays. Add more if needed.
  3. Place 0.9% saline and 0.9% saline with a few drops of red food coloring added into containers in a water bath so that the solutions will be warmed prior to performing the assay.
  4. Prepare the container for warming the arteries in the incubation chamber by lining with KimWipes™ and adding a small amount of water to keep the arteries moist.
  5. Check the tubing for air bubbles. If bubbles exist, turn on the pump and allow the 0.9% saline to flow until all bubbles are removed.

5. Application of the Dressing
  1. Open the haemostatic dressing pouch and remove haemostatic dressing
  2. Place the haemostatic dressing, mesh backing side UP, over the hole in the artery
  3. Slowly wet the haemostatic dressing with an amount of saline appropriate for the article being tested
      NOTE: A standard (13-15 mg/cm$^2$ of fibrinogen) 2.4× 2.4 cm haemostatic dressing should be wet with 800 µl of saline or other blood substitute. The amount of saline used can be adjusted depending on the requirements of the particular experiment being performed; however, any changes should be noted on the data collection forms.
      NOTE: Wet the haemostatic dressing drop wise with 0.9% saline warmed to 29-33° C. or other blood substitute, taking care to keep the saline from running off the edges. Any obvious differences in wetting characteristics from the positive control should be noted on data collection forms.
  4. Place the shield gently onto the haemostatic dressing, taking care that it lies flat between the O-rings. Press lightly to secure in place
  5. Wrap the artery and haemostatic dressing with plastic wrap
  6. Wrap with blood pressure cuff, taking care that the bladder is adjacent to the haemostatic dressing.
  7. Pump up the bladder to 100-120 mmHg, and monitor the pressure and pump again if it falls below 100 mmHg. Maintain pressure for 5 minutes.
      NOTE: Time and pressure can be altered according to the requirements of the experiment; changes from the standard conditions should be noted on the data collection forms.
  8. After polymerization, carefully unwrap the artery and note the condition of the haemostatic dressing. Any variation from the positive control should be noted on the data collection form.

EXCLUSION CRITERION: The mesh backing must remain over the hole in the artery. If it has shifted during the polymerization and does not completely cover the hole the haemostatic dressing must be excluded.

Figure 2:
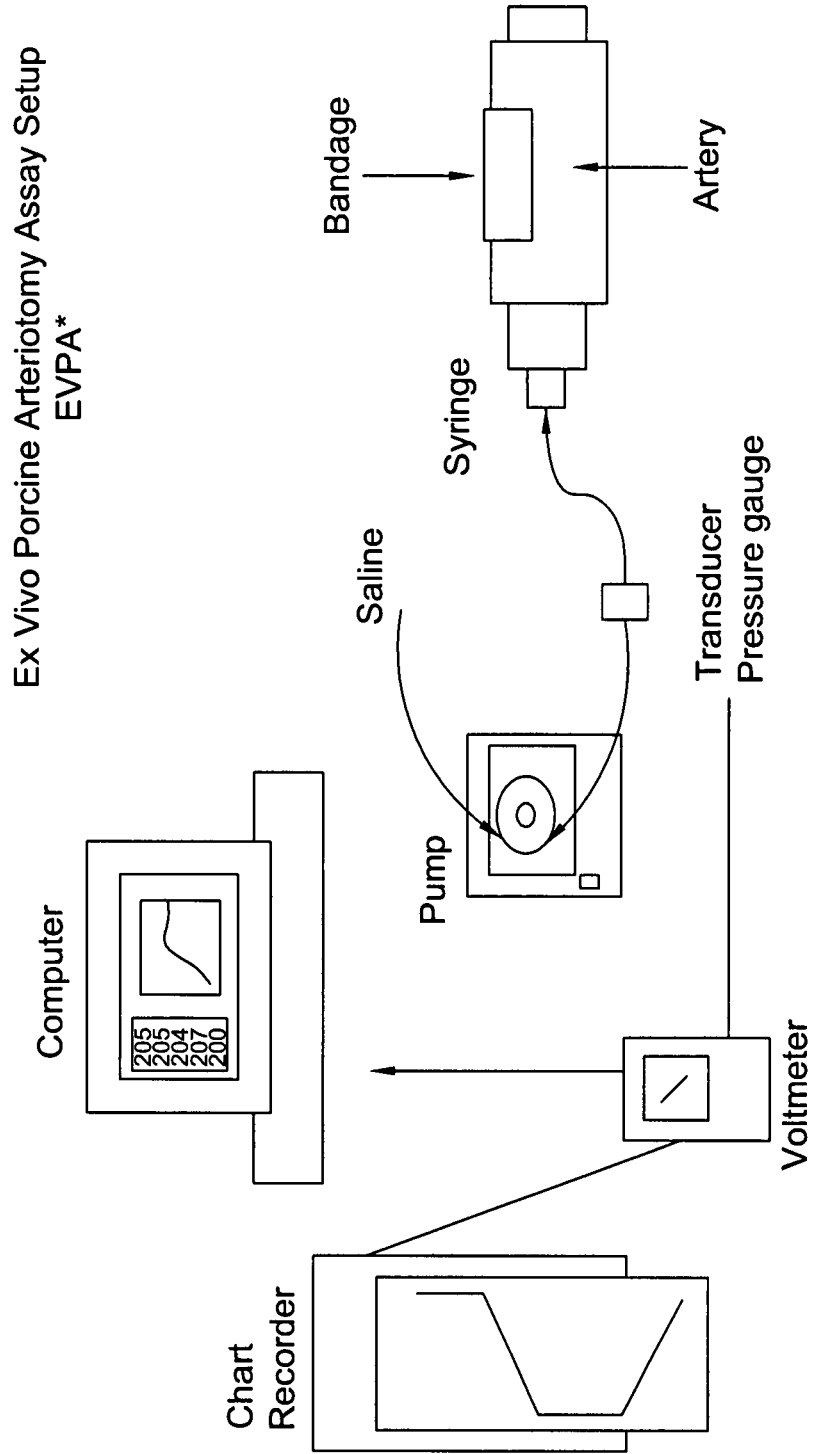
FIG. 2 is a diagram of the set-up for the ex vivo porcine arteriotomy assay described herein.

Testing Procedure
  1. Diagram of Testing Equipment Set-Up
  The set-up of the testing equipment is shown in FIG. 2. Some additional, unshown components may be utilized to read out (pressure gauge) or control the pressure within the system
  2. Equipment and Artery Assembly
  Fill the artery and syringe with red 0.9% saline warmed to 37° C., taking care to minimize the amount of air bubbles within the syringe and artery. Filling the artery with the opening uppermost can assist with this. Attach the artery and syringe to the testing apparatus, making sure that there are as few air bubbles in the tubing as possible. The peristaltic pump should be calibrated so that it delivers approximately 3 ml/min. If available, the PLC should be operated according to a pre-determined range of pressures and hold times as appropriate for the article being tested. If under manual control, the pressure/time profile to be followed is attained by manually turning the pump on and off while referencing the system pressure as read out by one or more pressure-reading components of the system. Following the conclusion of testing, the haemostatic dressing is subjectively assessed with regard to adhesion to the artery and formation of a plug in the artery hole. Any variations from the positive control should be noted on the data collection form.

Success Criteria

Haemostatic dressings that are able to withstand pressures for 3 minutes are considered to have passed the assay. When a haemostatic dressing has successfully passed the assay the data collection should be stopped immediately so that the natural decrease in pressure that occurs in the artery once the test is ended isn't included on the graphs. Should the operator fail to stop data collection, these points can be deleted from the data file to avoid confusing the natural pressure decay that occurs post-test with an actual dressing failure. The entire testing period from application of the haemostatic dressing to completion must fall within pre-established criteria. The maximum pressure reached should be recorded on the data collection form.

NOTE: Typical challenge is 250 mmHg for three minutes in one step, but that may be altered based on the article being tested. Changes from the standard procedure should be noted on the data collection forms.

Failure Criteria

Haemostatic dressings that start leaking saline at any point during testing are considered to have failed the assay.

NOTE: Build failures that are caused by artery swelling can be ignored and the test continued or re-started (as long as the total testing time doesn't fall beyond the established limit).

When leakage does occur, the pressure should be allowed to fall ~20 mmHg before data collection is stopped so that the failure is easily observed on the graphs. The pressures at which leakage occurred should be recorded on the data collection form. Should the data collection stop in the middle of the experiment due to equipment failure the data can be collected by hand at 5 second intervals until the end of the test or haemostatic dressing failure, whichever happens first. The data points should be recorded on the back of the data collection form, clearly labeled, and entered by hand into the data tables.

Exclusion Criteria

If the total testing period exceeds the maximum allowed for that procedure, regardless of cause, results must be excluded. If there are leaks from collaterals that can't be fixed either by patching or finger pressure the results must be excluded. If the test fails because of leaks at the O-rings, the results must be excluded. If the mesh backing does not completely cover the hole in the artery, the results must be excluded.

Adherence Performance Testing

1. Equipment and Supplies

Hemostat(s), Porcine artery and haemostatic dressing (usually after completion of the EVPA Assay although it does not need to be performed to do the Adherence Assay).

I. Preparation of the Artery+Dressing

After application of the dressing without completion of the EVPA Assay, the dressing is ready for the Adherence Assay and Weight Limit Test (if applicable). After application of the dressing and subsequent EVPA Analysis, the artery and syringe system is then disconnected slowly from the pump so that solution does not spray everywhere. The warmed, red saline solution from the EVPA Assay remains in the syringe until the Adherence Assay and Weight Limit Test (if applicable) is completed.

Performance of the Adherence Assay

1. After preparation of the artery and dressing (with or without EVPA analysis), gently lift the corner of the mesh and attach a hemostat of known mass to the corner.

NOTE: If the FD developed a channel leak during the performance of the EVPA Assay, test the adherence on the opposite of the haemostatic dressing to obtain a more accurate assessment of the overall adherence.

2. Gently let go of the hemostat, taking care not to allow the hemostat to drop or twist. Turn the syringe so that the hemostat is near the top and allow the hemostat to peel back the dressing as far as the dressing will permit. This usually occurs within 10 seconds. After the hemostat has stopped peeling back the dressing, rate the adherence of the bandage according to the following scale:

| Dressing Performance Score | Amount of Adherence |
| --- | --- |
| 4 | 90+% |
| 3 | 75-90% |
| 2 | 50-75% |
| 1 | ~50% |
| 0.5 | Only the plug holds the hemostat |
| 0 | No adherence |

Exclusion Criteria

The mesh backing must remain over the hole in the artery. If it has shifted during the polymerization and does not completely cover the hole the haemostatic dressing must be excluded.

Success Criteria

Dressings that are given an adherence score of 3 are considered to have passed the assay.

Failure Criteria

If a dressing does not adhere to the artery after application and/or prior to performing the EVPA assay, it is given a score of 0 and fails the adherence test. If a dressing receives a score $\leq 2$, the dressing is considered to have failed the Adherence Assay.

Weight Held Performance Assay

After the initial scoring of the "Adherence Test", weights may then be added to the hemostat in an incremental manner until the mesh backing is pulled entirely off of the artery. The maximum weight that the dressing holds is then recorded as a measure of the amount of weight the dressing could hold attached to the artery.

Moisture Assay

Moisture determinations were carried out using a Brinkman Metrohm Moisture Analyzer System. The system contains the following individual components, 774 Oven Sample Processor, 774SC Controller, 836 Titrando, 5 ml and 50 ml 800 Dosino Units and a 801 Stirrer. The system was connected to a computer using the Brinkman Tiamo software for data collection, analysis and storage. The moisture system is set-up and run according to the manufactures recommendations and specifications to measure the moisture content of lyophilized samples using the Karl Fischer method.

All components were turned on and allowed to reach operating temperature prior to use. Lactose and water were run as standards and to calibrate the instrument. Once the machine was successfully calibrated, samples were prepared as follows. Dressing pieces weighing at least 30 mg were placed into vials and capped. The vials were placed in the 774 Oven Sample Processor in numerical order, and one empty capped vial is placed in the conditioning space. The machine was then run to determine the moisture content (residual moisture) in the controls and samples.

SDS-PAGE Gel Electrophoresis

Each dressing is cut into ¼'s, approximately 50 mg per section, and a section is then placed into a 15 μl conical tube. For the production control (ie Time 0), 1.0 mL of Okuda Dissolving Solution (10 M Urea, 0.1% Sodium Dodecyl Sulfate, 0.1% β-Mercaptoethanol) is added. For the remaining 3 pieces, 80 μL of 0.9% Saline is added to wet the dressing. The pieces are then incubated at 37° C. for 2, 5, and 10 minutes or such time as desired. To stop the reaction at the desired time, 1.0 mL of the Okuda Dissolving solution is added. The samples are then incubated at room temperature overnight, and then incubated at 70° C. for 30 minutes.

To prepare the samples for loading onto the gel, the samples which were previously dissolved in the Okuda Dissolving Solution were added to Sample buffer so that a 20 μL aliquot contains 10 μg. One μL of 0.1 M Dithiothreitol was then added to each sample. Twenty μL of each diluted sample is then loaded onto an 8% Tris-Glycine gel (Invitrogen), 1.0 mm thick, 10 wells. The gels were then run at 140V until the dye front reached the end of the gel. They were then removed and placed into Coomassie Blue Stain (50% v/v Methanol, 0.25% w/v Coomassie Brilliant Blue, 10% w/v Acetic Acid in ddH2O) on a shaking platform for a minimum of 1 hour. The gel is then transferred to the Destain Solution (25% Methanol, 10% Acetic Acid, 65% ddH2O) on a shaking platform until the background is nearly colorless.

After destaining, the gels were scanned, and the γ-γ dimer bands and the Aα, and Bβ bands analyzed by Scion densitometry software in order to determine the amount of conversion that occurred.

What is claimed is:

1. A process for producing a solid dressing for treating wounded tissue in a mammal comprising: (a) forming a liquid aqueous mixture of a fibrinogen component selected from the group consisting of human fibrinogen and bovine fibrinogen, and a fibrinogen activator selected from the group consisting of human thrombin, bovine thrombin and recombinant human thrombin, at a temperature of 2° C. to 8° C., where said liquid aqueous mixture contains up to 9% γ-γ dimers; (b) reducing the temperature of said aqueous mixture to form a frozen aqueous mixture, wherein said frozen aqueous mixture contains up to 9% γ-γ dimers; and (c) reducing the moisture content of said frozen aqueous mixture to produce a solid dressing having a haemostatic layer consisting essentially of said fibrinogen component and said fibrinogen activator, wherein said haemostatic layer contains up to 9% γ-γ dimers.

2. The process of claim 1, further comprising at least one support layer.

3. The process of claim 2, wherein said support layer comprises a backing material.

4. The process of claim 2, wherein said support layer comprises an internal support material.

5. The process of claim 2, wherein said support layer comprises a resorbable material.

6. The process of claim 3, wherein said solid dressing further comprising at least one physiologically acceptable adhesive between said haemostatic layer and said backing layer.

7. The process of claim 5, wherein said resorbable materials is selected from the group consisting of proteinaceous materials and carbohydrate substances.

8. The process of claim 7, wherein said carbohydrate substance is selected from the group consisting of alginic acid and salts thereof, chitin, chitosan, cellulose, n-acetyl glucosamine, proteoglycans, glycolic acid polymers, lactic acid polymers, glycolic acid/lactic acid co-polymers and mixtures of two or more thereof.

9. The process of claim 1, wherein said haemostatic layer also contains a fibrin crosslinker and/or a source of calcium ions.

10. The process of claim 1, wherein said haemostatic layer also contains one or more of the following: at least one filler, at least one solubilizing agent, at least one foaming agent and at least one release agent.

11. The process of claim 10, wherein said solubilizing agent is selected from the group consisting of sucrose, lactose, maltose, dextrose, mannose, trehalose, mannitol, sorbitol, albumin, sorbate, polysorbate, and mixtures of two or more thereof.

12. The process of claim 2, wherein said haemostatic layer further contains at least one binding agent in an amount effective to improve the adherence of said haemostatic layer to said support layer.

13. The process of claim 12, wherein said binding agent is selected from the group consisting of sucrose, mannitol, sorbitol, gelatin, hyaluron, hyaluronic acid, maltose, povidone, chitosan and carboxymethylcellulose.

14. The process of claim 1, wherein said haemostatic layer is substantially homogeneous throughout.

15. The process of claim 1, wherein said haemostatic layer is a monolith.

16. The process of claim 1, wherein said frozen aqueous mixture is lyophilized in (c).

17. The process of claim 1, wherein said moisture content is at least 6%.

18. The process of claim 1, wherein said moisture content is less than 6%.

19. The process of claim 2, wherein said support layer comprises a front support material.

20. The process of claim 1, wherein said temperature is reduced to between −10° C. to −196° C.

21. The process of claim 1, wherein said temperature is reduced while said liquid aqueous mixture is frozen while in the horizontal or vertical orientation.

* * * * *